US007846688B2

(12) United States Patent
Gill et al.

(10) Patent No.: US 7,846,688 B2

(45) Date of Patent: Dec. 7, 2010

(54) BROAD HOST RANGE VECTORS FOR SHOTGUN AND EXPRESSION LIBRARY CLONING IN GRAM NEGATIVE BACTERIA

(75) Inventors: Ryan Gill, Boulder, CO (US); Michael Lynch, Westminster, CO (US)

(73) Assignee: The Regents of the University of Colorado, Denver, CO (US)

(*) Notice: Subject to any disclaimer, the term of this patent is extended or adjusted under 35 U.S.C. 154(b) by 775 days.

(21) Appl. No.: 11/505,147

(22) Filed: Aug. 15, 2006

(65) Prior Publication Data

US 2007/0059768 A1 Mar. 15, 2007

Related U.S. Application Data

(60) Provisional application No. 60/708,177, filed on Aug. 15, 2005.

(51) Int. Cl.
*C12N 15/00* (2006.01)
*C12N 15/10* (2006.01)

(52) U.S. Cl. .................................. 435/69.1; 435/320.1

(58) Field of Classification Search ....................... None
See application file for complete search history.

(56) References Cited

U.S. PATENT DOCUMENTS 6,709,861 B2 3/2004 Mead et al.

OTHER PUBLICATIONS

Graupner, S. et al. "A broad-host-range expression vector series including a Ptac test plasmid, . . . ".Biomolecular Engineering. Oct. 2000, 11-16 vol. 17 No. 1 Elsevier Science.

Product Description Document, CloneSmart DNA Cloning Kits. Lucigen Corporation, Middleton, WI. (2 pages).

Product Description Document for pBBR122 and pBHR1 Broad Host Range Vectors, MoBiTec GmbH, Gottingen, Germany. (2 pages), (Jun. 28, 1999).

ATCC Product Description Document for pBBR1Tp Vector, ATCC No. 87448. ATCC, Manassas, VA. (2 pages), (2008).

*Primary Examiner*—Nancy Vogel

(57) ABSTRACT

The present invention concerns methods and compositions for the construction of a series of stable vectors for genomic library construction useful in Gram negative species. In certain embodiments, the vectors contain the pBBR1 replicon, capable of to stable replication in a broad range of Gram negative species. In various embodiments, the plasmid vectors may also contain bidirectional, rho-independent transcriptional terminators flanking the multiple cloning site, which allows for greater insert stability, and thus, greater genomic representation. Each vector may vary in its selection marker region, mobilization function, and promoter used to express insert sequences. These vectors are of use in the screening of highly representational genomic libraries in a broad variety of Gram negative species.

19 Claims, 2 Drawing Sheets

Figure 1:
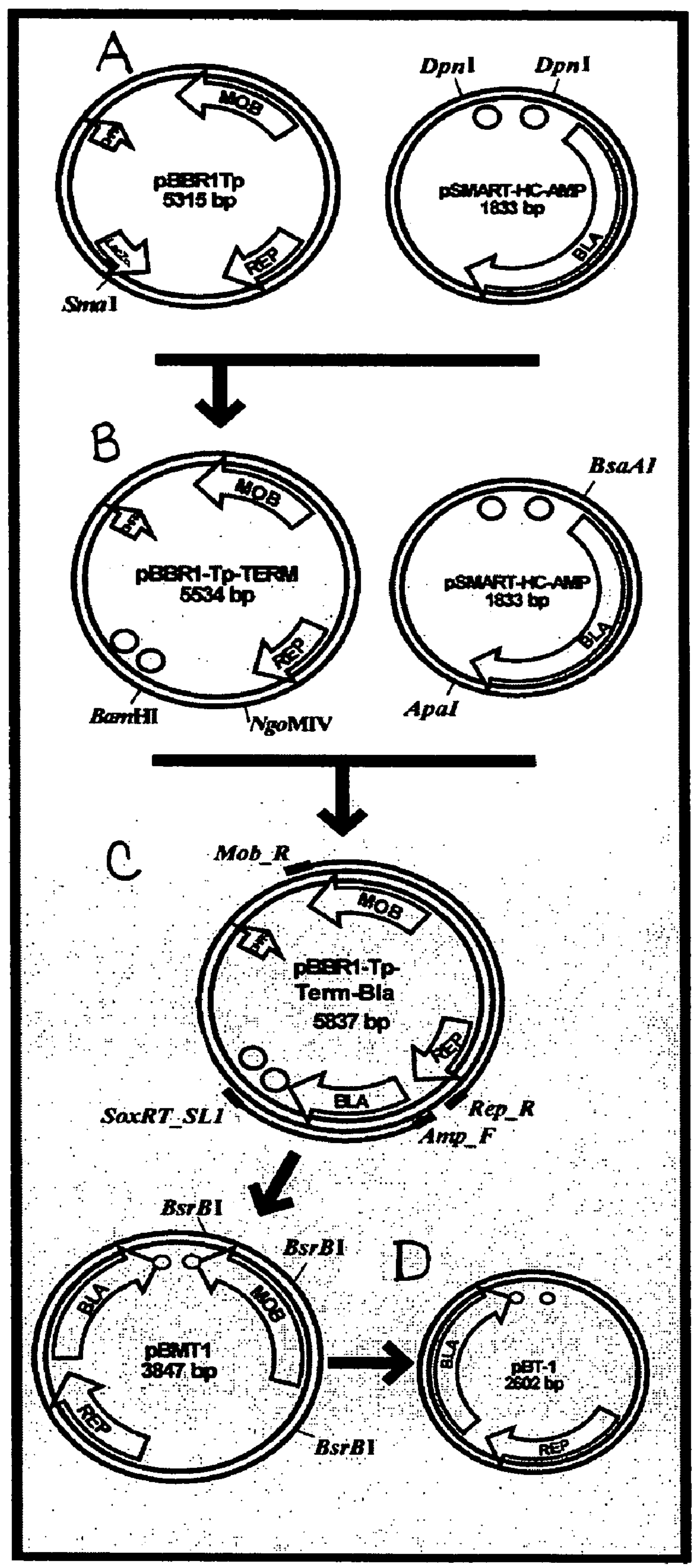

BROAD HOST RANGE VECTORS FOR SHOTGUN AND EXPRESSION LIBRARY CLONING IN GRAM NEGATIVE BACTERIA

PRIORITY CLAIM

The present application claims the benefit under 35 U.S.C. §119(e) of provisional U.S. patent application Ser. No. 60/708,177 filed on Aug. 15, 2005.

FEDERALLY FUNDED RESEARCH

The studies disclosed herein were supported in part by grants R21 AI055773-01 and F31 AI056687 from the National Institutes of Health and BES0228584 from the National Science Foundation. The U.S. Government may have certain rights to practice the subject invention.

FIELD

This application relates generally to methods, compositions and uses of broad host range vectors for stable genomic library construction. In one particular embodiment, the present invention relates to compositions and methods of generating vectors for stable genomic library construction in a broad range of Gram negative bacteria.

BACKGROUND

The screening and selection of genomic libraries is one method used to identify genetic elements that confer a particular host function. In Gram negative bacteria numerous plasmid vectors have been used for construction of these libraries. Many of these vectors were derived from pUC plasmids designed to facilitate the screening for inserts or open reading frame cloning. These vectors often contain a variety of features, such as inducible or constitutive promoters followed by ribosome binding sites and start codons, the β-galactosidase gene, and, in the case of shuttle vectors, multiple replicons. These features are not ideal for the creation of stable, extra-chromosomal genomic libraries but are beneficial for expression library construction. Other features are needed for construction of these libraries.

Further, toxicity and/or instability of present vectors available for use with Gram negative bacteria are an issue. A need exists for broad-host-range vectors that can be used in a variety of Gram negative bacteria, with improved tolerance of toxicity and/or stability.

SUMMARY OF THE INVENTION

Embodiments of the present invention provide for vector compositions for making stable genomic libraries in an organism. In one particular embodiment, a vector composition provides for creating stable genomic libraries in a broad range of Gram negative host bacteria. In accordance with this embodiment, the vector can include bi-directional, host-factor independent independent transcriptional terminators flanking a multiple cloning site; a selectable marker region; a PBBR1 replicon region or any other replicon region that is of use in a broad range of Gram negative host bacteria; and an antibiotic resistant cassette. In some embodiments, the vector is a plasmid. In a more particular embodiment, a plasmid vector of the present invention can be a mobilizable plasmid. In another embodiment, the vector can include a single origin of replication. In one particular embodiment, the origin of replication is active in a broad range of Gram-negative host bacteria.

In one particular embodiment, a vector of the present invention includes a promoter such as a constitutive, inducible or native promoter. For example, the promoter may be but is not limited to pBAD (araC gene and araB promoter make up the pBAD promoter) or pLac. In another embodiment, a vector of the present invention may include an antibiotic resistance cassette. For example, an antibiotic resistant cassette can include, but is not limited to, cassettes conferring resistance to β-lactams, kanamycin, chloramphenicol, tetracycline, trimethoprim or tellurite. Other optional features of the present invention may include ribosomal binding sites and start codons for expression within the insert sequence, terminators flanking multiple cloning sites.

In one particular embodiment, a vector of the present invention includes a promoter such as a constitutive, inducible or native promoter. For example, the promoter may be, but is not limited to, a pLac or a pBad promoter. In another embodiment, a vector of the present invention may include a selectable marker such as an antibiotic resistance cassette. For example, an antibiotic resistant cassette can include but is not limited to β-lactams, kanamycin, chloramphenicol, tetracycline, trimethoprim or tellurite. Other optional features of the present invention may include ribosomal binding sites and start codons for expression within the insert sequence, terminators flanking multiple cloning sites.

In another embodiment, compositions of the present invention can be used as a vector in a broad range of Gram negative host bacteria for constructing a genomic library. Gram negative host bacteria species included in embodiments of the present invention are selected from but not limited to *Aeromonas, Acetobacter, Agrobacterium, Alcaligenes, Azorizobium, Bartonella, Bordetella, Brucella, Burkholderia, Caulobacter, Escherichia, Erwinia, Hyphomicrobium, Methylobacillus, Methybacterium, Mehylophilus, Pseudomonus, Paracoccus, Rhizobium, Ralstonia, Rhodobacter, Salmonella, Vibrio* and *Xanthomonas.*

In addition, the present invention may include a mobilizable plasmid vector composition of use in a broad range of Gram negative host bacteria. In one particular example, these compositions can include mobilization and/or transfer functions that confer mobilization to the plasmid vector.

BRIEF DESCRIPTIONS OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

FIG. 1. illustrates an exemplary construction of a vector, pBMT-1 and pBT-1.

Figure 2:
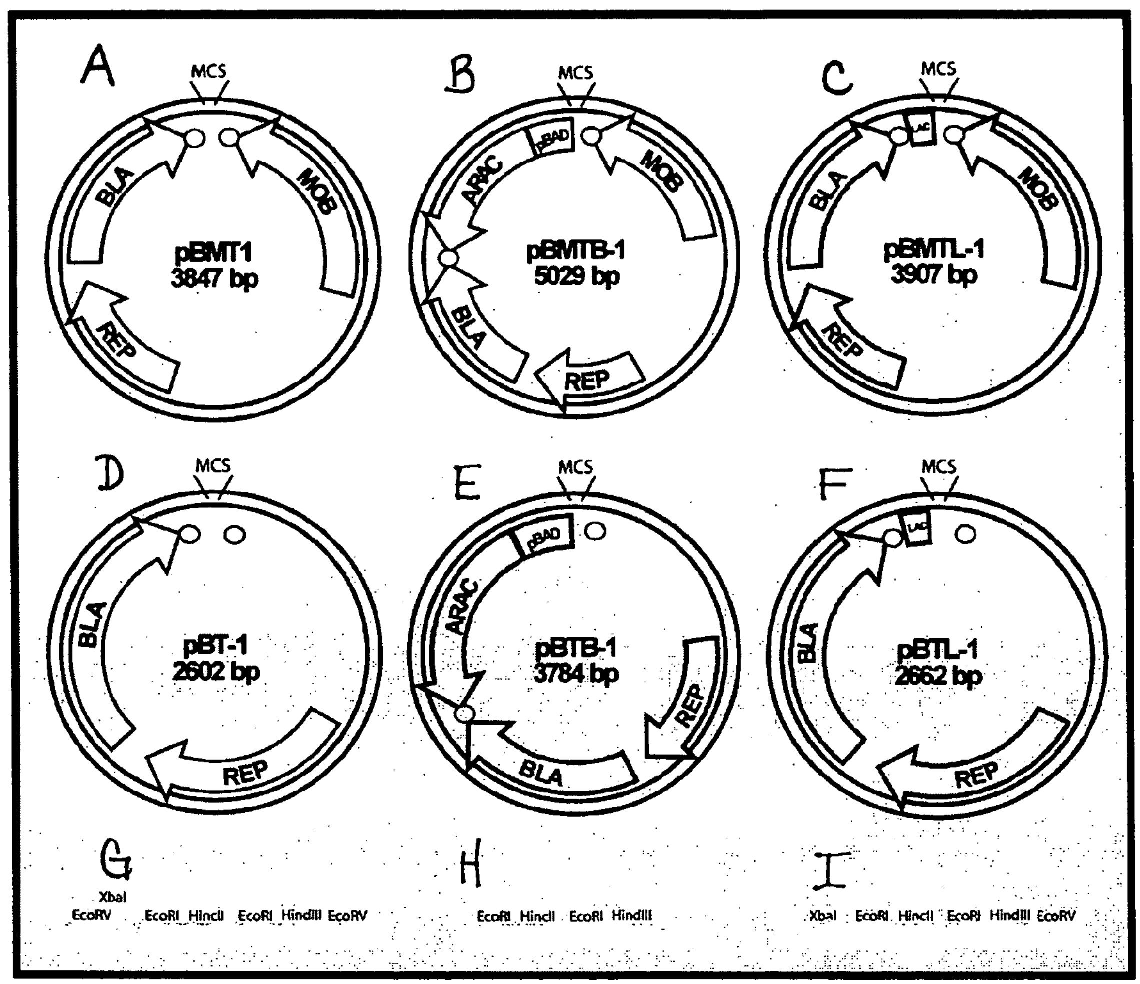

FIG. 2. represents six exemplary vectors with β-lactamase cassettes.

DESCRIPTION OF ILLUSTRATIVE EMBODIMENTS

Definitions

As used herein, "a" or "an" may mean one or more than one of an item.

DESCRIPTION

In the following sections, various exemplary compositions and methods are described in order to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

In some embodiments, compositions of the present invention include designing and using vectors. In one particular embodiment, the present invention involves the design of plasmid vectors for use in a broad range of Gram negative bacteria. In accordance with these compositions, to be useful in various bacterial species, such vectors must include a broad host range replicon a variety of options for controlling transcription via constitutive, inducible, or native promoters. Alternatively, the native promoters may rely on genomic ribosomal binding sites and start codons, and a range of antibiotic resistance genes. One advantage of these vectors includes creating stable vectors for producing extra-chromosomal genomic libraries.

Vectors for such library creation should include strong bi-directional, host-factor independent transcriptional terminators around the multiple cloning site, as well as a single origin of replication to promote plasmid stability.

One example of stable cloning vectors are a series of vectors offered commercially from Lucigen called CloneSmart (Middleton, Wis.). These vectors are specifically designed for library creation, propagation and sequencing in *Escherichia coli*. The increased stability and, as a consequence, increased library representation of these vectors is largely due to strong transcriptional terminators that flank the cloning region. The strong prokaryotic terminators are derived from either the T3 bacteriophage or bidirectional tonB terminators. These terminators isolate insert RNA polymerase activity required for expression of cloned gene products from the DNA/RNA polymerase activity required for plasmid maintenance and replication, which is thought to increase plasmid stability. It has been shown that genomic libraries constructed in these vectors are highly representational and allow for the cloning of toxic genetic elements as well as sequences containing strong promoters.

One disadvantage of the CloneSmart vectors is that they are limited to use in *E. coli*. Further, various issues exist with respect to toxicity and/or instability of present vectors available for use with Gram negative bacteria other than *E. coli*.

In one embodiment, the present invention relates to methods and compositions that include a series of novel broad host range vectors for library construction. In certain embodiments, vectors disclosed herein may include a bidirectional terminator. In addition, the vectors may include a replicon from the broad host range plasmid pBBR1, the pBAD, pLac, or no heterologous promoter. In another embodiment, resistance cassettes may be positioned within a vector for β-lactams, kanamycin, chloramphenicol, tetracycline, trimethoprim, and tellurite (see Table II). The skilled artisan will realize that other replicons, promoters, and selectable or screenable marker genes, such as other antibiotic resistance genes, may be used in the claimed methods and compositions.

In another embodiment, a mobilizable version of each vector may also be created. The pBBR1 replicon has been demonstrated to stably replicate in every Gram negative species in which it has been tested to date. It is contemplated herein that any other replicon region that is of use in a broad range of Gram negative host bacteria is also of use in embodiments disclosed in the present invention. Also, the pLac and pBAD promoters have also been demonstrated to allow for gene expression in a broad range of Gram negative species. The vectors reported herein allow for the creation and screening or selection of highly representative and stable genomic libraries in a broad range of Gram negative bacteria. A mobilizable version of a vector of the present invention may be generated by introducing a mobilization function and an origin of transfer, that can be active when used in a cell line expressing transfer functions such as those transfer functions, not limited to, but permitted by the RP4 plasmid. One potential use for a vector having a mobilization function may be to transfer a vector to new host strains through conjugation. (Transfer functions allow for conjugation of the vectors, RP4 is the prototypical transfer function, there are other strains in addition there are also numerous mobilization functions that could be included in the vectors (transfer functions are not in the vector but in the host cell, mobilization functions are in the vector), such as those supplied by the IncP and IncQ plasmid groups.

In one example, motivation for creating these stable libraries stems from efforts to construct and screen representational and stable genomic plasmid based libraries, in which there can be a high frequency of structural plasmid instability. For example, pUC based plasmids even when carried in recombination deficient hosts can often be unstable. Several possible mechanisms exist to explain this instability, the importance of each may vary with any given insert sequence. The vectors reported herein have been designed to address each of these possible sources of instability.

For example, the presence of a ribosome binding site and start codon upstream of the multiple cloning site (MCS) can result in the expression of a toxic gene product, which can either be a natural protein or a fusion of the LacZα gene, used for blue/white screening, with any in-frame sequence. In one embodiment, to reduce or eliminate the possibility of expression of such unnatural toxic products, the vectors disclosed herein rely on insert ribosomal binding sites and start codons for expression. Insert ribosomal binding sites are ribosomal binding sites that are in the genomic DNA that is inserted into these vectors.

Alternatively, to reduce or eliminate low-level expression of non-native gene products that might exert a toxic effect on host physiology, the disclosed vectors contain a variety of promoters that allow for generating libraries specific to the cell line under study and the intended screening application. Typically, these problems are due to the presence of a leaky promoter, such as pLac, flanking the cloning site or read-through transcription of the RNA polymerase initiated on plasmid encoded genes. To reduce the occurrence of these problems, three types of vectors have been constructed (see Table 2): the first type has no promoter and therefore relies upon native promoters for gene expression; the second type uses the pBAD promoter which consists of the araB promoter and araC gene, which relies upon a metabolite, arabinose, for induction, and the third type uses the Lac promoter, which is induced by low levels of lactose analogs.

Finally, plasmid stability is influenced by the effects that insert sequences can have on plasmid replication and maintenance functions. The cloning of strong promoters as well as other AT-rich sequences can influence the RNA and DNA polymerase activities required for plasmid maintenance and replication. In one embodiment of the present invention, a vector construct can be generated by flanking the cloning regions of the vector with bidirectional transcriptional terminators. Using this strategy, insert-driven transcription into the vector backbone, as well as read through transcription from the backbone into the insert can be reduced and possibly eliminated. This technique provides greater insert stability in vectors. In one embodiment, strong, bidirectional transcriptional terminators can be used. In accordance with this embodiment, one important consideration is the use of rho-independent and likely host-factor independent terminators. In one example, the transcriptional terminators following the tonB and soxR genes in the *E. coli* genome can be used. The tonB The tonB terminator is currently used in the CloneSmart vectors and is factor independent. However, the CloneSmart vectors also utilize the terminator from T3 bacteriophage, which is dependent on host-factors for efficient termination. In another embodiment, the T3 bacteriophage terminator can be replaced with the terminator from the *E. coli* soxR gene to extend the use of the vectors across different Gram negative species.

In addition to the effects of insert DNA on plasmid stability, structural and segregational instability in shuttle vectors containing multiple replicons has been observed when carried in recombination proficient hosts. This could be due to a combination of the above mentioned effects including read-through transcription. This could also be due to the competition or interference of a partially active replicon with the primary replicon in a given host. Expression and DNA binding of replication and copy number controlling proteins, including Rep proteins, are likely to interfere with each other as well as appropriate replication, maintenance and segregation. In one embodiment, in order to bypass possible instability caused by multiple replicons, a single broad-host-range replicon can be used in a construct. In accordance with this embodiment, one exemplary replicon from the pBBR1 plasmid isolated from *Bordetella bronchiseptica*, has a medium copy number (~30 copies/cell), and, as far as it has been tested, a host range including all Gram negative species. Additionally, it has even been shown to be stable in the absence of antibiotic pressure and also has a unique incompatibility group. As a result, vectors with this origin may be used alongside other plasmids in the same host.

In some embodiments of the invention, the disclosed plasmids can contain a variety of expression options, as well as, selectable elements such as antibiotic resistance cassettes. In addition, a version of each plasmid that is mobilizable when supplemented with RP4 transfer functions, should enable use in hosts where conjugation may be more efficient than transformation. These vectors are of use for the construction of highly representational genomic libraries of Gram negative organisms, which can then be utilized in genetic screens and selections not only in the organism of the library's origin but also in other Gram negative hosts. In addition, the vectors disclosed herein having transfer functions are of use in expression systems.

In one embodiment, the vectors of the present invention may be used to generate a stable genomic library for screening of, or the selection performed on genomic libraries to identify phenotypic functions for genes or genetic elements. In a more specific embodiment, genomic libraries combined with screening and selection methods can be used to identify genes or genetic elements (including but not limited to operons, regulatory regions such as operators or activators and sRNAs) that can confer a phenotype of interest or usefulness to a host cell. These phenotypes can include but are not limited to natural phenotypes. In accordance with these embodiments, a genomic libraries can aid in basic understanding of biology, as well as more applied phenotypes useful in engineering host cells to perform useful functions. For example, induce or increase production of useful products, be able to metabolize different nutrient sources in order to make useful products from different raw materials, have more useful growth characteristics for industrial process such as temperature or pH. Examples of useful products include but are not limited to ethanol, lactate, succinate and 3-hydroxypropionate.

Nucleic Acids

As described herein, an aspect of the present disclosure concerns isolated nucleic acids and methods of use of isolated nucleic acids. In certain embodiments, the nucleic acid sequences disclosed herein have utility as hybridization probes or amplification primers. These nucleic acids may be used, for example, in diagnostic evaluation of tissue samples. In certain embodiments, these probes and primers consist of oligonucleotide fragments. Such fragments should be of sufficient length to provide specific hybridization to a RNA or DNA tissue sample. The sequences typically will be 10-20 nucleotides, but may be longer. Longer sequences, e.g., 40, 50, 100, 500 and even up to full length, are preferred for certain embodiments.

Nucleic acid molecules having contiguous stretches of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75 80, 85, 90, 95, 100, 125, 150, 175, 200, 250, 300, 400, 500, 600, 750, 1000, 1500, 2000, 2500 or more nucleotides from a sequence selected from the disclosed nucleic acid sequences are contemplated. Molecules that are complementary to the above mentioned sequences and that bind to these sequences under high stringency conditions also are contemplated. These probes will be useful in a variety of hybridization embodiments, such as Southern and Northern blotting.

The use of a hybridization probe of between 14 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one may desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific MRNA transcripts. It is generally appreciated that conditions can be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 μM $MgCl_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known which can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

It will be understood that this invention is not limited to the particular probes disclosed herein and particularly is intended to encompass at least nucleic acid sequences that are hybridizable to the disclosed sequences or are functional sequence analogs of these sequences. For example, a partial sequence may be used to identify a structurally-related gene or the full length genomic or cDNA clone from which it is derived. Those of skill in the art are well aware of the methods for generating cDNA and genomic libraries which can be used as a target for the above-described probes (Sambrook et al., 1989).

For applications in which the nucleic acid segments of the present invention are incorporated into vectors, such as plasmids disclosed herein, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

Where an expression product is to be generated, it is possible for the nucleic acid sequence to be varied while retaining the ability to encode the same product. Reference to the codon chart, provided above, will permit those of skill in the art to design any nucleic acid encoding for the product of a given nucleic acid.

Plasmid Preparations

Plasmid preparations and replication means are well known in the art. See for example, U.S. Pat. Nos. 4,273,875 and 4,567,146 incorporated herein their entirety. Some embodiments of the present invention include providing a portion of genetic material of a target microorganism and inserting the portion of genetic material of a target microorganism into a plasmid for use as an internal control plasmid.

Amplification

Embodiments of the present invention include providing conditions that facilitate amplification of at least a portion of a target genetic material. However, it should be appreciated that the amplification conditions of embodiments of the present invention are not necessarily 100% specific.

The embodiments of the present invention include any method for amplifying at least a portion of a microorganism's genetic material (such as Polymerase Chain Reaction (PCR), Real-time PCR (RT-PCR), NASBA (nucleic acid sequence based amplification)). In one embodiment, Real time PCR (RT-PCR) can be a method for amplifying at least a portion of a target microorganism's genetic material while simultaneously amplifying an internal control plasmid for verification of the outcome of the amplification of a microorganism's genetic material.

While the scope of the present invention includes any method (for example, Polymerase Chain Reaction, i.e., PCR, and nucleic acid sequence based amplification, i.e., NASBA) for amplifying at least a portion of the microorganism's genetic material, for one example, the present invention describes embodiments in reference to PCR technique.

Amplification of a genetic material, e.g., DNA, is well known in the art. See, for example, U.S. Pat. Nos. 4,683,202, and 4,994,370, which are incorporated herein by reference in their entirety. Methods of the present invention include providing conditions that would allow co-amplification of an internal control plasmid's portion of a microorganism's genetic material and a portion of the microorganism's genetic material of a test sample, if the target microorganism is present in the sample and the conditions for the method support the amplification of the internal control plasmid. In this manner, detection of the amplification products by a specific probe for each product of the internal control plasmid's portion of a microorganism's genetic material and a portion of the microorganism's genetic material is indicative of the presence of the microorganism in the sample and that the conditions for the amplification are working. Thus, a negative result indicative of absence of a target microorganism can be confirmed.

Typically, to verify the working conditions of PCR techniques, positive and negative external controls are performed in parallel reactions to the sample tubes to test the reaction conditions, for example using a control nucleic acid sequence for amplification. In some embodiments of the present invention, an internal control can be used to determine if the conditions of the RT-PCR reaction is working in a specific tube for a specific target sample. Alternatively, in some embodiments of the present invention, an internal control can be used to determine if the conditions of the RT-PCR reaction are working in a specific tube at a specific time for a specific target microorganism sample. For example, an internal control in an RT-PCR reaction can be used to determine whether lack of detection of a target microorganism in a given sample is truly negative or a false negative. In this manner, lack of detection of an amplification product of a portion of a target microorganism's genetic material is indicative of the absence of the microorganism in the sample and this is confirmed when the internal control (such as an internal plasmid control) is amplified in the same reaction tube at the same time indicating the conditions were conducive for amplification.

By knowing the nucleotide sequences of the genetic material in a target microorganism and in an internal control, specific primer sequences can be designed. In one embodiment of the present invention, at least one primer of a primer pair used to amplify a portion of genomic material of a target microorganism is in common with one of the primers of a primer pair used to amplify a portion of genetic material of an internal control such as an internal control plasmid. In one embodiment of the present invention, the primer is about, but not limited to 5 to 50 oligonucleotides long, or preferably about 10 to 40 oligonucleotides long or more preferably about 10 to 30 oligonucleotides long. Suitable primer sequences can be readily synthesized by one skilled in the art or are readily available from third party providers such as BRL (New England Biolabs), etc. Other reagents, such as DNA polymerases and nucleotides, that are necessary for a nucleic acid sequence amplification such as PCR are also commercially available.

Detection

The presence or absence of PCR amplification product can be detected by any of the techniques known to one skilled in the art. In one particular embodiment, methods of the present invention include detecting the presence or absence of the PCR amplification product using a probe that hybridizes to a particular genetic material of the microorganism. By designing the PCR primer sequence and the probe nucleotide sequence to hybridize different portions of the microorganism's genetic material, one can increase the accuracy and/or sensitivity of the methods disclosed herein.

While there are a variety of labelled probes available, such as radioactive and fluorescent labelled probes, in one particular embodiment, methods of the present invention use a fluorescence resonance energy transfer (FRET) labeled probe as internal hybridization probes. In one particular embodiment of the present invention, an internal hybridization probe is included in the PCR reaction mixture so that product detection occurs as the PCR amplification product is formed, thereby reducing post-PCR processing time. Roche Lightcycler PCR instrument (U.S. Pat. No. 6,174,670) or other real-time PCR instruments can be used in this embodiment of the invention, e.g., see U.S. Pat. No. 6,814,934. PCR amplification of a genetic material increases the sensitivity of methods of the present invention to $10^1$ organisms or less in comparison to about $10^5$ microorganisms that are required in standard ELISA methods. In some instances, real-time PCR amplification and detection significantly reduce the total assay time so that test results may be obtained in about 12 hours. Accordingly, methods of the present invention provide rapid and/or highly accurate results relative to the conventional methods and these results are verified by an internal control.

Nucleic Acid Amplification

Nucleic acids used as a template for amplification is isolated from cells contained in the biological sample, according to standard methodologies. (Sambrook et al., 1989) The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification.

Pairs of primers that selectively hybridize to nucleic acids corresponding to specific markers are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintilography of incorporated radiolabel or fluorescent label or even via a system using electrical or thermal impulse signals (Affymax technology; Bellus, 1994).

Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred.

Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art. Other amplification methods are known in the art besides PCR such as LCR (ligase chain reaction), disclosed in European Application No. 320 308, incorporated herein by reference in its entirety.

In another embodiment, Qbeta Replicase, previously described, may also be used as still another amplification method in the present invention. In this method, a replicative sequence of RNA which has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention. Walker et al., *Proc. Nat'l Acad. Sci. USA* 89:392-396 (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences may also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Still other amplification methods known in the art may be used with the methods described herein.

Davey et al., European Application No. 329 822 (incorporated herein by reference in its entirely) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("ds-DNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., *Genomics* 4:560 (1989), incorporated herein by reference in its entirety.

Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In one embodiment, detection is by Southern blotting and hybridization with a labeled probe. The techniques involved in Southern blotting are well known to those of skill in the art and may be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

In general, prokaryotes used for cloning DNA sequences in constructing the vectors useful in the invention include for example, any gram negative bacteris such as *E. coli* strain K12. Other microbial strains which may be used include *P. aeruginosa* strain PAO1, and *E. coli* B strain. These examples are illustrative rather than limiting. Other example bacterial hosts for constructing a library include but are not limited to *Aeromonas, Acetobacter, Agrobacterium, Alcaligenes, Azorizobium, Bartonella, Bordetella, Brucella, Burkholderia, Caulobacter, Escherichia, Erwinia, Hyphomicrobium, Methylobacillus, Methybacterium, Mehylophilus, Pseudomonus, Paracoccus, Rhizobium, Ralstonia, Rhodobacter, Salmonella, Vibrio* and *Xanthomonas.*

Prokaryotic cells also can be used for expression. The aforementioned strains, as well as *E. coli* W3110 (F.sup.-, .lamda..sup.-, prototrophic, ATTC No. 27325), and other enterobacteriaceae such as *Salmonella typhimurium* or *Serratia marcescans*, and various *pseudomonas* species can be used.

In general, plasmid vectors containing promoters and control sequences which are derived from species compatible with the host cell are used with these hosts. The vector ordinarily carries a replication site as well as one or more marker sequences which are capable of providing phenotypic selection in transformed cells. For example, a PBBR1 replicon region which is useful in many Gram negative bacterial strains or any other replicon region that is of use in a broad range of Gram negative host bacteria can be used in the present invention.

Promoters suitable for use with prokaryotic hosts illustratively include the beta.-lactamase and lactose promoter systems (Chang et al., "Nature", 275: 615 [1978]; and Goeddel et al., "Nature" 21: 544 [1979]), alkaline phosphatase, the tryptophan (trp) promoter system (Goeddel "Nucleic Acids Res." 8: 4057 [1980] and EPO Appln. Publ. No. 36,776) and hybrid promoters such as the tac promoter (H. de Boer et al., "Proc. Natl. Acad. Sci. USA" 80: 21 25 [1983]). However, other functional bacterial promoters are suitable.

In another embodiment, expression vectors used in prokaryotic host cells may also contain sequences necessary for efficient translation of specific genes encoding specific mRNA sequences that can be expressed from any suitable promoter. This would necessitate incorporation of a promoter followed by ribosomal binding sites or a Shine-Dalgarno (S.D.) sequence operably linked to the DNA encoding the mRNA.

Construction of suitable vectors containing the desired coding and control sequences employ standard ligation techniques. Isolated plasmids or DNA fragments are cleaved, tailored, and religated in the form desired to form the plasmids required.

For analysis to confirm correct sequences in plasmids constructed, the ligation mixtures are used to transform a bacteria strain such as *E. coli* K12 and successful transformants selected by antibiotic resistance such as tetracycline where appropriate. Plasmids from the transformants are prepared, analyzed by restriction and/or sequenced.

Host cells can be transformed with expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

"Transformation" refers to the taking up of an expression vector by a host cell whether or not any coding sequences are in fact expressed. Numerous methods of transfection are known to the ordinarily skilled artisan, for example, Ca salts.sub.4 and electroporation. Successful transformation is generally recognized when any indication of the operation of this vector occurs within the host cell.

In order to facilitate understanding of the following examples certain frequently occurring methods and/or terms will be described.

Digestion of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37 .degree. C. are ordinarily used, but may vary in accordance with the supplier's instructions. After digestion the reaction is electrophoresed directly on a polyacrylamide gel to isolate the desired fragment.

Recovery or isolation of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally (Lawn, R. et al., Nucleic Acids Res. 9: 6103 6114 [1981], and Goeddel, D. et al., Nucleic Acids Res. 8: 4057 [1980]).

Dephosphorylation refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional (Maniatis, T. et al., Molecular Cloning, 133 134 Cold Spring Harbor, [1982]). Reactions using BAP are carried out in 50 mM Tris at 68 .degree. C. to suppress the activity of any exonucleases which may be present in the enzyme preparations. Reactions are run for 1 hour. Following the reaction the DNA fragment is gel purified.

Ligation refers to the process of forming phosphodiester bonds between two double stranded nucleic acid fragments (Maniatis, T. et al., Id. at 146). Unless otherwise provided, ligation may be accomplished using known buffers and conditions with 10 units of T4 DNA ligase ("ligase") per 0.5 .mu.g of approximately equimolar amounts of the DNA fragments to be ligated.

Filling or blunting refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. In one embodiment, blunting is accomplished by incubating around 2 to 20 μg of the target DNA in 10 mM MgCl.sub.2, 1 mM dithiothreitol, 50 mM NaCl, 10 mM Tris (pH 7.5) buffer at about 37 .degree. C. in the presence of 8 units of the Klenow fragment of DNA polymerase I and 250 μM of each of the four deoxynucleoside triphosphates. The incubation generally is terminated after 30 min. phenol and chloroform extraction and ethanol precipitation As used interchangeably herein, the terms "nucleic acid molecule(s)", "oligonucleotide(s)", and "polynucleotide(s)" include RNA or DNA (either single or double stranded, coding, complementary or antisense), or RNA/DNA hybrid sequences of more than one nucleotide in either single chain or duplex form (although each of the above species may be particularly specified). The term "nucleotide" is used herein as an adjective to describe molecules comprising RNA, DNA, or RNA/DNA hybrid sequences of any length in single-stranded or duplex form. More precisely, the expression "nucleotide sequence" encompasses the nucleic material itself and is thus not restricted to the sequence information (i.e. the succession of letters chosen among the four base letters) that biochemically characterizes a specific DNA or RNA molecule. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modifications such as (a) an alternative linking group, (b) an analogous form of purine, (c) an analogous form of pyrimidine, or (d) an analogous sugar. For examples of analogous linking groups, purine, pyrimidines, and sugars see for example PCT publication No. WO 95/04064, which disclosure is hereby incorporated by reference in its entirety. Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyaceticacid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine. The polynucleotide sequences of the invention may be prepared by any known method, including synthetic, recombinant, ex vivo generation, or a combination thereof, as well as utilizing any purification methods known in the art. Methylenemethylimino linked oligonucleosides as well as mixed backbone compounds, may be prepared as described in U.S. Pat. Nos. 5,378,825; 5,386,023; 5,489,677; 5,602,240; and 5,610,289, which disclosures are hereby incorporated by reference in their entireties. Formacetal and thioformacetal linked oligonucleosides may be prepared as described in U.S. Pat. Nos. 5,264,562 and 5,264,564, which disclosures are hereby incorporated by reference in their entireties. Ethylene oxide linked oligonucleosides may be prepared as described in U.S. Pat. No. 5,223,618, which disclosure is hereby incorporated by reference in its entirety. Phosphinate oligonucleotides may be prepared as described in U.S. Pat. No. 5,508,270, which disclosure is hereby incorporated by reference in its entirety. Alkyl phosphonate oligonucleotides may be prepared as described in U.S. Pat. No. 4,469,863, which disclosure is hereby incorporated by reference in its entirety. 3'-Deoxy-3'-methylene phosphonate oligonucleotides may be prepared as described in U.S. Pat. Nos. 5,610,289 or 5,625,050 which disclosures are hereby incorporated by reference in their entireties. Phosphoramidite oligonucleotides may be prepared as described in U.S. Pat. Nos. 5,256,775 or 5,366,878 which disclosures are hereby incorporated by reference in their entireties. Alkylphosphonothioate oligonucleotides may be prepared as described in published PCT applications WO 94/17093 and WO 94/02499 which disclosures are hereby incorporated by reference in their entireties. 3'-Deoxy-3'-amino phosphoramidate oligonucleotides may be prepared as described in U.S. Pat. No. 5,476,925, which disclosure is hereby incorporated by reference in its entirety. Phosphotriester oligonucleotides may be prepared as described in U.S. Pat. No. 5,023,243, which disclosure is hereby incorporated by reference in its entirety. Borano phosphate oligonucleotides may be prepared as described in U.S. Pat. Nos. 5,130,302 and 5,177,198 which disclosures are hereby incorporated by reference in their entireties.

The term "upstream" is used herein to refer to a location which is toward the 5' end of the polynucleotide from a specific reference point.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Stryer, 1995, which disclosure is hereby incorporated by reference in its entirety).

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind. Unless otherwise stated, all complementary polynucleotides are fully complementary on the whole length of the considered polynucleotide.

The terms "polypeptide" and "protein", used interchangeably herein, refer to a polymer of amino acids without regard to the length of the polymer; thus, peptides, oligopeptides, and proteins are included within the definition of polypeptide. This term also does not specify or exclude chemical or post-expression modifications of the polypeptides of the invention, although chemical or post-expression modifications of these polypeptides may be included excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance Creighton (1993); Seifter et al., (1990); Rattan et al., (1992)). Also included within the definition are polypeptides which contain one or more analogs of an amino acid (including, for example, non-naturally occurring amino acids, amino acids which only occur naturally in an unrelated biological system, modified amino acids from mammalian systems, etc.), polypeptides with substituted linkages, as well as other modifications known in the art, both naturally occurring and non-naturally occurring.

As used herein, the terms “recombinant polynucleotide” and “polynucleotide construct” are used interchangeably to refer to linear or circular, purified or isolated polynucleotides that have been artificially designed and which comprise at least two nucleotide sequences that are not found as contiguous nucleotide sequences in their initial natural environment. In particular, these terms mean that the polynucleotide or cDNA is adjacent to “backbone” nucleic acid to which it is not adjacent in its natural environment. Additionally, to be “enriched” the cDNAs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched cDNAs represent 15% or more of the number of nucleic acid inserts in the population of recombinant backbone molecules. More preferably, the enriched cDNAs represent 50% or more of the number of nucleic acid inserts in the population of recombinant backbone molecules. In a highly preferred embodiment, the enriched cDNAs represent 90% or more (including any number between 90 and 100%, to the thousandth position, e.g., 99.5%) # of the number of nucleic acid inserts in the population of recombinant backbone molecules.

The term “recombinant polypeptide” is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

As used herein, the term “operably linked” refers to a linkage of polynucleotide elements in a functional relationship. A sequence which is “operably linked” to a regulatory sequence such as a promoter means that said regulatory element is in the correct location and orientation in relation to the nucleic acid to control RNA polymerase initiation and expression of the nucleic acid of interest. For instance, a promoter or enhancer is operably linked to a coding sequence if it affects the transcription of the coding sequence.

In a specific embodiment, the polynucleotides of the invention are at least 15, 30, 50, 100, 125, 500, or 1000 continuous nucleotides. In another embodiment, the polynucleotides are less than or equal to 300 kb, 200 kb, 100 kb, 50 kb, 10 kb, 7.5 kb, 5 kb, 2.5 kb, 2 kb, 1.5 kb, or 1 kb in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 75, 50, 25, 20, 15, 10, 5, 4, 3, 2, or 1 naturally occurring genomic flanking gene(s).

Procedures used to detect the presence of nucleic acids capable of hybridizing to the detectable probe include well known techniques such as Southern blotting, Northern blotting, dot blotting, colony hybridization, and plaque hybridization. In some applications, the nucleic acid capable of hybridizing to the labeled probe may be cloned into vectors such as expression vectors, sequencing vectors, or in vitro transcription vectors to facilitate the characterization and expression of the hybridizing nucleic acids in the sample. For example, such techniques may be used to isolate and clone sequences in a genomic library or cDNA library which are capable of hybridizing to the detectable probe as described herein.

Labels

Certain embodiments may involve incorporating a label into a probe, primer and/or target nucleic acid to facilitate its detection by a detection unit. A number of different labels may be used, such as Raman tags, fluorophores, chromophores, radioisotopes, enzymatic tags, antibodies, chemiluminescent, electroluminescent, affinity labels, etc. One of skill in the art will recognize that these and other label moieties not mentioned herein can be used in the disclosed methods.

Fluorescent labels of use may include, but are not limited to, Alexa 350, Alexa 430, AMCA (7-amino-4-methylcoumarin-3-acetic acid), BODIPY (5,7-dimethyl-4-bora-3a,4a-diaza-s-indacene-3-propionic acid) 630/650, BODIPY 650/665, BODIPY-FL (fluorescein), BODIPY-R6G (6-carboxyrhodamine), BODIPY-TMR (tetramethylrhodamine), BODIPY-TRX (Texas Red-X), Cascade Blue, Cy2 (cyanine), Cy3, Cy5,6-FAM (5-carboxyfluorescein), Fluorescein, 6-JOE (2'7'-dimethoxy-4'5'-dichloro-6-carboxyfluorescein), Oregon Green 488, Oregon Green 500, Oregon Green 514, Pacific Blue, Rhodamine Green, Rhodamine Red, ROX (6-carboxy-X-rhodamine), TAMRA (N,N,N',N'-tetramethyl-6-carboxyrhodamine), Tetramethylrhodamine, and Texas Red. Fluorescent or luminescent labels can be obtained from standard commercial sources, such as Molecular Probes (Eugene, Oreg.).

Examples of enzymatic labels include urease, alkaline phosphatase or peroxidase. Colorimetric indicator substrates can be employed with such enzymes to provide a detection means visible to the human eye or spectrophotometrically. Radioisotopes of potential use include $^{14}$carbon, $^{3}$hydrogen, $^{125}$iodine, $^{32}$phosphorus and $^{35}$sulphur.

Vectors for Gene Expression

In certain embodiments expression vectors are employed to assay the functional effects of certain sequences such as a bi-directional, host-factor independent transcriptional terminators sequence. Expression requires that appropriate signals be provided in the vectors, and which include various regulatory elements, such as enhancers/promoters from viral or mammalian sources that drive expression of the genes of interest in host cells. Bi-directional, host-factor independent transcriptional terminators elements may be incorporated into the expression vector and levels of transcription, translation, RNA stability or protein stability may be determined using standard techniques known in the art. The effect of the bi-directional, host-factor independent transcriptional terminators sequence may be determined by comparison to a control expression vector lacking the bi-directional, host-factor independent transcriptional terminators sequence, or to an expression vector containing a bi-directional, host-factor independent transcriptional terminators sequence of known effect.

Regulatory Elements

The terms "expression construct" or "expression vector" are meant to include any type of genetic construct containing a nucleic acid coding for a gene product in which part or all of the nucleic acid coding sequence is capable of being transcribed. In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. The particular promoter employed to control the expression of a nucleic acid sequence of interest is not believed to be important, so long as it is capable of directing the expression of the nucleic acid in the targeted cell.

Where a cDNA insert is employed, typically one will typically include a polyadenylation signal to effect proper polyadenylation of the gene transcript. The nature of the polyadenylation signal is not believed to be crucial to the successful practice of the invention, and any such sequence may be employed. Also contemplated as an element of the expression construct is a terminator. These elements can serve to enhance message levels and to minimize read through from the construct into other sequences.

Reporter Genes

In certain embodiments of the invention, the expression construct will contain a reporter gene whose activity may be measured to determine the effect of a bi-directional, host-factor independent transcriptional terminators element or other element. Conveniently, the reporter gene produces a product that is easily assayed, such as a colored product, a fluorescent product or a luminescent product. Many examples of reporter genes are available, such as the genes encoding GFP (green fluorescent protein), CAT (chloramphenicol acetyltransferase), luciferase, GAL (β-galactosidase), GUS (β-glucuronidase), etc. The reporter gene employed is not believed to be important, so long as it is capable of being expressed and its level of expression may be assayed. Further examples of reporter genes are well known to one of skill in the art, and any such known gene may be used in the practice of the claimed methods.

Kits

In some embodiments, the present invention concerns kits for use with the methods described herein. The kits may comprise, in suitable container means, one or more vectors, each vector capable of being used in a broad range of Gram negative bacteria. In various embodiments, such kits may contain additional components of use for the amplification, hybridization and/or detection of vector sequences and or inserts, which components may include but not limited to two or more amplification primers, buffer, nucleotides, labels (such as fluorescent labels), labeled primers, polymerase, enzymes, enzyme substrates, control probes, control amplification templates, molecular weight standards or any other kit component known in the art.

The kits may further include a suitably aliquoted composition of the probes and/or primers, whether labeled or unlabeled, as may be used to prepare a standard curve for a detection assay. The components of the kits may be packaged either in aqueous media or in lyophilized form.

The container means of the kits will generally include at least one vial, test tube, flask, bottle, syringe or other container means, into which the probes and/or primers may be placed, and preferably, suitably aliquoted. Where an additional component is provided, the kit will also generally contain additional containers into which this component may be placed. The kits of the present invention will also typically include a means for containing the probes, primers, and any other reagent containers in close confinement for commercial sale. Such containers may include injection or blow-molded plastic containers into which the desired vials are retained.

The embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

EXAMPLES

Material and Methods

Media

In one exemplary method cultures were grown in Luria-Bertani (LB) broth or on LB agar plates according to standard protocols. Antibiotic concentrations were: carbencillin: 100 μg/mL, kanamycin: 25 μg/mL, chloramphenicol: 100 μg/mL, tetracycline: 5 μg/mL, trimethoprim: 200 μg/mL and potassium tellurite: 50 μg/mL. Antibiotics were obtained from Research Products International (Mt. Prospect, Ill.) and potassium tellurite from Alfa Aesar (Ward Hill, Mass.). For blue/white screening 40 μg/mL 5-Bromo-4-Chloro-3-Idolyβ-D-Galactopyranoside (Xgal) (Sigma-Aldrich, St. Louis, Mo.) was added to plates.

Molecular Cloning

In another exemplary method, restriction endonucleases, antarctic phosphatase, and T4 polymerase obtained from for example, New England Biolabs (Beverly, Mass.), were used. Reagents for polymerase chain reaction using the proofreading Pfx polymerase as well as T4 polynucleotide kinase were obtained from Invitrogen (Carlsbad, Calif.). Primers and oligos listed in Table I were ordered from Operon (Huntsville, Ala.). Enzymes were used according to manufacturer instructions. Ligations and transformations were carried out using the UltraClone™ kit from Lucigen (Middleton, Wis.) with E. Cloni$^{R}$10 G electrocompetent cells (F-mcrA D(mrr-hsdRMS-mcrBC) f80dlacZDM15 DlacX74 endA1 recA1araD139 D(ara, leu)7697 galU galK rpsL nupG 1-tonA). All DNA sequencing was performed by Macrogen (Seoul, Korea). Construction of plasmids and genomic libraries are described below under "Results".

Example 1

Vector Construction

In one exemplary objective a series of broad-host range vectors suitable for the creation and evaluation of highly representational genomic libraries in Gram negative bacteria are generated. The construction of exemplary vectors, pBMT-1 and pBT-1, are depicted in FIG. 1. First, plasmid pBBR1-Tp-MCS (ATCC #87448) was digested with the enzyme SmaI and treated with antarctic phosphatase. The blunt ended, dephophorylated fragment was ligated to a blunt fragment containing the TonB and T3 bacteriophage transcriptional terminators from pSMART-HC-AMP (Lucigen, Cat#40041), obtained by DpnI digestion. After ligation, transformants were selected on LB plus trimethoprim supplemented with Xgal. A white clone with the proper insert orientation was picked and termed pBBR1-Tp-Term. This plasmid was subsequently digested with BamHI and NgoMIV and then treated with T4 polymerase and antarctic phosphatase. The large blunt fragment was ligated to the β-lactamase gene from pSMART-HC-AMP that had been isolated by an ApaI and BsaAI digestion and treatment with T4 polymerase. Transformations were plated on LB plus trimethoprim and carbenicillin. The new β-lactam resistant vector was named pBBR1-Tp-Term-Bla. In order to remove excess sequence and insert the SoxR terminator in place of the bacteriophage T3 terminator, pBBR1-Tp-Term-Bla was subjected to two polymerase chain reactions using Pfx polymerase. The first reaction used the following primers: RepR (SEQ ID NO:38) and Mob_R (SEQ ID NO:37). The second reaction used primers SoxRT_SL1(SEQ ID NO:40) and AmpF (SEQ ID NO:39). The two resulting PCR products were treated with T4 kinase and ligated to create pBMT-1 (SEQ ID NO:1). The nonmobilizable vector pBT-1 (SEQ ID NO:7) was constructed by digesting pBMT-1 with BsrBI and ligating.

In addition to the exemplary vectors pBMT-1 and pBT-1, four other exemplary vectors containing either the pBAD or pLac promoter were constructed, pBMTB-1 (SEQ ID NO:13), pBMTL-1 (SEQ ID NO:25), pBTB-1 (SEQ ID NO:19) and pBTL-1 (SEQ ID NO:30). To construct pBTB-1, SwaI-digested and dephophorylated pBT-1 was ligated to the araB promoter and araC gene from pBAD24 (ATCC #87399) that had been amplified with the pBAD_F (SEQ ID NO:45) and pBAD_R primers (SEQ ID NO:46) and phosphorylated with T4 polynucleotide kinase. The resulting plasmid with correct orientation, pBTBE-1, was created, containing both a ribosomal binding site and start codon. These were removed by a double digest with the enzymes NheI and XbaI followed by a ligation to create pBTB-1. pBTB-1 and pBMT-1 were both digested with SnaBI and HindIII, and the appropriate fragments of each ligated to create pBMTB-1. pBTL-1 was constructed in a similar fashion. SwaI digested and dephosphorylated pBT-1 was ligated to the Lac promoter and LacZa gene from pEZSeq-HCKan (Lucigen, Cat #40500) that had been amplified with the Lac_F (SEQ ID NO:41) and Lac_R (SEQ ID NO:42) primers. The ribosomal binding site and LacZα gene were removed from the resulting plasmid pBT-Lac by digesting with BsrBI and XbaI and ligating to the annealed dimer of oligonucleotides LacReplace1 (SEQ ID NO:43) and LacReplace2 (SEQ ID NO:44). The resulting plasmid was named pBTL-1. As in the case of pBMTB-1, pBMTL-1 was constructed by ligating the correct pieces of SnaBI and HindIII digested pBTL-1 and pBMT-1. The maps of these β-lactam resistant vectors are provided in FIG. 2.

The details of the exemplary vectors depicted in FIG. 1 are as follows: exemplary constructs of pBMT-1 and pBT-1. A) The terminators, indicated by circles, from a DpnI digest of pSMART-HC-AMP were inserted into SmaI digested pBBR1-Tp-MCS to create pBBR-Tp-Term. B) The β-lactamase gene obtained from a BsaAI and ApaI digest of pSMART-HC-AMP was inserted into NgoMIV and BamHI digested pBBR1-Tp-Term to construct pBBR1-Tp-Term-Bla. Both pieces were treated with T4 polymerase prior to ligation. Two fragments of pBBR1-Tp-Term were amplified by PCR. The first PCR directed at the fragment containing the mob and rep genes (C), employed the Mob_R (SEQ ID NO:37) and Rep_R (SEQ ID NO:38) primers. The second PCR against the fragment containing the multiple cloning site, tonB terminator and β-lactamase used the Amp_F (SEQ ID NO:39) and SoxRT-SL1 (SEQ ID NO:40) primers. The SoxRT_SL1(SEQ ID NO:40) primer sequence includes the SoxR terminator. These two fragments were ligated to construct pBMT-1. D) pBMT-1 was digested with BsrBI to remove the mob gene and create pBT-1.

The details of the exemplary vectors depicted in FIG. 2 are as follows: three vectors, A, B and C, carry the mob gene and are mobilizable with RP4 transfer functions in trans. Vector pBMT-1 (A) has no inducible promoter, vectors pBMTB-1 (B) and pBMTL-1 (B) carry an inducible pBAD promoter and pLAC promoter, respectively. The remaining three vectors pBT-1 (D), pBTB-1 (E) and pBTL-1 (F) are not mobilizable, and like their counterparts are promoterless, or carry the pBAD and pLAC promoters respectively. In all cases the positions of the two rho-independent, bidirectional transcriptional terminators are indicated by circles. G) The multiple cloning site for the pBMTB and pBTB series of vectors. H) The multiple cloning site for the pBMT and pBT series of vectors. I) The multiple cloning site for the pBMTL and pBTL series of vectors. Note: some of the restriction sites may cut within the antibiotic resistance cassettes for any specific vector.

Thirty counterpart vectors were also constructed, six each, with kanamycin, (pBT-2 (SEQ ID NO:8), pBTB-2 (SEQ ID NO:20), pBTL-2 (SEQ ID NO:32), pBMT-2 (SEQ ID NO:2), pBMTB-2 (SEQ ID NO:14), pBMTL-2 (SEQ ID NO:26)), chloramphenicol (pBT-3 (SEQ ID NO:9), pBTB-3 (SEQ ID NO:21), pBTL-3 (SEQ ID NO:33), pBMT-3 (SEQ ID NO:3), pBMTB-3 (SEQ ID NO: 15), pBMTL-3 (SEQ ID NO:27)), tetracycline (pBT-4 (SEQ ID NO: 10), pBTB-4 (SEQ ID NO:22), pBTL-4 (SEQ ID NO:34), pBMT-4 (SEQ ID NO:4), pBMTB-4 (SEQ ID NO: 16), pBMTL-4 (SEQ ID NO:28)), trimethoprim (pBT-5 (SEQ ID NO:1), pBTB-5 (SEQ ID NO:23), pBTL-5 (SEQ ID NO:35), pBMT-5 (SEQ ID NO:5), pBMTB-5 (SEQ ID NO:17), pBMTL-5 (SEQ ID NO:29)) and tellurite (pBT-6 (SEQ ID NO:12), pBTB-6 (SEQ ID NO:24), pBTL-6 (SEQ ID NO:36), pBMT-6 (SEQ ID NO:6), pBMTB-6 (SEQ ID NO:18), pBMTL-6 (SEQ ID NO:30)) resistance cassettes. The chloramphenicol acetyl-transferase gene (cat) was obtained from a BamHI and Bpu10I digest of the Gateway Vector Conversion Kit Reading Frame Cassette A (Invitrogen). The kanamycin kinase gene (kan) was obtained from a PCR of pEZSeq-HCKan with the Kan_F (SEQ ID NO:47) and Kan_R (SEQ ID NO:48) primers. The dihydrofolate reductase gene (dhfr) was obtained from a PCR of pBBR1-Tp-MCS using the Tmp_F (SEQ ID NO:51) and Tmp_R(SEQ ID NO:52) primers. The tetracycline resistance gene (tetA) from plasmid pBR322 (New England Biolabs) was obtained from a PCR using the Tet_F (SEQ ID NO:49) and Tet_R (SEQ ID NO:50) primers. The tellurite resistance genes, kilA, telA and telB from plasmid pJPS10 were obtained from a PCR using the Tell_F (SEQ ID NO:53) and Tell_R (SEQ ID NO:54) primers. The cat gene was ligated into pBMT-1, that had been digested with Bpu10I and BamHI, to create pBMT-3. Plasmid pBT-3 was constructed by removing the mob gene from pBMT-3 by a BsrBI digest. The other resistance cassettes isolated by polymerase chain reaction, were treated with T4 kinase and ligated with the blunt fragment of pBMT-1 amplified by a polymerase chain reaction, using the RC__1 (SEQ ID NO:55) and RC__2 (SEQ ID NO:56) primers, to construct pBMT-2, pBMT-4, pBMT-5 and pBMT-6. The skilled artisan will realize that alternative selectable marker genes may be obtained from sources well known in the art, such as the American Type Culture Collection (Rockville, Md.) or known commercial vendors (e.g., Promega, Stratagene, etc.)

These vectors created above, except for pBMT-6, were each digested with BsrBI and self-ligated to obtain pBT-2, pBT-4 and pBT-5 respectively. The resistance cassettes for kanamycin, chloramphenicol, tetracycline, trimethoprim and tellurite are capable of isolation from these vectors by a SnaBI and BamHI digest. (In the case of the tetracycline resistance gene this creates two pieces due to an internal BamHI recognition site). The vectors with these resistance cassettes and thepBAD or pLac promoters were constructed similarly to their □-lactamase counterparts, or by exchanging antibiotic cassettes among vectors, which was how pBT-6 was constructed.

Confirmation of Sequence and Function

The six β-lactam resistance vectors pBT-1, pBTB-1, pBTL-1, pBMT-1, pBMTB-1, pBMTL-1 were sequenced for confirmation of cloning. Full sequences of each vector are available from GenBank with accession numbers as indicated in Table 2. As further confirmation, the pBT-1 and pBTB-1 vectors were used to create several genomic libraries of the *P. aeruginosa* laboratory strain PAO1, a clinical isolate of *P. aeruginosa*, and the *Escherichia coli* strain K12. Genomic insert DNA of approximately 4000 bp, or 6000 bp in the case of the clinical isolate, was prepared by a partial digest with two enzymes: RsaI and HaeIII (Invitrogen) in the case of PAO1 and the clinical isolate of *Pseudomonas*, and RsaI and AluI (Invitrogen), in the case of K12, followed by size separation by agarose gel electrophoresis and purification using a Gel Extraction kit (Qiagen, Valencia, Calif.). Dephosphorylated vector DNA was generated by a PCR of each vector using the proofreading polymerase, Pfx. The primers used in the case of the pBT-1 vector were pBT_Lib1 (SEQ ID NO:57) and pBT_Lib2 (SEQ ID NO:58), and the primers used for the pBTB-1 vector were pBT_Lib1 (SEQ ID NO:57) and pBTB_Lib2 (SEQ ID NO:59). Blunt ended products were ligated to insert DNA and transformed. After transformation, in each case we obtained greater than $10^5$ colonies with an insert, which corresponds to greater than 99% probability that the entire genome is represented.

FIG. 1. represents an exemplary plasmid construct of pBMT-1 and pBT-1 . A) The terminators, indicated by circles, from a DpnI digest of pSMART-HC-AMP were inserted into SmaI digested pBBR1-Tp-MCS to create pBBR-Tp-Term. B) The β-lactamase gene obtained from a BsaAI and ApaI digest of pSMART-HC-AMP was inserted into NgoMIV and BamHI digested pBBR1-Tp-Term to construct pBBR1-Tp-Term-Bla. Both pieces were treated with T4 polymerase prior to ligation. C) Two fragments of pBBR1-Tp-Term-Bla were amplified by PCR. The first PCR directed at the fragment containing the mob and rep genes, employed the Mob_R (SEQ ID NO:37) and Rep_R (SEQ ID NO:38) primers. The second PCR against the fragment containing the multiple cloning site, tonB terminator and β-lactamase used the Amp_F (SEQ ID NO:39) and SoxRT-SL1 (SEQ ID NO:40) primers. The SoxRT_SL1 (SEQ ID NO:40) primer sequence includes the SoxR terminator. These two fragments were ligated to construct pBMT-1. D) pBMT-1 was digested with BsrBI to remove the mob gene and create pBT-1.

FIG. 2. represents six exemplary vectors with β-lactamase cassettes. Three vectors, a, b and c, carry the mob gene and are mobilizable with RP4 transfer functions in trans. Vector pBMT-1 (a) has no inducible promoter, vectors pBMTB-1 (b) and pBMTL-1 (c) carry an inducible pBAD promoter and pLAC promoter, respectively. The remaining three vectors pBT-1 (d), pBTB-1 (e) and pBTL-1 (f) are not mobilizable, and like their counterparts are promoterless, or carry the pBAD and pLAC promoters respectively. In all cases the positions of the two rho-independent, bidirectional transcriptional terminators are indicated by circles. g) The multiple cloning site for the pBMTB and pBTB series of vectors. h) The multiple cloning site for the pBMT and pBT series of vectors. i) The multiple cloning site for the pBMTL and pBTL series of vectors. Note: some of the restriction sites may cut within the antibiotic resistance cassettes for any specific vector.

Described herein, a series of broad-host range vectors suitable for the creation and evaluation of highly representational genomic libraries in Gram negative bacteria were generated. The motivation for creating such libraries stems from efforts to construct and screen representational and stable genomic plasmid based libraries, in which a large frequency of structural plasmid instability in pUC based plasmids even when carried in recombination deficient hosts (unpublished results). Several possible mechanisms exist to explain this instability, the importance of each of which may vary with any given insert sequence. The exemplary vectors described here have been designed to address each of such possible sources of instability.

The exemplary plasmid vectors have a variety of expression options as well as antibiotic resistance cassettes. In addition, a version of each plasmid that is mobilizable when supplemented with RP4 transfer functions has been developed, which enables use in hosts where conjugation may be more efficient than transformation. These vectors also contain minimal amounts of unnecessary DNA sequence minimizing recombination events in vivo. In certain embodiments, these vectors may contain the arabinose inducible pBAD promoter for controlled induction of cloned DNA. This promoter has been shown to have activity in many different gram negative species. The exemplary vectors are of use for the construction of highly representational genomic libraries of Gram negative organisms, which may then be utilized in genetic screens and selections not only in the organism of the library's origin but also in other Gram negative hosts.

The disclosed vectors allow for the cloning of individual genes as well as for library construction. Since they replicate in easily manipulated *E. coli* hosts as well as in all other Gram negative bacteria, they allow for the creation of libraries and clones in *E. coli* using optimized cloning methods followed by transfer to other Gram negative species. This should greatly simplify the screening of libraries from all Gram negative sources within these sources themselves. This would eradicate the need to construct Gram negative shuttle vectors, which often contain multiple origins of replication and inherent instabilities.

TABLE 1

Primers used in plasmid construction.

| Primer | Sequence |
|---|---|
| Mob_R | 5'-CGCTCATGATAATAATGGTTTCTTAGACGTC-3'<br>SEQ ID NO: 37 |
| Rep_R | 5'-CTACCGGCGCGGCAGCGTGACCC-3'<br>SEQ ID NO: 38 |
| Amp_F | 5'-TACGTAAGAGGTTCCAACTTTCACCAT-<br>AATGAAATA<br>AG-3'<br>SEQ ID NO: 39 |
| SoxRT_SL1 | 5'-AACAAAACTAAAGCGCCA-<br>CAAGGGCGCTTTAGTTTG<br>TTTTCAGTCCAGTTACGCTGGAGTC-3'<br>SEQ ID NO: 40 |

TABLE 1-continued

Primers used in plasmid construction.

| Primer | Sequence |
|---|---|
| Lac_F | 5'-TGCATTAGGCACCCCAGGC-3' SEQ ID NO: 41 |
| Lac_R | 5'-AAATTTATTAGCGCCATTCGCC-3' SEQ ID NO: 42 |
| LacReplace1 | 5'-CGGATAACAATTTCACACT-3' SEQ ID NO: 43 |
| LacReplace2 | 5'-CTAGAGTGTGAAATTGTTATCCG-3' SEQ ID NO: 44 |
| pBAD_F | 5'-TTATGACAACTTGACGGCTACATCATTC-3' SEQ ID NO: 45 |
| pBAD_R | 5'-GTACCATGGTGAATTCCTCCTGCTAG-3' SEQ ID NO: 46 |
| Kan_F | 5'-GGAAGCTAAAATGAGCCATATTCAACGG-3' SEQ ID NO: 47 |
| Kan_R | 5'-GCCCTCAGAAAAACTCATCGA-3' SEQ ID NO: 48 |
| Tet_F | 5'-GGAAGCTAAAATGAAATCTAACAATGCG-3' SEQ ID NO: 49 |
| Tet_R | 5'-CTTCCATTCAGGTCGAGG-3' SEQ ID NO: 50 |
| Tmp_F | 5'-GGAAGCTAAAATGGGTCAAAGTAGCGAT-3' SEQ ID NO: 51 |
| Tmp_R | 5'-ATTCTTAGGCCACACGTTCAAG-3' SEQ ID NO: 52 |
| Tell_F | 5'-GGAAGCTAAAATGGAAGAACAA-3' SEQ ID NO: 53 |
| Tell_R | 5'-CTTATGGCTCTGCACCCGGCTC-3' SEQ ID NO: 54 |
| RC_1 | 5'-GGATCCCCCTCAAGTCAAAAGC-3' SEQ ID NO: 55 |
| RC_2 | 5'-TTAGCTCCTGAAAATCTCGATAACTCAA-3' SEQ ID NO: 56 |
| pBT_Lib1 | 5'-GATATCATTCAGGACGAGCCTCAGACTCCA-3' SEQ ID NO: 57 |
| pBT_Lib2 | 5'-GATATCGCTCAATACTGACCATTTAAAT-CATACCTG ACCTCC-3' SEQ ID NO: 58 |
| pBTB_Lib2 | 5'-CTCTAGCCCAAAAAAACGGGTATG-GAGAAACAGTAG AGAG-3' SEQ ID NO: 59 |

TABLE 2

Broad host range vectors for stable genomic library creation.

| Name | Resistance | Promoter | Mobi-lizable | GenBank Accession Number AND SEQ. ID NO: 1 |
|---|---|---|---|---|
| pBMT-1 | β-lactams | None | yes | DQ058714/SEQ. ID NO: 1 |
| pBMT-2 | kanamycin | None | yes | DQ058715/SEQ. ID NO: 2 |
| pBMT-3 | chloramphenicol | None | yes | DQ058716/SEQ. ID NO: 3 |
| pBMT-4 | tetracycline | None | yes | DQ058717/SEQ. ID NO: 4 |
| pBMT-5 | trimethoprim | None | yes | DQ058718/SEQ. ID NO: 5 |
| pBMT-6 | tellurite | None | yes | DQ091274/SEQ. ID NO: 6 |
| pBT-1 | β-lactams | None | no | DQ058719/SEQ. ID NO: 7 |
| pBT-2 | kanamycin | None | no | DQ058720/SEQ. ID NO: 8 |
| pBT-3 | chloramphenicol | None | no | DQ058721/SEQ. ID NO: 9 |
| pBT-4 | tetracycline | None | no | DQ058722/SEQ. ID NO: 10 |
| pBT-5 | trimethoprim | None | no | DQ058723/SEQ. ID NO: 11 |
| pBT-6 | tellurite | None | no | DQ091275/SEQ. ID NO: 12 |
| pBMTB-1 | β-lactams | pBAD | yes | DQ058724/SEQ. ID NO: 13 |
| pBMTB-2 | kanamycin | pBAD | yes | DQ058725/SEQ. ID NO: 14 |
| pBMTB-3 | chloramphenicol | pBAD | yes | DQ058726/SEQ. ID NO: 15 |
| pBMTB-4 | tetracycline | pBAD | yes | DQ058727/SEQ. ID NO: 16 |
| pBMTB-5 | trimethoprim | pBAD | yes | DQ058728/SEQ. ID NO: 17 |
| pBMTB-6 | tellurite | pBAD | yes | DQ091276/SEQ. ID NO: 18 |
| pBTB-1 | β-lactams | pBAD | no | DQ058729/SEQ. ID NO: 19 |
| pBTB-2 | kanamycin | pBAD | no | DQ058730/SEQ. ID NO: 20 |
| pBTB-3 | chloramphenicol | pBAD | no | DQ058731/SEQ. ID NO: 21 |
| pBTB-4 | tetracycline | pBAD | no | DQ058732/SEQ. ID NO: 22 |
| pBTB-5 | trimethoprim | pBAD | no | DQ058733/SEQ. ID NO: 23 |
| pBTB-6 | tellurite | pBAD | no | DQ091277/SEQ. ID NO: 24 |
| pBMTL-1 | β-lactams | pLac | yes | DQ058734/SEQ. ID NO: 25 |
| pBMTL-2 | kanamycin | pLac | yes | DQ058735/SEQ. ID NO: 26 |
| pBMTL-3 | chloramphenicol | pLac | yes | DQ058736/SEQ. ID NO: 27 |
| pBMTL-4 | tetracycline | pLac | yes | DQ058737/SEQ. ID NO: 28 |
| pBMTL-5 | trimethoprim | pLac | yes | DQ058738/SEQ. ID NO: 29 |
| pBMTL-6 | tellurite | pLac | yes | DQ091278/SEQ. ID NO: 30 |
| pBTL-1 | β-lactams | pLac | no | DQ058739/SEQ. ID NO: 31 |
| pBTL-2 | kanamycin | pLac | no | DQ058740/SEQ. ID NO: 32 |
| pBTL-3 | chloramphenicol | pLac | no | DQ058741 SEQ. ID NO: 33 |
| pBTL-4 | tetracycline | pLac | no | DQ058742/SEQ. ID NO: 34 |
| pBTL-5 | trimethoprim | pLac | no | DQ058743/SEQ. ID NO: 35 |
| pBTL-6 | tellurite | pLac | no | DQ091279/SEQ. ID NO: 36 |

All of the COMPOSITIONS and/or METHODS and/or APPARATUS disclosed and claimed herein can be made and executed without undue experimentation in light of the present disclosure. While the compositions and methods of this invention have been described in terms of preferred embodiments, it will be apparent to those of skill in the art that variation may be applied to the COMPOSITIONS and/or METHODS and/or APPARATUS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A composition comprising a vector of use in a broad range of Gram negative host bacteria, wherein the vector comprises:

a) a multiple cloning site having a bi-directional, host-factor independent transcriptional terminator on each side of the multiple cloning site;

b) a selectable marker region; and c) a replicon region from a pBBR1 plasmid.

2. The composition of claim 1, wherein the vector is a plasmid.

3. The composition of claim 2, wherein the vector comprises a single origin of replication.

4. The composition of claim 1, further comprising a promoter.

5. The composition of claim 1, wherein the selectable marker region is selected from the group consisting of an antibiotic resistance gene, one or more genes conferring growth on a nutrient source not normally utilized by a strain, one or more genes conferring a pH-selection, and one or more genes conferring a temperature-selection.

6. The composition of claim 4, wherein the promoter is pBAD or pLac.

7. The composition of claim 5, wherein the antibiotic resistance gene is selected from the group consisting of resistance cassettes for β-lactams, kanamycin, chloramphenicol, tetracycline, trimethoprim and tellurite.

8. The composition of claim 1, further comprising a promoter between one said transcriptional terminator and said multiple cloning site.

9. The composition of claim 1, wherein the transcriptional terminator on one said side of the multiple cloning site is a tonB transcriptional terminator and the transcriptional terminator on the other said side is a soxR transcriptional terminator.

10. The composition of claim 2, wherein the plasmid is mobilizable.

11. The composition of claim 10, wherein mobilization is facilitated by supplementation of the plasmid with RP4.

12. A method of use for a vector in a broad range of Gram negative host bacteria comprising:

a) generating a vector comprising i) a multiple cloning site having a bi-directional, host-factor independent transcriptional terminator on each side of the multiple cloning site; ii) a selectable marker region; and iii) a replicon region from a pBBR1 plasmid; and b) constructing a genomic library using the vector.

13. The method of claim 12, further comprising replicating the genomic library in a Gram negative host bacteria species.

14. The method of claim 13, wherein the Gram negative host bacteria species is selected from the group consisting of *Acetobacter, Agrobacterium, Alcaligenes, Azorizobium, Bartonella, Bordetella, Brucella, Burkholderia, Caulobacter, Escherichia, Erwinia, Hyphomicrobium, Methylobacillus, Methybacterium, Mehylophilus, Pseudomonas, Paracoccus, Rhizobium, Ralstonia, Rhodobacter, Salmonella, Vibrio, Xanthomonas*, and *Zymomonas*.

15. The method of claim 12, further comprising adding a pLac or a pBad promoter region to the vector.

16. The method of claim 12, wherein constructing a genomic library using the vector comprises constructing a stable genomic library with or without constitutive expression.

17. A method of use for a vector in a broad range of Gram negative host bacteria comprising:

a) generating a vector comprising i) a multiple cloning site having a bi-directional, host-factor independent transcriptional terminator on each side of the multiple cloning site; ii) a selectable marker region; iii) a replicon region from a pBBR1 plasmid; and iv) a promoter between one said transcriptional terminator and said multiple cloning site; and b) expressing a genomic library using the vector.

18. The method of claim 17, further comprising using the genomic library to identify a phenotypic function of a gene.

19. The composition of claim 1, wherein the Gram negative host bacteria is selected from the group consisting of *Acetobacter, Agrobacterium, Alcaligenes, Azorizobium, Bartonella, Bordetella, Brucella, Burkholderia, Caulobacter, Escherichia, Erwinia, Hyphomicrobium, Methylobacillus, Methybacterium, Mehylophilus, Pseudomonas, Paracoccus, Rhizobium, Ralstonia, Rhodobacter, Salmonella, Vibrio, Xanthomonas*, and *Zymomonas*.

* * * * *

SEQUENCE LISTING

<160> NUMBER OF SEQ ID NOS: 59

<210> SEQ ID NO 1
<211> LENGTH: 3847
<212> TYPE: DNA
<213> ORGANISM: Escherichia coli

<400> SEQUENCE: 1
aacgaattca agcttgatat cattcaggac gagcctcaga ctccagcgta actggactga 60
aaacaaacta aagcgccctt gtggcgcttt agttttgttc cgctcatgat aataatggtt 120
tcttagacgt caggtggcac ttttcgggga aatgtgcgcg cccgcgttcc tgctggcgct 180
gggcctgttt ctggcgctgg acttcccgct gttccgtcag cagcttttcg cccacggcct 240
tgatgatcgc ggcggccttg gcctgcatat cccgattcaa cggccccagg gcgtccagaa 300
cgggcttcag gcgctcccga aggtctcggg ccgtctcttg ggcttgatcg gccttcttgc 360
gcatctcacg cgctcctgcg gcggcctgta gggcaggctc atacccctgc cgaaccgctt 420
ttgtcagccg gtcggccacg gcttccggcg tctcaacgcg ctttgagatt cccagctttt 480
cggccaatcc ctgcggtgca taggcgcgtg gctcgaccgc ttgcgggctg atggtgacgt 540
ggcccactgg tggccgctcc agggcctcgt agaacgcctg aatgcgcgtg tgacgtgcct 600
tgctgccctc gatgccccgt tgcagcccta gatcggccac agcggccgca aacgtggtct 660
ggtcgcgggt catctgcgct ttgttgccga tgaactcctt ggccgacagc ctgccgtcct 720
gcgtcagcgg caccacgaac gcggtcatgt gcgggctggt ttcgtcacgg tggatgctgg 780
ccgtcacgat gcgatccgcc ccgtacttgt ccgccagcca cttgtgcgcc ttctcgaaga 840
acgccgcctg ctgttcttgg ctggccgact tccaccattc cgggctggcc gtcatgacgt 900
actcgaccgc caacacagcg tccttgcgcc gcttctctgg cagcaactcg cgcagtcggc 960
ccatcgcttc atcggtgctg ctggccgccc agtgctcgtt ctctggcgtc ctgctggcgt 1020
cagcgttggg cgtctcgcgc tcgcggtagg cgtgcttgag actggccgcc acgttgccca 1080
ttttcgccag cttcttgcat cgcatgatcg cgtatgccgc catgcctgcc cctccctttt 1140
ggtgtccaac cggctcgacg ggggcagcgc aaggcggtgc ctccggcggg ccactcaatg 1200
cttgagtata ctcactagac tttgcttcgc aaagtcgtga ccgcctacgg cggctgcggc 1260
gccctacggg cttgctctcc gggcttcgcc ctgcgcggtc gctgcgctcc cttgccagcc 1320
cgtggatatg tggacgatgg ccgcgagcgg ccaccggctg gctcgcttcg ctcggcccgt 1380
ggacaaccct gctggacaag ctgatggaca ggctgcgcct gcccacgagc ttgaccacag 1440
ggattgccca ccggctaccc agccttcgac cacataccca ccggctccaa ctgcgcggcc 1500
tgcggccttg ccccatcaat ttttttaatt ttctctgggg aaaagcctcc ggcctgcggc 1560
ctgcgcgctt cgcttgccgg ttggacacca agtggaaggc gggtcaaggc tcgcgcagcg 1620
accgcgcagc ggcttggcct tgacgcgcct ggaacgaccc aagcctatgc gagtgggggc 1680
agtcgaaggc gaagcccgcc cgcctgcccc ccgagcctca cggcggcgag tgcgggggtt 1740

```
ccaagggggc agcgccacct tgggcaaggc cgaaggccgc gcagtcgatc aacaagcccc   1800

ggaggggcca ctttttgccg gagggggagc cgcgccgaag gcgtggggga accccgcagg   1860

ggtgcccttc tttgggcacc aaagaactag atatagggcg aaatgcgaaa gacttaaaaa   1920

tcaacaactt aaaaaagggg ggtacgcaac agctcattgc ggcacccccc gcaatagctc   1980

attgcgtagg ttaaagaaaa tctgtaattg actgccactt ttacgcaacg cataattgtt   2040

gtcgcgctgc cgaaaagttg cagctgattg cgcatggtgc cgcaaccgtg cggcacccta   2100

ccgcatggag ataagcatgg ccacgcagtc cagagaaatc ggcattcaag ccaagaacaa   2160

gcccggtcac tgggtgcaaa cggaacgcaa agcgcatgag gcgtgggccg ggcttattgc   2220

gaggaaaccc acggcggcaa tgctgctgca tcacctcgtg gcgcagatgg gccaccagaa   2280

cgccgtggtg gtcagccaga agacactttc caagctcatc ggacgttctt tgcggacggt   2340

ccaatacgca gtcaaggact tggtggccga gcgctggatc tccgtcgtga agctcaacgg   2400

ccccggcacc gtgtcggcct acgtggtcaa tgaccgcgtg gcgtggggcc agccccgcga   2460

ccagttgcgc ctgtcggtgt tcagtgccgc cgtggtggtt gatcacgacg accaggacga   2520

atcgctgttg gggcatggcg acctgcgccg catcccgacc ctgtatccgg gcgagcagca   2580

actaccgacc ggccccggcg aggagccgcc cagccagccc ggcattccgg gcatggaacc   2640

agacctgcca gccttgaccg aaacggagga atgggaacgg cgcgggcagc agcgcctgcc   2700

gatgcccgat gagccgtgtt ttctggacga tggcgagccg ttggagccgc cgacacgggt   2760

cacgctgccg cgccggtagt acgtaagagg ttccaacttt caccataatg aaataagatc   2820

actaccgggc gtattttttg agttatcgag attttcagga gctaaggaag ctaaaatgag   2880

tattcaacat ttccgtgtcg cccttattcc cttttttgcg gcattttgcc ttcctgtttt   2940

tgctcaccca gaaacgctgg tgaaagtaaa agatgctgaa gatcagttgg gtgcacgagt   3000

gggttacatc gaactggatc tcaacagcgg taagatcctt gagagtttac gccccgaaga   3060

acgttttcca atgatgagca cttttaaagt tctgctatgt ggcgcggtat tatcccgtat   3120

tgacgccggg caagagcaac tcggtcgccg catacactat tctcagaatg acttggttga   3180

gtactcacca gtcacagaaa agcatctcac ggatggcatg acagtaagag aattatgcag   3240

tgctgccata accatgagtg ataacactgc ggccaactta cttctggcaa cgatcggagg   3300

accgaaggag ctaaccgctt ttttgcacaa catgggggat catgtaactc gccttgatcg   3360

ttgggaaccg gagctgaatg aagccatacc aaacgacgag cgtgacacca cgatgcctgt   3420

agcaatggca acaacgttgc gcaaactatt aactggcgaa ctacttactc tagcttcccg   3480

gcaacaatta atagactgga tggaggcgga taaagttgca ggatcacttc tgcgctcggc   3540

cctcccggct ggctggttta ttgctgataa atctggagcc ggtgagcgtg ggtctcgcgg   3600

tatcattgca gcactggggc cagatggtaa gccctcccgc atcgtagtta tctacacgac   3660

ggggagtcag gcaactatgg atgaacgaaa tagacagatc gctgagatag gtgcctcact   3720

gattaagcat tggtaatgag gatccccctc aagtcaaaag cctccggtcg gaggcttttg   3780

actttctgct atggaggtca ggtatgattt aaatggtcag tattgagcga tatctagaga   3840

attcgtc                                                             3847
```

<210> SEQ ID NO 2
<211> LENGTH: 3803
<212> TYPE: DNA
<213> ORGANISM: Escherichia coli

<400> SEQUENCE: 2

```
aacgaattca agcttgatat cattcaggac gagcctcaga ctccagcgta actggactga      60
aaacaaacta aagcgccctt gtggcgcttt agttttgttc cgctcatgat aataatggtt     120
tcttagacgt caggtggcac ttttcgggga aatgtgcgcg cccgcgttcc tgctggcgct     180
gggcctgttt ctggcgctgg acttcccgct gttccgtcag cagcttttcg cccacggcct     240
tgatgatcgc ggcggccttg gcctgcatat cccgattcaa cggccccagg gcgtccagaa     300
cgggcttcag gcgctcccga aggtctcggg ccgtctcttg ggcttgatcg gccttcttgc     360
gcatctcacg cgctcctgcg gcggcctgta gggcaggctc atacccctgc cgaaccgctt     420
ttgtcagccg gtcggccacg gcttccggcg tctcaacgcg ctttgagatt cccagctttt     480
cggccaatcc ctgcggtgca taggcgcgtg gctcgaccgc ttgcgggctg atggtgacgt     540
ggcccactgg tggccgctcc agggcctcgt agaacgcctg aatgcgcgtg tgacgtgcct     600
tgctgccctc gatgccccgt tgcagcccta gatcggccac agcggccgca aacgtggtct     660
ggtcgcgggt catctgcgct ttgttgccga tgaactcctt ggccgacagc ctgccgtcct     720
gcgtcagcgg caccacgaac gcggtcatgt gcgggctggt ttcgtcacgg tggatgctgg     780
ccgtcacgat gcgatccgcc ccgtacttgt ccgccagcca cttgtgcgcc ttctcgaaga     840
acgccgcctg ctgttcttgg ctggccgact tccaccattc cgggctggcc gtcatgacgt     900
actcgaccgc caacacagcg tccttgcgcc gcttctctgg cagcaactcg cgcagtcggc     960
ccatcgcttc atcggtgctg ctggccgccc agtgctcgtt ctctggcgtc ctgctggcgt    1020
cagcgttggg cgtctcgcgc tcgcggtagg cgtgcttgag actggccgcc acgttgccca    1080
ttttcgccag cttcttgcat cgcatgatcg cgtatgccgc catgcctgcc cctccctttt    1140
ggtgtccaac cggctcgacg gggcagcgc aaggcggtgc ctccggcggg ccactcaatg     1200
cttgagtata ctcactagac tttgcttcgc aaagtcgtga ccgcctacgg cggctgcggc    1260
gccctacggg cttgctctcc gggcttcgcc ctgcgcggtc gctgcgctcc cttgccagcc    1320
cgtggatatg tggacgatgg ccgcgagcgg ccaccggctg gctcgcttcg ctcggcccgt    1380
ggacaaccct gctggacaag ctgatggaca ggctgcgcct gcccacgagc ttgaccacag    1440
ggattgccca ccggctaccc agccttcgac cacataccca ccggctccaa ctgcgcggcc    1500
tgcggccttg ccccatcaat ttttttaatt ttctctgggg aaaagcctcc ggcctgcggc    1560
ctgcgcgctt cgcttgccgg ttggacacca agtggaaggc gggtcaaggc tcgcgcagcg    1620
accgcgcagc ggcttggcct tgacgcgcct ggaacgaccc aagcctatgc gagtgggggc    1680
agtcgaaggc gaagcccgcc cgcctgcccc ccgagcctca cggcggcgag tgcgggggtt    1740
ccaaggggc agcgccacct tgggcaaggc cgaaggccgc gcagtcgatc aacaagcccc     1800
ggaggggcca ctttttgccg gagggggagc cgcgccgaag gcgtggggga accccgcagg    1860
ggtgcccttc tttgggcacc aaagaactag atatagggcg aaatgcgaaa gacttaaaaa    1920
tcaacaactt aaaaaagggg ggtacgcaac agctcattgc ggcacccccc gcaatagctc    1980
attgcgtagg ttaaagaaaa tctgtaattg actgccactt ttacgcaacg cataattgtt    2040
gtcgcgctgc cgaaaagttg cagctgattg cgcatggtgc cgcaaccgtg cggcacccta    2100
ccgcatggag ataagcatgg ccacgcagtc cagagaaatc ggcattcaag ccaagaacaa    2160
gcccggtcac tgggtgcaaa cggaacgcaa agcgcatgag gcgtgggccg ggcttattgc    2220
gaggaaaccc acggcggcaa tgctgctgca tcacctcgtg gcgcagatgg gccaccagaa    2280
cgccgtggtg gtcagccaga agacactttc caagctcatc ggacgttctt tgcggacggt    2340
```

-continued

```
ccaatacgca gtcaaggact tggtggccga gcgctggatc tccgtcgtga agctcaacgg   2400

ccccggcacc gtgtcggcct acgtggtcaa tgaccgcgtg gcgtggggcc agccccgcga   2460

ccagttgcgc ctgtcggtgt tcagtgccgc cgtggtggtt gatcacgacg accaggacga   2520

atcgctgttg gggcatggcg acctgcgccg catcccgacc ctgtatccgg gcgagcagca   2580

actaccgacc ggccccggcg aggagccgcc cagccagccc ggcattccgg gcatggaacc   2640

agacctgcca gccttgaccg aaacggagga atgggaacgg cgcgggcagc agcgcctgcc   2700

gatgcccgat gagccgtgtt ttctggacga tggcgagccg ttggagccgc cgacacgggt   2760

cacgctgccg cgccggtagt acgtaagagg ttccaacttt caccataatg aaataagatc   2820

actaccgggc gtattttttg agttatcgag attttcagga gctaaggaag ctaaaatgag   2880

ccatattcaa cgggaaacgt cttgctcgag gccgcgatta aattccaaca tggatgctga   2940

tttatatggg tataaatggg ctcgcgataa tgtcgggcaa tcaggtgcga caatctatcg   3000

attgtatggg aagcccgatg cgccagagtt gtttctgaaa catggcaaag gtagcgttgc   3060

caatgatgtt acagatgaga tggtcaggct aaactggctg acggaattta tgcctcttcc   3120

gaccatcaag cattttatcc gtactcctga tgatgcatgg ttactcacca ctgcgatccc   3180

agggaaaaca gcattccagg tattagaaga atatcctgat tcaggtgaaa atattgttga   3240

tgcgctggca gtgttcctgc gccggttgca ttcgattcct gtttgtaatt gtccttttaa   3300

cggcgatcgc gtatttcgtc tcgctcaggc gcaatcacga atgaataacg gtttggttgg   3360

tgcgagtgat tttgatgacg agcgtaatgg ctggcctgtt gaacaagtct ggaaagaaat   3420

gcataagctt ttgccattct caccggattc agtcgtcact catggtgatt tctcacttga   3480

taaccttatt tttgacgagg ggaaattaat aggttgtatt gatgttggac gagtcggaat   3540

cgcagaccga taccaggatc ttgccatcct atggaactgc ctcggtgagt tttctccttc   3600

attacagaaa cggctttttc aaaaatatgg tattgataat cctgatatga ataaattgca   3660

gtttcacttg atgctcgatg agtttttctg agggcggatc cccctcaagt caaaagcctc   3720

cggtcggagg cttttgactt tctgctatgg aggtcaggta tgatttaaat ggtcagtatt   3780

gagcgatatc tagagaattc gtc                                             3803
```

<210> SEQ ID NO 3
<211> LENGTH: 3649
<212> TYPE: DNA
<213> ORGANISM: Escherichia coli

<400> SEQUENCE: 3

```
aacgaattca agcttgatat cattcaggac gagcctcaga ctccagcgta actggactga     60

aaacaaacta aagcgccctt gtggcgcttt agttttgttc cgctcatgat aataatggtt    120

tcttagacgt caggtggcac ttttcgggga aatgtgcgcg cccgcgttcc tgctggcgct    180

gggcctgttt ctggcgctgg acttcccgct gttccgtcag cagcttttcg cccacggcct    240

tgatgatcgc ggcggccttg gcctgcatat cccgattcaa cggccccagg gcgtccagaa    300

cgggcttcag gcgctcccga aggtctcggg ccgtctcttg ggcttgatcg gccttcttgc    360

gcatctcacg cgctcctgcg gcggcctgta gggcaggctc atacccctgc cgaaccgctt    420

ttgtcagccg gtcggccacg gcttccggcg tctcaacgcg ctttgagatt cccagctttt    480

cggccaatcc ctgcggtgca taggcgcgtg gctcgaccgc ttgcgggctg atggtgacgt    540

ggcccactgg tggccgctcc agggcctcgt agaacgcctg aatgcgcgtg tgacgtgcct    600
```

-continued tgctgccctc gatgccccgt tgcagcccta gatcggccac agcggccgca aacgtggtct 660
ggtcgcgggt catctgcgct ttgttgccga tgaactcctt ggccgacagc ctgccgtcct 720
gcgtcagcgg caccacgaac gcggtcatgt gcgggctggt ttcgtcacgg tggatgctgg 780
ccgtcacgat gcgatccgcc ccgtacttgt ccgccagcca cttgtgcgcc ttctcgaaga 840
acgccgcctg ctgttcttgg ctggccgact tccaccattc cgggctggcc gtcatgacgt 900
actcgaccgc caacacagcg tccttgcgcc gcttctctgg cagcaactcg cgcagtcggc 960
ccatcgcttc atcggtgctg ctggccgccc agtgctcgtt ctctggcgtc ctgctggcgt 1020
cagcgttggg cgtctcgcgc tcgcggtagg cgtgcttgag actggccgcc acgttgccca 1080
ttttcgccag cttcttgcat cgcatgatcg cgtatgccgc catgcctgcc cctccctttt 1140
ggtgtccaac cggctcgacg gggcagcgc aaggcggtgc ctccggcggg ccactcaatg 1200
cttgagtata ctcactagac tttgcttcgc aaagtcgtga ccgcctacgg cggctgcggc 1260
gccctacggg cttgctctcc gggcttcgcc ctgcgcggtc gctgcgctcc cttgccagcc 1320
cgtggatatg tggacgatgg ccgcgagcgg ccaccggctg gctcgcttcg ctcggcccgt 1380
ggacaaccct gctggacaag ctgatggaca ggctgcgcct gcccacgagc ttgaccacag 1440
ggattgccca ccggctaccc agccttcgac cacataccca ccggctccaa ctgcgcggcc 1500
tgcggccttg ccccatcaat ttttttaatt ttctctgggg aaaagcctcc ggcctgcggc 1560
ctgcgcgctt cgcttgccgg ttggacacca agtggaaggc gggtcaaggc tcgcgcagcg 1620
accgcgcagc ggcttggcct tgacgcgcct ggaacgaccc aagcctatgc gagtgggggc 1680
agtcgaaggc gaagcccgcc cgcctgcccc ccgagcctca cggcggcgag tgcgggggtt 1740
ccaagggggc agcgccacct tgggcaaggc cgaaggccgc gcagtcgatc aacaagcccc 1800
ggagggggca ctttttgccg gagggggagc cgcgccgaag gcgtggggga accccgcagg 1860
ggtgcccttc tttgggcacc aaagaactag atatagggcg aaatgcgaaa gacttaaaaa 1920
tcaacaactt aaaaaagggg ggtacgcaac agctcattgc ggcacccccc gcaatagctc 1980
attgcgtagg ttaaagaaaa tctgtaattg actgccactt ttacgcaacg cataattgtt 2040
gtcgcgctgc cgaaaagttg cagctgattg cgcatggtgc cgcaaccgtg cggcacccta 2100
ccgcatggag ataagcatgg ccacgcagtc cagagaaatc ggcattcaag ccaagaacaa 2160
gcccggtcac tgggtgcaaa cggaacgcaa agcgcatgag gcgtgggccg ggcttattgc 2220
gaggaaaccc acggcggcaa tgctgctgca tcacctcgtg gcgcagatgg gccaccagaa 2280
cgccgtggtg gtcagccaga agacactttc caagctcatc ggacgttctt tgcggacggt 2340
ccaatacgca gtcaaggact tggtggccga gcgctggatc tccgtcgtga agctcaacgg 2400
ccccggcacc gtgtcggcct acgtggtcaa tgaccgcgtg gcgtggggcc agccccgcga 2460
ccagttgcgc ctgtcggtgt tcagtgccgc cgtggtggtt gatcacgacg accaggacga 2520
atcgctgttg ggcatggcg acctgcgccg catcccgacc ctgtatccgg gcgagcagca 2580
actaccgacc ggccccggcg aggagccgcc cagccagccc ggcattccgg gcatggaacc 2640
agacctgcca gccttgaccg aaacggagga atgggaacgg cgcgggcagc agcgcctgcc 2700
gatgcccgat gagccgtgtt ttctggacga tggcgagccg ttggagccgc cgacacgggt 2760
cacgctgccg cgccggtagt acgtaagagg ttccaacttt caccataatg aaataagatc 2820
actaccgggc gtattttttg agttatcgag attttcagga gctaaggaag ctaaaatgga 2880
gaaaaaaatc actggatata ccaccgttga tatatcccaa tggcatcgta aagaacattt 2940
tgaggcattt cagtcagttg ctcaatgtac ctataaccag accgttcagc tggatattac 3000

```
ggccttttta aagaccgtaa agaaaaataa gcacaagttt tatccggcct ttattcacat   3060

tcttgcccgc ctgatgaatg ctcatccgga attccgtatg gcaatgaaag acggtgagct   3120

ggtgatatgg gatagtgttc acccttgtta caccgttttc catgagcaaa ctgaaacgtt   3180

ttcatcgctc tggagtgaat accacgacga tttccggcag tttctacaca tatattcgca   3240

agatgtggcg tgttacggtg aaaacctggc ctatttccct aaagggttta ttgagaatat   3300

gtttttcgtc tcagccaatc cctgggtgag tttcaccagt tttgatttaa acgtggccaa   3360

tatggacaac ttcttcgccc ccgttttcac catgggcaaa tattatacgc aaggcgacaa   3420

ggtgctgatg ccgctggcga ttcaggttca tcatgccgtt tgtgatggct tccatgtcgg   3480

cagaatgctt aatgaattac aacagtactg cgatgagtgg cagggcgggg cgtaaacgcg   3540

tggatccccc tcaagtcaaa agcctccggt cggaggcttt tgactttctg ctatggaggt   3600

caggtatgat ttaaatggtc agtattgagc gatatctaga gaattcgtc               3649
```

<210> SEQ ID NO 4
<211> LENGTH: 4181
<212> TYPE: DNA
<213> ORGANISM: Escherichia coli

<400> SEQUENCE: 4

```
aacgaattca agcttgatat cattcaggac gagcctcaga ctccagcgta actggactga     60

aaacaaacta aagcgccctt gtggcgcttt agttttgttc cgctcatgat aataatggtt    120

tcttagacgt caggtggcac ttttcgggga aatgtgcgcg cccgcgttcc tgctggcgct    180

gggcctgttt ctggcgctgg acttcccgct gttccgtcag cagcttttcg cccacggcct    240

tgatgatcgc ggcggccttg gcctgcatat cccgattcaa cggccccagg gcgtccagaa    300

cgggcttcag gcgctcccga aggtctcggg ccgtctcttg ggcttgatcg gccttcttgc    360

gcatctcacg cgctcctgcg gcggcctgta gggcaggctc atacccctgc cgaaccgctt    420

ttgtcagccg gtcggccacg gcttccggcg tctcaacgcg ctttgagatt cccagctttt    480

cggccaatcc ctgcggtgca taggcgcgtg gctcgaccgc ttgcgggctg atggtgacgt    540

ggcccactgg tggccgctcc agggcctcgt agaacgcctg aatgcgcgtg tgacgtgcct    600

tgctgccctc gatgccccgt tgcagcccta gatcggccac agcggccgca aacgtggtct    660

ggtcgcgggt catctgcgct ttgttgccga tgaactcctt ggccgacagc ctgccgtcct    720

gcgtcagcgg caccacgaac gcggtcatgt gcgggctggt ttcgtcacgg tggatgctgg    780

ccgtcacgat gcgatccgcc ccgtacttgt ccgccagcca cttgtgcgcc ttctcgaaga    840

acgccgcctg ctgttcttgg ctggccgact tccaccattc cgggctggcc gtcatgacgt    900

actcgaccgc caacacagcg tccttgcgcc gcttctctgg cagcaactcg cgcagtcggc    960

ccatcgcttc atcggtgctg ctggccgccc agtgctcgtt ctctggcgtc ctgctggcgt   1020

cagcgttggg cgtctcgcgc tcgcggtagg cgtgcttgag actggccgcc acgttgccca   1080

ttttcgccag cttcttgcat cgcatgatcg cgtatgccgc catgcctgcc cctccctttt   1140

ggtgtccaac cggctcgacg ggggcagcgc aaggcggtgc ctccggcggg ccactcaatg   1200

cttgagtata ctcactagac tttgcttcgc aaagtcgtga ccgcctacgg cggctgcggc   1260

gccctacggg cttgctctcc gggcttcgcc ctgcgcggtc gctgcgctcc cttgccagcc   1320

cgtggatatg tggacgatgg ccgcgagcgg ccaccggctg gctcgcttcg ctcggcccgt   1380

ggacaaccct gctggacaag ctgatggaca ggctgcgcct gcccacgagc ttgaccacag   1440
```

-continued

```
ggattgccca ccggctaccc agccttcgac cacataccca ccggctccaa ctgcgcggcc   1500

tgcggccttg ccccatcaat ttttttaatt ttctctgggg aaaagcctcc ggcctgcggc   1560

ctgcgcgctt cgcttgccgg ttggacacca agtggaaggc gggtcaaggc tcgcgcagcg   1620

accgcgcagc ggcttggcct tgacgcgcct ggaacgaccc aagcctatgc gagtgggggc   1680

agtcgaaggc gaagcccgcc cgcctgcccc ccgagcctca cggcggcgag tgcgggggtt   1740

ccaagggggc agcgccacct tgggcaaggc cgaaggccgc gcagtcgatc aacaagcccc   1800

ggaggggcca ctttttgccg gagggggagc cgcgccgaag gcgtggggga accccgcagg   1860

ggtgcccttc tttgggcacc aaagaactag atatagggcg aaatgcgaaa gacttaaaaa   1920

tcaacaactt aaaaaagggg ggtacgcaac agctcattgc ggcacccccc gcaatagctc   1980

attgcgtagg ttaaagaaaa tctgtaattg actgccactt ttacgcaacg cataattgtt   2040

gtcgcgctgc cgaaaagttg cagctgattg cgcatggtgc cgcaaccgtg cggcacccta   2100

ccgcatggag ataagcatgg ccacgcagtc cagagaaatc ggcattcaag ccaagaacaa   2160

gcccggtcac tgggtgcaaa cggaacgcaa agcgcatgag gcgtgggccg ggcttattgc   2220

gaggaaaccc acggcggcaa tgctgctgca tcacctcgtg gcgcagatgg gccaccagaa   2280

cgccgtggtg gtcagccaga agacactttc caagctcatc ggacgttctt tgcggacggt   2340

ccaatacgca gtcaaggact tggtggccga gcgctggatc tccgtcgtga agctcaacgg   2400

ccccggcacc gtgtcggcct acgtggtcaa tgaccgcgtg gcgtggggcc agccccgcga   2460

ccagttgcgc ctgtcggtgt tcagtgccgc cgtggtggtt gatcacgacg accaggacga   2520

atcgctgttg gggcatggcg acctgcgccg catcccgacc ctgtatccgg gcgagcagca   2580

actaccgacc ggcccccggcg aggagccgcc cagccagccc ggcattccgg gcatggaacc   2640

agacctgcca gccttgaccg aaacggagga atgggaacgg cgcgggcagc agcgcctgcc   2700

gatgcccgat gagccgtgtt ttctggacga tggcgagccg ttggagccgc cgacacgggt   2760

cacgctgccg cgccggtagt acgtaagagg ttccaacttt caccataatg aaataagatc   2820

actaccgggc gtattttttg agttatcgag attttcagga gctaaggaag ctaaaatgaa   2880

atctaacaat gcgctcatcg tcatcctcgg caccgtcacc ctggatgctg taggcatagg   2940

cttggttatg ccggtactgc cgggcctctt gcgggatatc gtccattccg acagcatcgc   3000

cagtcactat ggcgtgctgc tagcgctata tgcgttgatg caatttctat gcgcacccgt   3060

tctcggagca ctgtccgacc gctttggccg ccgcccagtc ctgctcgctt cgctacttgg   3120

agccactatc gactacgcga tcatggcgac cacacccgtc ctgtggatcc tctacgccgg   3180

acgcatcgtg gccggcatca ccggcgccac aggtgcggtt gctggcgcct atatcgccga   3240

catcaccgat ggggaagatc gggctcgcca cttcgggctc atgagcgctt gtttcggcgt   3300

gggtatggtg gcaggccccg tggccggggg actgttgggc gccatctcct tgcatgcacc   3360

attccttgcg gcggcggtgc tcaacggcct caacctacta ctgggctgct tcctaatgca   3420

ggagtcgcat aagggagagc gtcgaccgat gcccttgaga gccttcaacc cagtcagctc   3480

cttccggtgg gcgcggggca tgactatcgt cgccgcactt atgactgtct tctttatcat   3540

gcaactcgta ggacaggtgc cggcagcgct ctgggtcatt ttcggcgagg accgctttcg   3600

ctggagcgcg acgatgatcg gcctgtcgct tgcggtattc ggaatcttgc acgccctcgc   3660

tcaagccttc gtcactggtc ccgccaccaa acgtttcggc gagaagcagg ccattatcgc   3720

cggcatggcg gccgacgcgc tgggctacgt cttgctggcg ttcgcgacgc gaggctggat   3780

ggccttcccc attatgattc ttctcgcttc cggcggcatc gggatgcccg cgttgcaggc   3840
```

-continued

```
catgctgtcc aggcaggtag atgacgacca tcagggacag cttcaaggat cgctcgcggc   3900

tcttaccagc ctaacttcga tcactggacc gctgatcgtc acggcgattt atgccgcctc   3960

ggcgagcaca tggaacgggt tggcatggat tgtaggcgcc gccctatacc ttgtctgcct   4020

ccccgcgttg cgtcgcggtg catggagccg ggccacctcg acctgaatgg aagggatccc   4080

cctcaagtca aaagcctccg gtcggaggct tttgactttc tgctatggag gtcaggtatg   4140

atttaaatgg tcagtattga gcgatatcta gagaattcgt c                        4181
```

<210> SEQ ID NO 5
<211> LENGTH: 3224
<212> TYPE: DNA
<213> ORGANISM: Escherichia coli

<400> SEQUENCE: 5

```
aacgaattca agcttgatat cattcaggac gagcctcaga ctccagcgta actggactga     60

aaacaaacta aagcgccctt gtggcgcttt agttttgttc cgctcatgat aataatggtt    120

tcttagacgt caggtggcac ttttcgggga aatgtgcgcg cccgcgttcc tgctggcgct    180

gggcctgttt ctggcgctgg acttcccgct gttccgtcag cagcttttcg cccacggcct    240

tgatgatcgc ggcggccttg gcctgcatat cccgattcaa cggccccagg gcgtccagaa    300

cgggcttcag gcgctcccga aggtctcggg ccgtctcttg ggcttgatcg gccttcttgc    360

gcatctcacg cgctcctgcg gcggcctgta gggcaggctc atacccctgc cgaaccgctt    420

ttgtcagccg gtcggccacg gcttccggcg tctcaacgcg ctttgagatt cccagctttt    480

cggccaatcc ctgcggtgca taggcgcgtg gctcgaccgc ttgcgggctg atggtgacgt    540

ggcccactgg tggccgctcc agggcctcgt agaacgcctg aatgcgcgtg tgacgtgcct    600

tgctgccctc gatgccccgt tgcagcccta gatcggccac agcggccgca aacgtggtct    660

ggtcgcgggt catctgcgct ttgttgccga tgaactcctt ggccgacagc ctgccgtcct    720

gcgtcagcgg caccacgaac gcggtcatgt gcgggctggt ttcgtcacgg tggatgctgg    780

ccgtcacgat gcgatccgcc ccgtacttgt ccgccagcca cttgtgcgcc ttctcgaaga    840

acgccgcctg ctgttcttgg ctggccgact tccaccattc cgggctggcc gtcatgacgt    900

actcgaccgc caacacagcg tccttgcgcc gcttctctgg cagcaactcg cgcagtcggc    960

ccatcgcttc atcggtgctg ctggccgccc agtgctcgtt ctctggcgtc ctgctggcgt   1020

cagcgttggg cgtctcgcgc tcgcggtagg cgtgcttgag actggccgcc acgttgccca   1080

ttttcgccag cttcttgcat cgcatgatcg cgtatgccgc catgcctgcc cctccctttt   1140

ggtgtccaac cggctcgacg gggcagcgc aaggcggtgc ctccggcggg ccactcaatg   1200

cttgagtata ctcactagac tttgcttcgc aaagtcgtga ccgcctacgg cggctgcggc   1260

gccctacggg cttgctctcc gggcttcgcc ctgcgcggtc gctgcgctcc cttgccagcc   1320

cgtggatatg tggacgatgg ccgcgagcgg ccaccggctg gctcgcttcg ctcggcccgt   1380

ggacaaccct gctggacaag ctgatggaca ggctgcgcct gcccacgagc ttgaccacag   1440

ggattgccca ccggctaccc agccttcgac cacataccca ccggctccaa ctgcgcggcc   1500

tgcggccttg ccccatcaat ttttttaatt ttctctgggg aaaagcctcc ggcctgcggc   1560

ctgcgcgctt cgcttgccgg ttggacacca agtggaaggc gggtcaaggc tcgcgcagcg   1620

accgcgcagc ggcttggcct tgacgcgcct ggaacgaccc aagcctatgc gagtgggggc   1680

agtcgaaggc gaagcccgcc cgcctgcccc ccgagcctca cggcggcgag tgcgggggtt   1740
```

-continued

```
ccaagggggc agcgccacct tgggcaaggc cgaaggccgc gcagtcgatc aacaagcccc   1800

ggaggggcca ctttttgccg gagggggagc cgcgccgaag gcgtggggga accccgcagg   1860

ggtgcccttc tttgggcacc aaagaactag atatagggcg aaatgcgaaa gacttaaaaa   1920

tcaacaactt aaaaaagggg ggtacgcaac agctcattgc ggcacccccc gcaatagctc   1980

attgcgtagg ttaaagaaaa tctgtaattg actgccactt ttacgcaacg cataattgtt   2040

gtcgcgctgc cgaaaagttg cagctgattg cgcatggtgc cgcaaccgtg cggcacccta   2100

ccgcatggag ataagcatgg ccacgcagtc cagagaaatc ggcattcaag ccaagaacaa   2160

gcccggtcac tgggtgcaaa cggaacgcaa agcgcatgag gcgtgggccg ggcttattgc   2220

gaggaaaccc acggcggcaa tgctgctgca tcacctcgtg gcgcagatgg gccaccagaa   2280

cgccgtggtg gtcagccaga agacactttc caagctcatc ggacgttctt tgcggacggt   2340

ccaatacgca gtcaaggact tggtggccga gcgctggatc tccgtcgtga agctcaacgg   2400

ccccggcacc gtgtcggcct acgtggtcaa tgaccgcgtg gcgtggggcc agccccgcga   2460

ccagttgcgc ctgtcggtgt tcagtgccgc cgtggtggtt gatcacgacg accaggacga   2520

atcgctgttg gggcatggcg acctgcgccg catcccgacc ctgtatccgg gcgagcagca   2580

actaccgacc ggccccggcg aggagccgcc cagccagccc ggcattccgg gcatggaacc   2640

agacctgcca gccttgaccg aaacggagga atgggaacgg cgcgggcagc agcgcctgcc   2700

gatgcccgat gagccgtgtt ttctggacga tggcgagccg ttggagccgc cgacacgggt   2760

cacgctgccg cgccggtagt acgtaagagg ttccaacttt caccataatg aaataagatc   2820

actaccgggc gtattttttg agttatcgag attttcagga gctaaggaag ctaaaatggg   2880

tcaaagtagc gatgaagcca acgctcccgt tgcagggcag tttgcgcttc ccctgagtgc   2940

cacctttggc ttaggggatc gcgtacgcaa gaaatctggt gccgcttggc agggtcaagt   3000

cgtcggttgg tattgcacaa aactcactcc tgaaggctat gcggtcgagt ccgaatccca   3060

cccaggctca gtgcaaattt atcctgtggc tgcacttgaa cgtgtggcct aagaatggat   3120

ccccctcaag tcaaaagcct ccggtcggag gcttttgact ttctgctatg gaggtcaggt   3180

atgatttaaa tggtcagtat tgagcgatat ctagagaatt cgtc                    3224
```

<210> SEQ ID NO 6
<211> LENGTH: 5862
<212> TYPE: DNA
<213> ORGANISM: Escherichia coli

<400> SEQUENCE: 6

```
aacgaattca agcttgatat cattcaggac gagcctcaga ctccagcgta actggactga     60

aaacaaacta aagcgccctt gtggcgcttt agttttgttc cgctcatgat aataatggtt    120

tcttagacgt caggtggcac ttttcgggga aatgtgcgcg cccgcgttcc tgctggcgct    180

gggcctgttt ctggcgctgg acttcccgct gttccgtcag cagcttttcg cccacggcct    240

tgatgatcgc ggcggccttg gcctgcatat cccgattcaa cggccccagg gcgtccagaa    300

cgggcttcag gcgctcccga aggtctcggg ccgtctcttg ggcttgatcg gccttcttgc    360

gcatctcacg cgctcctgcg gcggcctgta gggcaggctc ataccccctgc cgaaccgctt    420

ttgtcagccg gtcggccacg gcttccggcg tctcaacgcg ctttgagatt cccagctttt    480

cggccaatcc ctgcggtgca taggcgcgtg gctcgaccgc ttgcgggctg atggtgacgt    540

ggcccactgg tggccgctcc agggcctcgt agaacgcctg aatgcgcgtg tgacgtgcct    600

tgctgccctc gatgccccgt tgcagcccta gatcggccac agcggccgca aacgtggtct    660
```

-continued

```
ggtcgcgggt catctgcgct ttgttgccga tgaactcctt ggccgacagc ctgccgtcct    720
gcgtcagcgg caccacgaac gcggtcatgt gcgggctggt ttcgtcacgg tggatgctgg    780
ccgtcacgat gcgatccgcc ccgtacttgt ccgccagcca cttgtgcgcc ttctcgaaga    840
acgccgcctg ctgttcttgg ctggccgact tccaccattc cgggctggcc gtcatgacgt    900
actcgaccgc caacacagcg tccttgcgcc gcttctctgg cagcaactcg cgcagtcggc    960
ccatcgcttc atcggtgctg ctggccgccc agtgctcgtt ctctggcgtc ctgctggcgt   1020
cagcgttggg cgtctcgcgc tcgcggtagg cgtgcttgag actggccgcc acgttgccca   1080
ttttcgccag cttcttgcat cgcatgatcg cgtatgccgc catgcctgcc cctccctttt   1140
ggtgtccaac cggctcgacg gggcagcgc aaggcggtgc ctccggcggg ccactcaatg   1200
cttgagtata ctcactagac tttgcttcgc aaagtcgtga ccgcctacgg cggctgcggc   1260
gccctacggg cttgctctcc gggcttcgcc ctgcgcggtc gctgcgctcc cttgccagcc   1320
cgtggatatg tggacgatgg ccgcgagcgg ccaccggctg gctcgcttcg ctcggcccgt   1380
ggacaaccct gctggacaag ctgatggaca ggctgcgcct gcccacgagc ttgaccacag   1440
ggattgccca ccggctaccc agccttcgac cacataccca ccggctccaa ctgcgcggcc   1500
tgcggccttg ccccatcaat ttttttaatt ttctctgggg aaaagcctcc ggcctgcggc   1560
ctgcgcgctt cgcttgccgg ttggacacca agtggaaggc gggtcaaggc tcgcgcagcg   1620
accgcgcagc ggcttggcct tgacgcgcct ggaacgaccc aagcctatgc gagtgggggc   1680
agtcgaaggc gaagcccgcc cgcctgcccc ccgagcctca cggcggcgag tgcgggggtt   1740
ccaaggggc agcgccacct tgggcaaggc cgaaggccgc gcagtcgatc aacaagcccc   1800
ggaggggcca ctttttgccg gagggggagc cgcgccgaag gcgtgggga accccgcagg   1860
ggtgcccttc tttgggcacc aaagaactag atatagggcg aaatgcgaaa gacttaaaaa   1920
tcaacaactt aaaaaagggg ggtacgcaac agctcattgc ggcacccccc gcaatagctc   1980
attgcgtagg ttaaagaaaa tctgtaattg actgccactt ttacgcaacg cataattgtt   2040
gtcgcgctgc cgaaaagttg cagctgattg cgcatggtgc cgcaaccgtg cggcacccta   2100
ccgcatggag ataagcatgg ccacgcagtc cagagaaatc ggcattcaag ccaagaacaa   2160
gcccggtcac tgggtgcaaa cggaacgcaa agcgcatgag gcgtgggccg ggcttattgc   2220
gaggaaaccc acggcggcaa tgctgctgca tcacctcgtg gcgcagatgg gccaccagaa   2280
cgccgtggtg gtcagccaga agacactttc caagctcatc ggacgttctt tgcggacggt   2340
ccaatacgca gtcaaggact tggtggccga gcgctggatc tccgtcgtga agctcaacgg   2400
ccccggcacc gtgtcggcct acgtggtcaa tgaccgcgtg gcgtggggcc agccccgcga   2460
ccagttgcgc ctgtcggtgt tcagtgccgc cgtggtggtt gatcacgacg accaggacga   2520
atcgctgttg ggcatggcg acctgcgccg catcccgacc ctgtatccgg gcgagcagca   2580
actaccgacc ggccccggcg aggagccgcc cagccagccc ggcattccgg gcatggaacc   2640
agacctgcca gccttgaccg aaacggagga atgggaacgg cgcgggcagc agcgcctgcc   2700
gatgcccgat gagccgtgtt ttctggacga tggcgagccg ttggagccgc cgacacgggt   2760
cacgctgccg cgccggtagt acgtaagagg ttccaacttt caccataatg aaataagatc   2820
actaccgggc gtatttttg agttatcgag attttcagga gctaaggaag ctaaaatgga   2880
agaacaaagc gtgaacatgg cgcgattgaa gggggaggtt ttgcccgccc tcttcgcgtc   2940
gccggcgacg attggcgagt acggggccgg catcgacggg gcggattccc tcaacgagct   3000
```

-continued

```
gtcgaatctg atggagcacg gcgcagttgc cgcgctggcc gacaaaatca gccagatcgt   3060
ggcgaagctg gccgacgcgg acccccgcaa gatcgcggaa aagcctacct ggttcgagaa   3120
gatgcttggc cgtgaggttg aacgccaggt gaggtatcag gtcgcccgca agacgctcga   3180
ccagttgctg gacgaagccg agggcgtagc gcagcgcgtg cgggacacgt tgcgcgcctt   3240
ggatgacatg ctcaatacgc atgaggccga ggtagaccgg ctcagagcct acattcaagc   3300
cgggcgcgag ttcctggacg agaaccccga ggccggcgcg gccaaggccg gcgtgatcga   3360
gttcgacaag ccgcgcgaac gcttcgcgcg caagctcgcc aacctggcaa ccctcatggc   3420
gtcccatgaa atgagcgtca ctcagatgaa gctcacgcgg gcgcaggccg tggacatgct   3480
ggaccgcttc tctgaaacgg catccgtcct ggtgcccgtc tggcgtcagc acaccctcgc   3540
gctcatcacc accaagaaca tgaatccggc aatggtcgcc gaggcggcca aagctcacca   3600
ggcgctcatg cggagccttt cgcagagcct ggaaggcatc aaccaataac acggcgggag   3660
aaccctatga acgcactgaa aacgacgcac gacgccaagg cccctatcgt cgccttcgac   3720
atgaccccgg caaccctgcg cgagctgggc ttgcaggaaa gcgacgtgcc ggaagtccat   3780
gcggtcgcgc agcggatcga ggtcggcagt ccgcagaccg ttgccgagtt cggccgcgac   3840
gtggccgagc acacgtcccg ctacgccgat agcctgctgg accaggtgcg caacagcgac   3900
ctggacgaag caggcgagaa actgacccag gttgtcgcca aggcccgttc cctgaacgtc   3960
ggcccctttgt ccgacaaccg ttcccgcctg cccctgattg gcccgctgat cgaccgcttc   4020
cgcgtccgtt cgacgggctt catggcgcgc ttcgacacga cccgcgagca gatcgaacac   4080
ctggtcagcg aagtgcagac cacccagcaa ggcatcgcgc agcgcaatgc ctcgctcgac   4140
gaaatgttcg cagccgtgcg cgaggaacac cgccttcttg gcgtccacat cgcggccggc   4200
aaggtccgcc ttgccgagct gcgcgagcag gccgagggtc tgcgcggcaa tgtcgggaac   4260
gacccgggcc gcgtgcagga gctggccgac ctcgatgcga tggttgccaa cctggacaag   4320
cgcatcggcg acctgatcgc cttgcaacat tcggccatgc agagcctgcc gaccatccgc   4380
atgatccagg ccaacaacca gatgctggtc gataaattcc acaccatccg cgaaatcacc   4440
gtgccggcgt ggaagcggca attcatgctg gccttgagcc tcaacgagca gaagaacgcc   4500
gtcgaactgg ccacggccat cgacgacacc accaacgacc tgatgaagcg caatgcggcc   4560
ctgctgcatc gcacgtccgt cgagacggcg aaggagaacc aacgcctggt gatcgacgtg   4620
gacacgctca agcaggttca gacgacgctc atcaagaccg tcgaggacgt tattcgcatc   4680
cagcaggaag gcgtgcagaa gcgcaaggat gccgagaagc agatcgccgc aatgcgtggc   4740
gatcttcaag ccaagctgac ccgccagccc gtgcgcgagc tggcccaaca ggagtccgta   4800
tgaatgccac aaacaccgat gttttcgccc aggtaggcgg cctcgaggcc cgaggcgcga   4860
agatgaagaa gcggggcacc cgcttcctca tcgcggcgct ggcagtcctt gccattgccg   4920
ggatcggggc agtaacggga tgggcgatca gcccgagcgc gacgcccgga agcattgacg   4980
tgccgcaggt gctggcatcg acattcagcg accaggtgcc gggcagtgag ggcggcggcc   5040
tgggtggcgg cctgcccttc acttcggccg tcggggcatt cacggacttc atggcggggc   5100
cggcaatttt taccttgggc attcttggca tagtggtcgc gggtgccgtg ctcgtgttcg   5160
gggtgaatt ctgcgggttc gtgcgatccg tctgcatgat ggtgatagcc gtcagcatga   5220
ttttcgtgtc gtcgaacttg gtgaagggca ttctcggcgg cgatcacgac gccggccctg   5280
cggagccttc gccgcgtgcg cgattcatgg cggccgtgga ggccaaggat ttcgcgcgag   5340
tgcaagagct gatcgaggcg cgtggagcca agtcggcggc tgattatgtc cttgcgcagc   5400
```

-continued

```
tcgccgtggc cgaaggtctg gaccgcaagc ctggtgcgcg cgtcgtggtc gggaaagcgg   5460
cgggcagcat ggcaatgccg cctgcggcgc tgggttttac gccaagggga gaagcggcat   5520
acgccatcga gcggtcagcc tatggtgagc cgaggtccag cattgcgaag cagtaccagc   5580
aggaatggaa ccggaaggcg gcgacctggt gggcgatggc cggtgtggcc ggcatcatcg   5640
gcgcgatcct ggcggcggcg gcaaccggct ttgttgggct ggcagtgtcg atccgcaacc   5700
gagtgaagcg cgtgcgcgac ctgttggtga tggagccggg tgcagagcca taagggatcc   5760
ccctcaagtc aaaagcctcc ggtcggaggc ttttgacttt ctgctatgga ggtcaggtat   5820
gatttaaatg gtcagtattg agcgatatct agagaattcg tc                      5862
```

```
<210> SEQ ID NO 7
<211> LENGTH: 2602
<212> TYPE: DNA
<213> ORGANISM: Escherichia coli

<400> SEQUENCE: 7

aacgaattca agcttgatat cattcaggac gagcctcaga ctccagcgta actggactga     60
aaacaaacta aagcgccctt gtggcgcttt agttttgttc cgcggccacc ggctggctcg    120
cttcgctcgg cccgtggaca accctgctgg acaagctgat ggacaggctg cgcctgccca    180
cgagcttgac cacagggatt gcccaccggc tacccagcct tcgaccacat acccaccggc    240
tccaactgcg cggcctgcgg ccttgcccca tcaatttttt taattttctc tggggaaaag    300
cctccggcct gcggcctgcg cgcttcgctt gccggttgga caccaagtgg aaggcgggtc    360
aaggctcgcg cagcgaccgc gcagcggctt ggccttgacg cgcctggaac gacccaagcc    420
tatgcgagtg ggggcagtcg aaggcgaagc ccgcccgcct gccccccgag cctcacggcg    480
gcgagtgcgg gggttccaag gggcagcgc caccttgggc aaggccgaag gccgcgcagt    540
cgatcaacaa gccccggagg ggccactttt tgccggaggg ggagccgcgc cgaaggcgtg    600
ggggaacccc gcaggggtgc ccttctttgg gcaccaaaga actagatata gggcgaaatg    660
cgaaagactt aaaaatcaac aacttaaaaa aggggggtac gcaacagctc attgcggcac    720
cccccgcaat agctcattgc gtaggttaaa gaaaatctgt aattgactgc cacttttacg    780
caacgcataa ttgttgtcgc gctgccgaaa agttgcagct gattgcgcat ggtgccgcaa    840
ccgtgcggca ccctaccgca tggagataag catggccacg cagtccagag aaatcggcat    900
tcaagccaag aacaagcccg gtcactgggt gcaaacggaa cgcaaagcgc atgaggcgtg    960
ggccgggctt attgcgagga aacccacggc ggcaatgctg ctgcatcacc tcgtggcgca   1020
gatgggccac cagaacgccg tggtggtcag ccagaagaca ctttccaagc tcatcggacg   1080
ttctttgcgg acggtccaat acgcagtcaa ggacttggtg gccgagcgct ggatctccgt   1140
cgtgaagctc aacggccccg gcaccgtgtc ggcctacgtg gtcaatgacc gcgtggcgtg   1200
ggccagccc cgcgaccagt tgcgcctgtc ggtgttcagt gccgccgtgg tggttgatca   1260
cgacgaccag gacgaatcgc tgttggggca tggcgacctg cgccgcatcc cgaccctgta   1320
tccgggcgag cagcaactac cgaccggccc cggcgaggag ccgcccagcc agcccggcat   1380
tccgggcatg gaaccagacc tgccagcctt gaccgaaacg gaggaatggg aacggcgcgg   1440
gcagcagcgc ctgccgatgc ccgatgagcc gtgttttctg gacgatggcg agccgttgga   1500
gccgccgaca cgggtcacgc tgccgcgccg gtagtacgta agaggttcca actttcacca   1560
taatgaaata agatcactac cgggcgtatt ttttgagtta tcgagatttt caggagctaa   1620
```

-continued

```
ggaagctaaa atgagtattc aacatttccg tgtcgccctt attccctttt ttgcggcatt   1680

ttgccttcct gtttttgctc acccagaaac gctggtgaaa gtaaaagatg ctgaagatca   1740

gttgggtgca cgagtgggtt acatcgaact ggatctcaac agcggtaaga tccttgagag   1800

ttttcgcccc gaagaacgtt ttccaatgat gagcactttt aaagttctgc tatgtggcgc   1860

ggtattatcc cgtattgacg ccgggcaaga gcaactcggt cgccgcatac actattctca   1920

gaatgacttg gttgagtact caccagtcac agaaaagcat cttacggatg gcatgacagt   1980

aagagaatta tgcagtgctg ccataaccat gagtgataac actgcggcca acttacttct   2040

ggcaacgatc ggaggaccga aggagctaac cgcttttttg cacaacatgg gggatcatgt   2100

aactcgcctt gatcgttggg aaccggagct gaatgaagcc ataccaaacg acgagcgtga   2160

caccacgatg cctgtagcaa tggcaacaac gttgcgcaaa ctattaactg gcgaactact   2220

tactctagct tcccggcaac aattaataga ctggatggag gcggataaag ttgcaggatc   2280

acttctgcgc tcggcccttc cggctggctg gtttattgct gataaatctg gagccggtga   2340

gcgtgggtct cgcggtatca ttgcagcact ggggccagat ggtaagccct cccgcatcgt   2400

agttatctac acgacgggga gtcaggcaac tatggatgaa cgaaatagac agatcgctga   2460

gataggtgcc tcactgatta agcattggta atgaggatcc ccctcaagtc aaaagcctcc   2520

ggtcggaggc ttttgacttt ctgctatgga ggtcaggtat gatttaaatg gtcagtattg   2580

agcgatatct agagaattcg tc                                             2602
```

```
<210> SEQ ID NO 8
<211> LENGTH: 2558
<212> TYPE: DNA
<213> ORGANISM: Escherichia coli

<400> SEQUENCE: 8
```

```
aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180

cgagcttgac cacagggatt gcccaccggc tacccagcct tcgaccacat acccaccggc    240

tccaactgcg cggcctgcgg ccttgcccca tcaatttttt taatttctc tggggaaaag    300

cctccggcct gcggcctgcg cgcttcgctt gccggttgga caccaagtgg aaggcgggtc    360

aaggctcgcg cagcgaccgc gcagcggctt ggccttgacg cgcctggaac gacccaagcc    420

tatgcgagtg ggggcagtcg aaggcgaagc ccgcccgcct gcccccccgag cctcacggcg    480

gcgagtgcgg gggttccaag gggcagcgc caccttgggc aaggccgaag gccgcgcagt    540

cgatcaacaa gccccggagg ggccactttt tgccggaggg ggagccgcgc cgaaggcgtg    600

ggggaacccc gcaggggtgc ccttctttgg gcaccaaaga actagatata gggcgaaatg    660

cgaaagactt aaaaatcaac aacttaaaaa aggggggtac gcaacagctc attgcggcac    720

cccccgcaat agctcattgc gtaggttaaa gaaaatctgt aattgactgc cacttttacg    780

caacgcataa ttgttgtcgc gctgccgaaa agttgcagct gattgcgcat ggtgccgcaa    840

ccgtgcggca ccctaccgca tggagataag catggccacg cagtccagag aaatcggcat    900

tcaagccaag aacaagcccg gtcactgggt gcaaacggaa cgcaaagcgc atgaggcgtg    960

ggccgggctt attgcgagga aacccacggc ggcaatgctg ctgcatcacc tcgtggcgca   1020

gatgggccac cagaacgccg tggtggtcag ccagaagaca ctttccaagc tcatcggacg   1080

ttctttgcgg acggtccaat acgcagtcaa ggacttggtg gccgagcgct ggatctccgt   1140
```

```
cgtgaagctc aacggccccg gcaccgtgtc ggcctacgtg gtcaatgacc gcgtggcgtg   1200

gggccagccc cgcgaccagt tgcgcctgtc ggtgttcagt gccgccgtgg tggttgatca   1260

cgacgaccag gacgaatcgc tgttggggca tggcgacctg cgccgcatcc cgaccctgta   1320

tccgggcgag cagcaactac cgaccggccc cggcgaggag ccgcccagcc agcccggcat   1380

tccgggcatg gaaccagacc tgccagcctt gaccgaaacg gaggaatggg aacggcgcgg   1440

gcagcagcgc ctgccgatgc ccgatgagcc gtgttttctg gacgatggcg agccgttgga   1500

gccgccgaca cgggtcacgc tgccgcgccg gtagtacgta agaggttcca actttcacca   1560

taatgaaata agatcactac cgggcgtatt ttttgagtta tcgagatttt caggagctaa   1620

ggaagctaaa atgagccata ttcaacggga aacgtcttgc tcgaggccgc gattaaattc   1680

caacatggat gctgatttat atgggtataa atgggctcgc gataatgtcg ggcaatcagg   1740

tgcgacaatc tatcgattgt atgggaagcc cgatgcgcca gagttgtttc tgaaacatgg   1800

caaaggtagc gttgccaatg atgttacaga tgagatggtc aggctaaact ggctgacgga   1860

atttatgcct cttccgacca tcaagcattt tatccgtact cctgatgatg catggttact   1920

caccactgcg atccccagga aaacagcatt ccaggtatta gaagaatatc ctgattcagg   1980

tgaaaatatt gttgatgcgc tggcagtgtt cctgcgccgg ttgcattcga ttcctgtttg   2040

taattgtcct tttaacggcg atcgcgtatt tcgtctcgct caggcgcaat cacgaatgaa   2100

taacggtttg gttggtgcga gtgattttga tgacgagcgt aatggctggc ctgttgaaca   2160

agtctggaaa gaaatgcata agcttttgcc attctcaccg gattcagtcg tcactcatgg   2220

tgatttctca cttgataacc ttatttttga cgaggggaaa ttaataggtt gtattgatgt   2280

tggacgagtc ggaatcgcag accgatacca ggatcttgcc atcctatgga actgcctcgg   2340

tgagttttct ccttcattac agaaacggct ttttcaaaaa tatggtattg ataatcctga   2400

tatgaataaa ttgcagtttc acttgatgct cgatgagttt ttctgagggc ggatccccct   2460

caagtcaaaa gcctccggtc ggaggctttt gactttctgc tatggaggtc aggtatgatt   2520

taaatggtca gtattgagcg atatctagag aattcgtc                           2558
```

<210> SEQ ID NO 9
<211> LENGTH: 2404
<212> TYPE: DNA
<213> ORGANISM: Escherichia coli

<400> SEQUENCE: 9

```
aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180

cgagcttgac cacagggatt gcccaccggc tacccagcct tcgaccacat acccaccggc    240

tccaactgcg cggcctgcgg ccttgcccca tcaatttttt taattttctc tggggaaaag    300

cctccggcct gcggcctgcg cgcttcgctt gccggttgga caccaagtgg aaggcgggtc    360

aaggctcgcg cagcgaccgc gcagcggctt ggccttgacg cgcctggaac gacccaagcc    420

tatgcgagtg gggcagtcg aaggcgaagc ccgcccgcct gccccccgag cctcacggcg     480

gcgagtgcgg gggttccaag gggcagcgc caccttgggc aaggccgaag gccgcgcagt     540

cgatcaacaa gccccggagg ggccactttt tgccggaggg ggagccgcgc cgaaggcgtg    600

ggggaacccc gcaggggtgc ccttctttgg gcaccaaaga actagatata gggcgaaatg    660
```

-continued

```
cgaaagactt aaaaatcaac aacttaaaaa aggggggtac gcaacagctc attgcggcac    720

cccccgcaat agctcattgc gtaggttaaa gaaaatctgt aattgactgc cacttttacg    780

caacgcataa ttgttgtcgc gctgccgaaa agttgcagct gattgcgcat ggtgccgcaa    840

ccgtgcggca ccctaccgca tggagataag catggccacg cagtccagag aaatcggcat    900

tcaagccaag aacaagcccg gtcactgggt gcaaacggaa cgcaaagcgc atgaggcgtg    960

ggccgggctt attgcgagga aacccacggc ggcaatgctg ctgcatcacc tcgtggcgca   1020

gatgggccac cagaacgccg tggtggtcag ccagaagaca ctttccaagc tcatcggacg   1080

ttctttgcgg acggtccaat acgcagtcaa ggacttggtg gccgagcgct ggatctccgt   1140

cgtgaagctc aacggccccg gcaccgtgtc ggcctacgtg gtcaatgacc gcgtggcgtg   1200

gggccagccc cgcgaccagt tgcgcctgtc ggtgttcagt gccgccgtgg tggttgatca   1260

cgacgaccag gacgaatcgc tgttggggca tggcgacctg cgccgcatcc cgaccctgta   1320

tccgggcgag cagcaactac cgaccggccc cggcgaggag ccgcccagcc agcccggcat   1380

tccgggcatg gaaccagacc tgccagcctt gaccgaaacg gaggaatggg aacggcgcgg   1440

gcagcagcgc ctgccgatgc ccgatgagcc gtgttttctg gacgatggcg agccgttgga   1500

gccgccgaca cgggtcacgc tgccgcgccg gtagtacgta agaggttcca actttcacca   1560

taatgaaata agatcactac cgggcgtatt ttttgagtta tcgagatttt caggagctaa   1620

ggaagctaaa atggagaaaa aaatcactgg atataccacc gttgatatat cccaatggca   1680

tcgtaaagaa cattttgagg catttcagtc agttgctcaa tgtacctata accagaccgt   1740

tcagctggat attacggcct ttttaaagac cgtaaagaaa aataagcaca agttttatcc   1800

ggcctttatt cacattcttg cccgcctgat gaatgctcat ccggaattcc gtatggcaat   1860

gaaagacggt gagctggtga tatgggatag tgttcaccct tgttacaccg ttttccatga   1920

gcaaactgaa acgttttcat cgctctggag tgaataccac gacgatttcc ggcagtttct   1980

acacatatat tcgcaagatg tggcgtgtta cggtgaaaac ctggcctatt tccctaaagg   2040

gtttattgag aatatgtttt tcgtctcagc caatccctgg gtgagtttca ccagttttga   2100

tttaaacgtg gccaatatgg acaacttctt cgcccccgtt ttcaccatgg gcaaatatta   2160

tacgcaaggc gacaaggtgc tgatgccgct ggcgattcag gttcatcatg ccgtttgtga   2220

tggcttccat gtcggcagaa tgcttaatga attacaacag tactgcgatg agtggcaggg   2280

cggggcgtaa acgcgtggat ccccctcaag tcaaaagcct ccggtcggag gcttttgact   2340

ttctgctatg gaggtcaggt atgatttaaa tggtcagtat tgagcgatat ctagagaatt   2400

cgtc                                                                2404
```

<210> SEQ ID NO 10
<211> LENGTH: 2936
<212> TYPE: DNA
<213> ORGANISM: Escherichia coli

<400> SEQUENCE: 10

```
aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180

cgagcttgac cacagggatt gcccaccggc tacccagcct tcgaccacat acccaccggc    240

tccaactgcg cggcctgcgg ccttgcccca tcaatttttt taattttctc tggggaaaag    300

cctccggcct gcggcctgcg cgcttcgctt gccggttgga caccaagtgg aaggcgggtc    360
```

-continued

```
aaggctcgcg cagcgaccgc gcagcggctt ggccttgacg cgcctggaac gacccaagcc    420
tatgcgagtg ggggcagtcg aaggcgaagc ccgcccgcct gccccccgag cctcacggcg    480
gcgagtgcgg gggttccaag ggggcagcgc caccttgggc aaggccgaag gccgcgcagt    540
cgatcaacaa gccccggagg ggccactttt tgccggaggg ggagccgcgc cgaaggcgtg    600
ggggaacccc gcaggggtgc ccttctttgg gcaccaaaga actagatata gggcgaaatg    660
cgaaagactt aaaaatcaac aacttaaaaa agggggggtac gcaacagctc attgcggcac    720
cccccgcaat agctcattgc gtaggttaaa gaaaatctgt aattgactgc cacttttacg    780
caacgcataa ttgttgtcgc gctgccgaaa agttgcagct gattgcgcat ggtgccgcaa    840
ccgtgcggca ccctaccgca tggagataag catggccacg cagtccagag aaatcggcat    900
tcaagccaag aacaagcccg gtcactgggt gcaaacggaa cgcaaagcgc atgaggcgtg    960
ggccgggctt attgcgagga aacccacggc ggcaatgctg ctgcatcacc tcgtggcgca   1020
gatgggccac cagaacgccg tggtggtcag ccagaagaca ctttccaagc tcatcggacg   1080
ttctttgcgg acggtccaat acgcagtcaa ggacttggtg gccgagcgct ggatctccgt   1140
cgtgaagctc aacggccccg gcaccgtgtc ggcctacgtg gtcaatgacc gcgtggcgtg   1200
gggccagccc cgcgaccagt tgcgcctgtc ggtgttcagt gccgccgtgg tggttgatca   1260
cgacgaccag gacgaatcgc tgttggggca tggcgacctg cgccgcatcc cgaccctgta   1320
tccgggcgag cagcaactac cgaccggccc cggcgaggag ccgcccagcc agcccggcat   1380
tccgggcatg gaaccagacc tgccagcctt gaccgaaacg gaggaatggg aacggcgcgg   1440
gcagcagcgc ctgccgatgc ccgatgagcc gtgttttctg gacgatggcg agccgttgga   1500
gccgccgaca cgggtcacgc tgccgcgccg gtagtacgta agaggttcca actttcacca   1560
taatgaaata agatcactac cgggcgtatt ttttgagtta tcgagatttt caggagctaa   1620
ggaagctaaa atgaaatcta acaatgcgct catcgtcatc ctcggcaccg tcaccctgga   1680
tgctgtaggc ataggcttgg ttatgccggt actgccgggc ctcttgcggg atatcgtcca   1740
ttccgacagc atcgccagtc actatggcgt gctgctagcg ctatatgcgt tgatgcaatt   1800
tctatgcgca cccgttctcg gagcactgtc cgaccgcttt ggccgccgcc cagtcctgct   1860
cgcttcgcta cttggagcca ctatcgacta cgcgatcatg gcgaccacac ccgtcctgtg   1920
gatcctctac gccggacgca tcgtggccgg catcaccggc gccacaggtg cggttgctgg   1980
cgcctatatc gccgacatca ccgatgggga agatcgggct cgccacttcg ggctcatgag   2040
cgcttgtttc ggcgtgggta tggtggcagg ccccgtggcc gggggactgt tgggcgccat   2100
ctccttgcat gcaccattcc ttgcggcggc ggtgctcaac ggcctcaacc tactactggg   2160
ctgcttccta atgcaggagt cgcataaggg agagcgtcga ccgatgccct tgagagcctt   2220
caacccagtc agctccttcc ggtgggcgcg gggcatgact atcgtcgccg cacttatgac   2280
tgtcttcttt atcatgcaac tcgtaggaca ggtgccggca gcgctctggg tcattttcgg   2340
cgaggaccgc tttcgctgga gcgcgacgat gatcggcctg tcgcttgcgg tattcggaat   2400
cttgcacgcc ctcgctcaag ccttcgtcac tggtcccgcc accaaacgtt tcggcgagaa   2460
gcaggccatt atcgccggca tggcggccga cgcgctgggc tacgtcttgc tggcgttcgc   2520
gacgcgaggc tggatggcct tccccattat gattcttctc gcttccggcg gcatcgggat   2580
gcccgcgttg caggccatgc tgtccaggca ggtagatgac gaccatcagg gacagcttca   2640
aggatcgctc gcggctctta ccagcctaac ttcgatcact ggaccgctga tcgtcacggc   2700
```

-continued

```
gatttatgcc gcctcggcga gcacatggaa cgggttggca tggattgtag gcgccgccct   2760

ataccttgtc tgcctccccg cgttgcgtcg cggtgcatgg agccgggcca cctcgacctg   2820

aatggaaggg atccccctca agtcaaaagc ctccggtcgg aggcttttga ctttctgcta   2880

tggaggtcag gtatgattta aatggtcagt attgagcgat atctagagaa ttcgtc       2936
```

<210> SEQ ID NO 11
<211> LENGTH: 1979
<212> TYPE: DNA
<213> ORGANISM: Escherichia coli

<400> SEQUENCE: 11

```
aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180

cgagcttgac cacagggatt gcccaccggc tacccagcct tcgaccacat acccaccggc    240

tccaactgcg cggcctgcgg ccttgcccca tcaatttttt taattttctc tggggaaaag    300

cctccggcct gcggcctgcg cgcttcgctt gccggttgga caccaagtgg aaggcgggtc    360

aaggctcgcg cagcgaccgc gcagcggctt ggccttgacg cgcctggaac gacccaagcc    420

tatgcgagtg gggcagtcg aaggcgaagc ccgcccgcct gccccccgag cctcacggcg    480

gcgagtgcgg gggttccaag gggcagcgc caccttgggc aaggccgaag gccgcgcagt    540

cgatcaacaa gccccggagg ggccactttt tgccggaggg ggagccgcgc cgaaggcgtg    600

ggggaacccc gcaggggtgc ccttctttgg gcaccaaaga actagatata gggcgaaatg    660

cgaaagactt aaaaatcaac aacttaaaaa aggggggtac gcaacagctc attgcggcac    720

cccccgcaat agctcattgc gtaggttaaa gaaaatctgt aattgactgc cacttttacg    780

caacgcataa ttgttgtcgc gctgccgaaa agttgcagct gattgcgcat ggtgccgcaa    840

ccgtgcggca ccctaccgca tggagataag catggccacg cagtccagag aaatcggcat    900

tcaagccaag aacaagcccg gtcactgggt gcaaacggaa cgcaaagcgc atgaggcgtg    960

ggccgggctt attgcgagga aacccacggc ggcaatgctg ctgcatcacc tcgtggcgca   1020

gatgggccac cagaacgccg tggtggtcag ccagaagaca ctttccaagc tcatcggacg   1080

ttctttgcgg acggtccaat acgcagtcaa ggacttggtg gccgagcgct ggatctccgt   1140

cgtgaagctc aacggccccg gcaccgtgtc ggcctacgtg gtcaatgacc gcgtggcgtg   1200

gggccagccc cgcgaccagt tgcgcctgtc ggtgttcagt gccgccgtgg tggttgatca   1260

cgacgaccag gacgaatcgc tgttggggca tggcgacctg cgccgcatcc cgaccctgta   1320

tccgggcgag cagcaactac cgaccggccc cggcgaggag ccgcccagcc agcccggcat   1380

tccgggcatg gaaccagacc tgccagcctt gaccgaaacg gaggaatggg aacggcgcgg   1440

gcagcagcgc ctgccgatgc ccgatgagcc gtgttttctg gacgatggcg agccgttgga   1500

gccgccgaca cgggtcacgc tgccgcgccg gtagtacgta agaggttcca actttcacca   1560

taatgaaata agatcactac cgggcgtatt ttttgagtta tcgagatttt caggagctaa   1620

ggaagctaaa atgggtcaaa gtagcgatga agccaacgct cccgttgcag ggcagtttgc   1680

gcttcccctg agtgccacct ttggcttagg ggatcgcgta cgcaagaaat ctggtgccgc   1740

ttggcagggt caagtcgtcg gttggtattg cacaaaactc actcctgaag gctatgcggt   1800

cgagtccgaa tcccacccag gctcagtgca aatttatcct gtggctgcac ttgaacgtgt   1860

ggcctaagaa tggatccccc tcaagtcaaa agcctccggt cggaggcttt tgactttctg   1920
```

```
ctatggaggt caggtatgat ttaaatggtc agtattgagc gatatctaga gaattcgtc    1979


<210> SEQ ID NO 12
<211> LENGTH: 4617
<212> TYPE: DNA
<213> ORGANISM: Escherichia coli

<400> SEQUENCE: 12

aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180

cgagcttgac cacagggatt gcccaccggc tacccagcct tcgaccacat acccaccggc    240

tccaactgcg cggcctgcgg ccttgcccca tcaatttttt taattttctc tggggaaaag    300

cctccggcct gcggcctgcg cgcttcgctt gccggttgga caccaagtgg aaggcgggtc    360

aaggctcgcg cagcgaccgc gcagcggctt ggccttgacg cgcctggaac gacccaagcc    420

tatgcgagtg ggggcagtcg aaggcgaagc ccgcccgcct gccccccgag cctcacggcg    480

gcgagtgcgg gggttccaag ggggcagcgc caccttgggc aaggccgaag gccgcgcagt    540

cgatcaacaa gccccggagg ggccactttt tgccggaggg ggagccgcgc cgaaggcgtg    600

ggggaacccc gcaggggtgc ccttctttgg gcaccaaaga actagatata gggcgaaatg    660

cgaaagactt aaaaatcaac aacttaaaaa aggggggtac gcaacagctc attgcggcac    720

cccccgcaat agctcattgc gtaggttaaa gaaaatctgt aattgactgc cacttttacg    780

caacgcataa ttgttgtcgc gctgccgaaa agttgcagct gattgcgcat ggtgccgcaa    840

ccgtgcggca ccctaccgca tggagataag catggccacg cagtccagag aaatcggcat    900

tcaagccaag aacaagcccg gtcactgggt gcaaacggaa cgcaaagcgc atgaggcgtg    960

ggccgggctt attgcgagga aacccacggc ggcaatgctg ctgcatcacc tcgtggcgca   1020

gatgggccac cagaacgccg tggtggtcag ccagaagaca ctttccaagc tcatcggacg   1080

ttctttgcgg acggtccaat acgcagtcaa ggacttggtg gccgagcgct ggatctccgt   1140

cgtgaagctc aacggccccg gcaccgtgtc ggcctacgtg gtcaatgacc gcgtggcgtg   1200

ggccagccc cgcgaccagt tgcgcctgtc ggtgttcagt gccgccgtgg tggttgatca   1260

cgacgaccag gacgaatcgc tgttggggca tggcgacctg cgccgcatcc cgaccctgta   1320

tccgggcgag cagcaactac cgaccggccc cggcgaggag ccgcccagcc agcccggcat   1380

tccgggcatg gaaccagacc tgccagcctt gaccgaaacg gaggaatggg aacggcgcgg   1440

gcagcagcgc ctgccgatgc ccgatgagcc gtgttttctg gacgatggcg agccgttgga   1500

gccgccgaca cgggtcacgc tgccgcgccg gtagtacgta agaggttcca actttcacca   1560

taatgaaata agatcactac cgggcgtatt ttttgagtta tcgagatttt caggagctaa   1620

ggaagctaaa atggaagaac aaagcgtgaa catggcgcga ttgaaggggg aggttttgcc   1680

cgccctcttc gcgtcgccgg cgacgattgg cgagtacggg gccggcatcg acggggcgga   1740

ttccctcaac gagctgtcga atctgatgga gcacggcgca gttgccgcgc tggccgacaa   1800

aatcagccag atcgtggcga agctggccga cgcggacccc cgcaagatcg cggaaaagcc   1860

tacctggttc gagaagatgc ttggccgtga ggttgaacgc caggtgaggt atcaggtcgc   1920

ccgcaagacg ctcgaccagt tgctggacga agccgagggc gtagcgcagc gcgtgcggga   1980

cacgttgcgc gccttggatg acatgctcaa tacgcatgag gccgaggtag accggctcag   2040
```

-continued

```
agcctacatt caagccgggc gcgagttcct ggacgagaac cccgaggccg gcgcggccaa   2100

ggccggcgtg atcgagttcg acaagccgcg cgaacgcttc gcgcgcaagc tcgccaacct   2160

ggcaaccctc atggcgtccc atgaaatgag cgtcactcag atgaagctca cgcgggcgca   2220

ggccgtggac atgctggacc gcttctctga aacggcatcc gtcctggtgc ccgtctggcg   2280

tcagcacacc ctcgcgctca tcaccaccaa gaacatgaat ccggcaatgg tcgccgaggc   2340

ggccaaagct caccaggcgc tcatgcggag cctttcgcag agcctggaag gcatcaacca   2400

ataacacggc gggagaaccc tatgaacgca ctgaaaacga cgcacgacgc caaggcccct   2460

atcgtcgcct tcgacatgac cccggcaacc ctgcgcgagc tgggcttgca ggaaagcgac   2520

gtgccggaag tccatgcggt cgcgcagcgg atcgaggtcg gcagtccgca gaccgttgcc   2580

gagttcggcc gcgacgtggc cgagcacacg tcccgctacg ccgatagcct gctggaccag   2640

gtgcgcaaca gcgacctgga cgaagcaggc gagaaactga cccaggttgt cgccaaggcc   2700

cgttccctga acgtcggccc tttgtccgac aaccgttccc gcctgcccct gattggcccg   2760

ctgatcgacc gcttccgcgt ccgttcgacg ggcttcatgg cgcgcttcga cacgacccgc   2820

gagcagatcg aacacctggt cagcgaagtg cagaccaccc agcaaggcat cgcgcagcgc   2880

aatgcctcgc tcgacgaaat gttcgcagcc gtgcgcgagg aacaccgcct tcttggcgtc   2940

cacatcgcgg ccggcaaggt ccgccttgcc gagctgcgcg agcaggccga gggtctgcgc   3000

ggcaatgtcg ggaacgaccc gggccgcgtg caggagctgg ccgacctcga tgcgatggtt   3060

gccaacctgg acaagcgcat cggcgacctg atcgccttgc aacattcggc catgcagagc   3120

ctgccgacca tccgcatgat ccaggccaac aaccagatgc tggtcgataa attccacacc   3180

atccgcgaaa tcaccgtgcc ggcgtggaag cggcaattca tgctggcctt gagcctcaac   3240

gagcagaaga acgccgtcga actggccacg gccatcgacg acaccaccaa cgacctgatg   3300

aagcgcaatg cggccctgct gcatcgcacg tccgtcgaga cggcgaagga gaaccaacgc   3360

ctggtgatcg acgtggacac gctcaagcag gttcagacga cgctcatcaa gaccgtcgag   3420

gacgttattc gcatccagca ggaaggcgtg cagaagcgca aggatgccga gaagcagatc   3480

gccgcaatgc gtggcgatct tcaagccaag ctgacccgcc agcccgtgcg cgagctggcc   3540

caacaggagt ccgtatgaat gccacaaaca ccgatgtttt cgcccaggta ggcggcctcg   3600

aggcccgagg cgcgaagatg aagaagcggg gcacccgctt cctcatcgcg gcgctggcag   3660

tccttgccat tgccgggatc ggggcagtaa cgggatgggc gatcagcccg agcgcgacgc   3720

ccggaagcat tgacgtgccg caggtgctgg catcgacatt cagcgaccag gtgccgggca   3780

gtgagggcgg cggcctgggt ggcggcctgc ccttcacttc ggccgtcggg gcattcacgg   3840

acttcatggc ggggccggca atttttacct tgggcattct tggcatagtg gtcgcgggtg   3900

ccgtgctcgt gttcgggggt gaattctgcg ggttcgtgcg atccgtctgc atgatggtga   3960

tagccgtcag catgattttc gtgtcgtcga acttggtgaa gggcattctc ggcggcgatc   4020

acgacgccgg ccctgcggag ccttcgccgc gtgcgcgatt catggcggcc gtggaggcca   4080

aggatttcgc gcgagtgcaa gagctgatcg aggcgcgtgg agccaagtcg gcggctgatt   4140

atgtccttgc gcagctcgcc gtggccgaag gtctggaccg caagcctggt gcgcgcgtcg   4200

tggtcgggaa agcggcgggc agcatggcaa tgccgcctgc ggcgctgggt tttacgccaa   4260

ggggagaagc ggcatacgcc atcgagcggt cagcctatgg tgagccgagg tccagcattg   4320

cgaagcagta ccagcaggaa tggaaccgga aggcggcgac ctggtgggcg atggccggtg   4380

tggccggcat catcggcgcg atcctggcgg cggcggcaac cggctttgtt gggctggcag   4440
```

-continued

```
tgtcgatccg caaccgagtg aagcgcgtgc gcgacctgtt ggtgatggag ccgggtgcag   4500

agccataagg gatccccctc aagtcaaaag cctccggtcg gaggcttttg actttctgct   4560

atggaggtca ggtatgattt aaatggtcag tattgagcga tatctagaga attcgtc      4617
```

<210> SEQ ID NO 13
<211> LENGTH: 5029
<212> TYPE: DNA
<213> ORGANISM: Escherichia coli

<400> SEQUENCE: 13

```
aacgaattca agcttgatat cattcaggac gagcctcaga ctccagcgta actggactga     60

aaacaaacta aagcgccctt gtggcgcttt agttttgttc cgctcatgat aataatggtt    120

tcttagacgt caggtggcac ttttcgggga aatgtgcgcg cccgcgttcc tgctggcgct    180

gggcctgttt ctggcgctgg acttcccgct gttccgtcag cagcttttcg cccacggcct    240

tgatgatcgc ggcggccttg gcctgcatat cccgattcaa cggccccagg gcgtccagaa    300

cgggcttcag gcgctcccga aggtctcggg ccgtctcttg ggcttgatcg gccttcttgc    360

gcatctcacg cgctcctgcg gcggcctgta gggcaggctc atacccctgc cgaaccgctt    420

ttgtcagccg gtcggccacg gcttccggcg tctcaacgcg ctttgagatt cccagctttt    480

cggccaatcc ctgcggtgca taggcgcgtg gctcgaccgc ttgcgggctg atggtgacgt    540

ggcccactgg tggccgctcc agggcctcgt agaacgcctg aatgcgcgtg tgacgtgcct    600

tgctgccctc gatgccccgt tgcagcccta gatcggccac agcggccgca aacgtggtct    660

ggtcgcgggt catctgcgct ttgttgccga tgaactcctt ggccgacagc ctgccgtcct    720

gcgtcagcgg caccacgaac gcggtcatgt gcgggctggt ttcgtcacgg tggatgctgg    780

ccgtcacgat gcgatccgcc ccgtacttgt ccgccagcca cttgtgcgcc ttctcgaaga    840

acgccgcctg ctgttcttgg ctggccgact tccaccattc cgggctggcc gtcatgacgt    900

actcgaccgc caacacagcg tccttgcgcc gcttctctgg cagcaactcg cgcagtcggc    960

ccatcgcttc atcggtgctg ctggccgccc agtgctcgtt ctctggcgtc ctgctggcgt   1020

cagcgttggg cgtctcgcgc tcgcggtagg cgtgcttgag actggccgcc acgttgccca   1080

ttttcgccag cttcttgcat cgcatgatcg cgtatgccgc catgcctgcc cctccctttt   1140

ggtgtccaac cggctcgacg gggcagcgc aaggcggtgc ctccggcggg ccactcaatg    1200

cttgagtata ctcactagac tttgcttcgc aaagtcgtga ccgcctacgg cggctgcggc   1260

gccctacggg cttgctctcc gggcttcgcc ctgcgcggtc gctgcgctcc cttgccagcc   1320

cgtggatatg tggacgatgg ccgcgagcgg ccaccggctg gctcgcttcg ctcggcccgt   1380

ggacaaccct gctggacaag ctgatggaca ggctgcgcct gcccacgagc ttgaccacag   1440

ggattgccca ccggctaccc agccttcgac cacataccca ccggctccaa ctgcgcggcc   1500

tgcggccttg ccccatcaat ttttttaatt ttctctgggg aaaagcctcc ggcctgcggc   1560

ctgcgcgctt cgcttgccgg ttggacacca agtggaaggc gggtcaaggc tcgcgcagcg   1620

accgcgcagc ggcttggcct tgacgcgcct ggaacgaccc aagcctatgc gagtgggggc   1680

agtcgaaggc gaagcccgcc cgcctgcccc ccgagcctca cggcggcgag tgcgggggtt   1740

ccaagggggc agcgccacct tgggcaaggc cgaaggccgc gcagtcgatc aacaagcccc   1800

ggaggggcca ctttttgccg gagggggagc cgcgccgaag gcgtggggga accccgcagg   1860

ggtgcccttc tttgggcacc aaagaactag atatagggcg aaatgcgaaa gacttaaaaa   1920
```

-continued

```
tcaacaactt aaaaaagggg ggtacgcaac agctcattgc ggcacccccc gcaatagctc   1980
attgcgtagg ttaaagaaaa tctgtaattg actgccactt ttacgcaacg cataattgtt   2040
gtcgcgctgc cgaaaagttg cagctgattg cgcatggtgc cgcaaccgtg cggcacccta   2100
ccgcatggag ataagcatgg ccacgcagtc cagagaaatc ggcattcaag ccaagaacaa   2160
gcccggtcac tgggtgcaaa cggaacgcaa agcgcatgag gcgtgggccg ggcttattgc   2220
gaggaaaccc acggcggcaa tgctgctgca tcacctcgtg gcgcagatgg gccaccagaa   2280
cgccgtggtg gtcagccaga agacactttc caagctcatc ggacgttctt tgcggacggt   2340
ccaatacgca gtcaaggact tggtggccga gcgctggatc tccgtcgtga agctcaacgg   2400
ccccggcacc gtgtcggcct acgtggtcaa tgaccgcgtg gcgtggggcc agccccgcga   2460
ccagttgcgc ctgtcggtgt tcagtgccgc cgtggtggtt gatcacgacg accaggacga   2520
atcgctgttg gggcatggcg acctgcgccg catcccgacc ctgtatccgg gcgagcagca   2580
actaccgacc ggccccggcg aggagccgcc cagccagccc ggcattccgg gcatggaacc   2640
agacctgcca gccttgaccg aaacggagga atgggaacgg cgcgggcagc agcgcctgcc   2700
gatgcccgat gagccgtgtt ttctggacga tggcgagccg ttggagccgc cgacacgggt   2760
cacgctgccg cgccggtagt acgtaagagg ttccaacttt caccataatg aaataagatc   2820
actaccgggc gtattttttg agttatcgag attttcagga gctaaggaag ctaaaatgag   2880
tattcaacat ttccgtgtcg cccttattcc cttttttgcg gcattttgcc ttcctgtttt   2940
tgctcaccca gaaacgctgg tgaaagtaaa agatgctgaa gatcagttgg gtgcacgagt   3000
gggttacatc gaactggatc tcaacagcgg taagatcctt gagagtttac gccccgaaga   3060
acgttttcca atgatgagca cttttaaagt tctgctatgt ggcgcggtat tatcccgtat   3120
tgacgccggg caagagcaac tcggtcgccg catacactat tctcagaatg acttggttga   3180
gtactcacca gtcacagaaa agcatctcac ggatggcatg acagtaagag aattatgcag   3240
tgctgccata accatgagtg ataacactgc ggccaactta cttctggcaa cgatcggagg   3300
accgaaggag ctaaccgctt ttttgcacaa catgggggat catgtaactc gccttgatcg   3360
ttgggaaccg gagctgaatg aagccatacc aaacgacgag cgtgacacca cgatgcctgt   3420
agcaatggca acaacgttgc gcaaactatt aactggcgaa ctacttactc tagcttcccg   3480
gcaacaatta atagactgga tggaggcgga taaagttgca ggatcacttc tgcgctcggc   3540
cctcccggct ggctggttta ttgctgataa atctggagcc ggtgagcgtg ggtctcgcgg   3600
tatcattgca gcactggggc cagatggtaa gccctcccgc atcgtagtta tctacacgac   3660
ggggagtcag gcaactatgg atgaacgaaa tagacagatc gctgagatag gtgcctcact   3720
gattaagcat tggtaatgag gatccccctc aagtcaaaag cctccggtcg gaggcttttg   3780
actttctgct atggaggtca ggtatgattt ttatgacaac ttgacggcta catcattcac   3840
tttttcttca caaccggcac ggaactcgct cgggctggcc ccggtgcatt ttttaaatac   3900
ccgcgagaaa tagagttgat cgtcaaaacc aacattgcga ccgacggtgg cgataggcat   3960
ccgggtggtg ctcaaaagca gcttcgcctg gctgatacgt tggtcctcgc gccagcttaa   4020
gacgctaatc cctaactgct ggcggaaaag atgtgacaga cgcgacggcg acaagcaaac   4080
atgctgtgcg acgctggcga tatcaaaatt gctgtctgcc aggtgatcgc tgatgtactg   4140
acaagcctcg cgtacccgat tatccatcgg tggatggagc gactcgttaa tcgcttccat   4200
gcgccgcagt aacaattgct caagcagatt tatcgccagc agctccgaat agcgcccttc   4260
cccttgcccg gcgttaatga tttgcccaaa caggtcgctg aaatgcggct ggtgcgcttc   4320
```

-continued atccgggcga aagaaccccg tattggcaaa tattgacggc cagttaagcc attcatgcca 4380
gtaggcgcgc ggacgaaagt aaacccactg gtgataccat tcgcgagcct ccggatgacg 4440
accgtagtga tgaatctctc ctggcgggaa cagcaaaata tcacccggtc ggcaaacaaa 4500
ttctcgtccc tgatttttca ccaccccctg accgcgaatg gtgagattga gaatataacc 4560
tttcattccc agcggtcggt cgataaaaaa atcgagataa ccgttggcct caatcggcgt 4620
taaacccgcc accagatggg cattaaacga gtatcccggc agcaggggat cattttgcgc 4680
ttcagccata cttttcatac tcccgccatt cagagaagaa accaattgtc catattgcat 4740
cagacattgc cgtcactgcg tcttttactg gctcttctcg ctaaccaaac cggtaacccc 4800
gcttattaaa agcattctgt aacaaagcgg gaccaaagcc atgacaaaaa cgcgtaacaa 4860
aagtgtctat aatcacggca gaaaagtcca cattgattat ttgcacggcg tcacactttg 4920
ctatgccata gcatttttat ccataagatt agcggatcct acctgacgct tttatcgca 4980 actctctact gtttctccat acccgttttt ttgggctaga gaattcgtc 5029

<210> SEQ ID NO 14
<211> LENGTH: 4985
<212> TYPE: DNA
<213> ORGANISM: Escherichia coli

<400> SEQUENCE: 14
aacgaattca agcttgatat cattcaggac gagcctcaga ctccagcgta actggactga 60
aaacaaacta aagcgccctt gtggcgcttt agttttgttc cgctcatgat aataatggtt 120
tcttagacgt caggtggcac ttttcgggga aatgtgcgcg cccgcgttcc tgctggcgct 180
gggcctgttt ctggcgctgg acttcccgct gttccgtcag cagcttttcg cccacggcct 240
tgatgatcgc ggcggccttg gcctgcatat cccgattcaa cggccccagg gcgtccagaa 300
cgggcttcag gcgctcccga aggtctcggg ccgtctcttg ggcttgatcg gccttcttgc 360
gcatctcacg cgctcctgcg gcggcctgta gggcaggctc atacccctgc cgaaccgctt 420
ttgtcagccg gtcggccacg gcttccggcg tctcaacgcg ctttgagatt cccagctttt 480
cggccaatcc ctgcggtgca taggcgcgtg gctcgaccgc ttgcgggctg atggtgacgt 540
ggcccactgg tggccgctcc agggcctcgt agaacgcctg aatgcgcgtg tgacgtgcct 600
tgctgccctc gatgccccgt tgcagcccta gatcggccac agcggccgca aacgtggtct 660
ggtcgcgggt catctgcgct ttgttgccga tgaactcctt ggccgacagc ctgccgtcct 720
gcgtcagcgg caccacgaac gcggtcatgt gcgggctggt ttcgtcacgg tggatgctgg 780
ccgtcacgat gcgatccgcc ccgtacttgt ccgccagcca cttgtgcgcc ttctcgaaga 840
acgccgcctg ctgttcttgg ctggccgact tccaccattc cgggctggcc gtcatgacgt 900
actcgaccgc caacacagcg tccttgcgcc gcttctctgg cagcaactcg cgcagtcggc 960
ccatcgcttc atcggtgctg ctggccgccc agtgctcgtt ctctggcgtc ctgctggcgt 1020
cagcgttggg cgtctcgcgc tcgcggtagg cgtgcttgag actggccgcc acgttgccca 1080
ttttcgccag cttcttgcat cgcatgatcg cgtatgccgc catgcctgcc cctccctttt 1140
ggtgtccaac cggctcgacg ggggcagcgc aaggcggtgc ctccggcggg ccactcaatg 1200
cttgagtata ctcactagac tttgcttcgc aaagtcgtga ccgcctacgg cggctgcggc 1260
gccctacggg cttgctctcc gggcttcgcc ctgcgcggtc gctgcgctcc cttgccagcc 1320
cgtggatatg tggacgatgg ccgcgagcgg ccaccggctg gctcgcttcg ctcggcccgt 1380

-continued

```
ggacaaccct gctggacaag ctgatggaca ggctgcgcct gcccacgagc ttgaccacag   1440
ggattgccca ccggctaccc agccttcgac cacataccca ccggctccaa ctgcgcggcc   1500
tgcggccttg ccccatcaat ttttttaatt ttctctgggg aaaagcctcc ggcctgcggc   1560
ctgcgcgctt cgcttgccgg ttggacacca agtggaaggc gggtcaaggc tcgcgcagcg   1620
accgcgcagc ggcttggcct tgacgcgcct ggaacgaccc aagcctatgc gagtgggggc   1680
agtcgaaggc gaagcccgcc cgcctgcccc ccgagcctca cggcggcgag tgcgggggtt   1740
ccaagggggc agcgccacct tgggcaaggc cgaaggccgc gcagtcgatc aacaagcccc   1800
ggaggggcca ctttttgccg gagggggagc cgcgccgaag gcgtggggga accccgcagg   1860
ggtgcccttc tttgggcacc aaagaactag atatagggcg aaatgcgaaa gacttaaaaa   1920
tcaacaactt aaaaaagggg ggtacgcaac agctcattgc ggcacccccc gcaatagctc   1980
attgcgtagg ttaaagaaaa tctgtaattg actgccactt ttacgcaacg cataattgtt   2040
gtcgcgctgc cgaaaagttg cagctgattg cgcatggtgc cgcaaccgtg cggcacccta   2100
ccgcatggag ataagcatgg ccacgcagtc cagagaaatc ggcattcaag ccaagaacaa   2160
gcccggtcac tgggtgcaaa cggaacgcaa agcgcatgag gcgtgggccg ggcttattgc   2220
gaggaaaccc acggcggcaa tgctgctgca tcacctcgtg gcgcagatgg gccaccagaa   2280
cgccgtggtg gtcagccaga agacactttc caagctcatc ggacgttctt tgcggacggt   2340
ccaatacgca gtcaaggact tggtggccga gcgctggatc tccgtcgtga agctcaacgg   2400
ccccggcacc gtgtcggcct acgtggtcaa tgaccgcgtg gcgtggggcc agccccgcga   2460
ccagttgcgc ctgtcggtgt tcagtgccgc cgtggtggtt gatcacgacg accaggacga   2520
atcgctgttg gggcatggcg acctgcgccg catcccgacc ctgtatccgg gcgagcagca   2580
actaccgacc ggccccggcg aggagccgcc cagccagccc ggcattccgg gcatggaacc   2640
agacctgcca gccttgaccg aaacggagga atgggaacgg cgcgggcagc agcgcctgcc   2700
gatgcccgat gagccgtgtt ttctggacga tggcgagccg ttggagccgc cgacacgggt   2760
cacgctgccg cgccggtagt acgtaagagg ttccaacttt caccataatg aaataagatc   2820
actaccgggc gtattttttg agttatcgag attttcagga gctaaggaag ctaaaatgag   2880
ccatattcaa cgggaaacgt cttgctcgag gccgcgatta aattccaaca tggatgctga   2940
tttatatggg tataaatggg ctcgcgataa tgtcgggcaa tcaggtgcga caatctatcg   3000
attgtatggg aagcccgatg cgccagagtt gtttctgaaa catggcaaag gtagcgttgc   3060
caatgatgtt acagatgaga tggtcaggct aaactggctg acggaattta tgcctcttcc   3120
gaccatcaag cattttatcc gtactcctga tgatgcatgg ttactcacca ctgcgatccc   3180
agggaaaaca gcattccagg tattagaaga atatcctgat tcaggtgaaa atattgttga   3240
tgcgctggca gtgttcctgc gccggttgca ttcgattcct gtttgtaatt gtccttttaa   3300
cggcgatcgc gtatttcgtc tcgctcaggc gcaatcacga atgaataacg gtttggttgg   3360
tgcgagtgat tttgatgacg agcgtaatgg ctggcctgtt gaacaagtct ggaaagaaat   3420
gcataagctt ttgccattct caccggattc agtcgtcact catggtgatt tctcacttga   3480
taaccttatt tttgacgagg ggaaattaat aggttgtatt gatgttggac gagtcggaat   3540
cgcagaccga taccaggatc ttgccatcct atggaactgc ctcggtgagt tttctccttc   3600
attacagaaa cggctttttc aaaaatatgg tattgataat cctgatatga ataaattgca   3660
gtttcacttg atgctcgatg agtttttctg agggcggatc cccctcaagt caaaagcctc   3720
cggtcggagg cttttgactt tctgctatgg aggtcaggta tgatttttat gacaacttga   3780
```

cggctacatc attcactttt tcttcacaac cggcacggaa ctcgctcggg ctggccccgg 3840
tgcatttttt aaatacccgc gagaaataga gttgatcgtc aaaaccaaca ttgcgaccga 3900
cggtggcgat aggcatccgg gtggtgctca aaagcagctt cgcctggctg atacgttggt 3960
cctcgcgcca gcttaagacg ctaatcccta actgctggcg gaaaagatgt gacagacgcg 4020
acggcgacaa gcaaacatgc tgtgcgacgc tggcgatatc aaaattgctg tctgccaggt 4080
gatcgctgat gtactgacaa gcctcgcgta cccgattatc catcggtgga tggagcgact 4140
cgttaatcgc ttccatgcgc cgcagtaaca attgctcaag cagatttatc gccagcagct 4200
ccgaatagcg cccttcccct tgcccggcgt taatgatttg cccaaacagg tcgctgaaat 4260
gcggctggtg cgcttcatcc gggcgaaaga accccgtatt ggcaaatatt gacggccagt 4320
taagccattc atgccagtag gcgcgcggac gaaagtaaac ccactggtga taccattcgc 4380
gagcctccgg atgacgaccg tagtgatgaa tctctcctgg cgggaacagc aaaatatcac 4440
ccggtcggca aacaaattct cgtccctgat ttttcaccac cccctgaccg cgaatggtga 4500
gattgagaat ataacctttc attcccagcg gtcggtcgat aaaaaaatcg agataaccgt 4560
tggcctcaat cggcgttaaa cccgccacca gatgggcatt aaacgagtat cccggcagca 4620
ggggatcatt ttgcgcttca gccatacttt tcatactccc gccattcaga gaagaaacca 4680
attgtccata ttgcatcaga cattgccgtc actgcgtctt ttactggctc ttctcgctaa 4740
ccaaaccggt aaccccgctt attaaaagca ttctgtaaca aagcgggacc aaagccatga 4800
caaaaacgcg taacaaaagt gtctataatc acggcagaaa agtccacatt gattatttgc 4860
acggcgtcac actttgctat gccatagcat ttttatccat aagattagcg gatcctacct 4920
gacgcttttt atcgcaactc tctactgttt ctccataccc gtttttttgg gctagagaat 4980
tcgtc 4985

<210> SEQ ID NO 15
<211> LENGTH: 4831
<212> TYPE: DNA
<213> ORGANISM: Escherichia coli

<400> SEQUENCE: 15
aacgaattca agcttgatat cattcaggac gagcctcaga ctccagcgta actggactga 60
aaacaaacta aagcgccctt gtggcgcttt agttttgttc cgctcatgat aataatggtt 120
tcttagacgt caggtggcac ttttcgggga aatgtgcgcg cccgcgttcc tgctggcgct 180
gggcctgttt ctggcgctgg acttcccgct gttccgtcag cagcttttcg cccacggcct 240
tgatgatcgc ggcggccttg gcctgcatat cccgattcaa cggccccagg gcgtccagaa 300
cgggcttcag gcgctcccga aggtctcggg ccgtctcttg ggcttgatcg gccttcttgc 360
gcatctcacg cgctcctgcg gcggcctgta gggcaggctc atacccctgc cgaaccgctt 420
ttgtcagccg gtcggccacg gcttccggcg tctcaacgcg ctttgagatt cccagctttt 480
cggccaatcc ctgcggtgca taggcgcgtg gctcgaccgc ttgcgggctg atggtgacgt 540
ggcccactgg tggccgctcc agggcctcgt agaacgcctg aatgcgcgtg tgacgtgcct 600
tgctgccctc gatgccccgt tgcagcccta gatcggccac agcggccgca aacgtggtct 660
ggtcgcgggt catctgcgct ttgttgccga tgaactcctt ggccgacagc ctgccgtcct 720
gcgtcagcgg caccacgaac gcggtcatgt gcgggctggt ttcgtcacgg tggatgctgg 780
ccgtcacgat gcgatccgcc ccgtacttgt ccgccagcca cttgtgcgcc ttctcgaaga 840

-continued

```
acgccgcctg ctgttcttgg ctggccgact tccaccattc cgggctggcc gtcatgacgt    900
actcgaccgc caacacagcg tccttgcgcc gcttctctgg cagcaactcg cgcagtcggc    960
ccatcgcttc atcggtgctg ctggccgccc agtgctcgtt ctctggcgtc ctgctggcgt   1020
cagcgttggg cgtctcgcgc tcgcggtagg cgtgcttgag actggccgcc acgttgccca   1080
ttttcgccag cttcttgcat cgcatgatcg cgtatgccgc catgcctgcc cctccctttt   1140
ggtgtccaac cggctcgacg ggggcagcgc aaggcggtgc ctccggcggg ccactcaatg   1200
cttgagtata ctcactagac tttgcttcgc aaagtcgtga ccgcctacgg cggctgcggc   1260
gccctacggg cttgctctcc gggcttcgcc ctgcgcggtc gctgcgctcc cttgccagcc   1320
cgtggatatg tggacgatgg ccgcgagcgg ccaccggctg gctcgcttcg ctcggcccgt   1380
ggacaaccct gctggacaag ctgatggaca ggctgcgcct gcccacgagc ttgaccacag   1440
ggattgccca ccggctaccc agccttcgac cacataccca ccggctccaa ctgcgcggcc   1500
tgcggccttg ccccatcaat ttttttaatt ttctctgggg aaaagcctcc ggcctgcggc   1560
ctgcgcgctt cgcttgccgg ttggacacca agtggaaggc gggtcaaggc tcgcgcagcg   1620
accgcgcagc ggcttggcct tgacgcgcct ggaacgaccc aagcctatgc gagtgggggc   1680
agtcgaaggc gaagcccgcc cgcctgcccc ccgagcctca cggcggcgag tgcgggggtt   1740
ccaagggggc agcgccacct tgggcaaggc cgaaggccgc gcagtcgatc aacaagcccc   1800
ggaggggcca ctttttgccg gagggggagc cgcgccgaag gcgtggggga accccgcagg   1860
ggtgcccttc tttgggcacc aaagaactag atatagggcg aaatgcgaaa gacttaaaaa   1920
tcaacaactt aaaaaagggg ggtacgcaac agctcattgc ggcacccccc gcaatagctc   1980
attgcgtagg ttaaagaaaa tctgtaattg actgccactt ttacgcaacg cataattgtt   2040
gtcgcgctgc cgaaaagttg cagctgattg cgcatggtgc cgcaaccgtg cggcacccta   2100
ccgcatggag ataagcatgg ccacgcagtc cagagaaatc ggcattcaag ccaagaacaa   2160
gcccggtcac tgggtgcaaa cggaacgcaa agcgcatgag gcgtgggccg ggcttattgc   2220
gaggaaaccc acggcggcaa tgctgctgca tcacctcgtg gcgcagatgg gccaccagaa   2280
cgccgtggtg gtcagccaga agacactttc caagctcatc ggacgttctt tgcggacggt   2340
ccaatacgca gtcaaggact tggtggccga gcgctggatc tccgtcgtga agctcaacgg   2400
ccccggcacc gtgtcggcct acgtggtcaa tgaccgcgtg gcgtggggcc agccccgcga   2460
ccagttgcgc ctgtcggtgt tcagtgccgc cgtggtggtt gatcacgacg accaggacga   2520
atcgctgttg gggcatggcg acctgcgccg catcccgacc ctgtatccgg gcgagcagca   2580
actaccgacc ggccccggcg aggagccgcc cagccagccc ggcattccgg gcatggaacc   2640
agacctgcca gccttgaccg aaacggagga atgggaacgg cgcgggcagc agcgcctgcc   2700
gatgcccgat gagccgtgtt ttctggacga tggcgagccg ttggagccgc cgacacgggt   2760
cacgctgccg cgccggtagt acgtaagagg ttccaacttt caccataatg aaataagatc   2820
actaccgggc gtattttttg agttatcgag attttcagga gctaaggaag ctaaaatgga   2880
gaaaaaaatc actggatata ccaccgttga tatatcccaa tggcatcgta aagaacattt   2940
tgaggcattt cagtcagttg ctcaatgtac ctataaccag accgttcagc tggatattac   3000
ggccttttta aagaccgtaa agaaaaataa gcacaagttt tatccggcct ttattcacat   3060
tcttgcccgc ctgatgaatg ctcatccgga attccgtatg gcaatgaaag acggtgagct   3120
ggtgatatgg gatagtgttc acccttgtta caccgttttc catgagcaaa ctgaaacgtt   3180
ttcatcgctc tggagtgaat accacgacga tttccggcag tttctacaca tatattcgca   3240
```

-continued

```
agatgtggcg tgttacggtg aaaacctggc ctatttccct aaagggttta ttgagaatat   3300

gtttttcgtc tcagccaatc cctgggtgag tttcaccagt tttgatttaa acgtggccaa   3360

tatggacaac ttcttcgccc ccgttttcac catgggcaaa tattatacgc aaggcgacaa   3420

ggtgctgatg ccgctggcga ttcaggttca tcatgccgtt tgtgatggct tccatgtcgg   3480

cagaatgctt aatgaattac aacagtactg cgatgagtgg cagggcgggg cgtaaacgcg   3540

tggatccccc tcaagtcaaa agcctccggt cggaggcttt tgactttctg ctatggaggt   3600

caggtatgat ttttatgaca acttgacggc tacatcattc actttttctt cacaaccggc   3660

acggaactcg ctcgggctgg ccccggtgca tttttttaaat acccgcgaga aatagagttg   3720

atcgtcaaaa ccaacattgc gaccgacggt ggcgataggc atccgggtgg tgctcaaaag   3780

cagcttcgcc tggctgatac gttggtcctc gcgccagctt aagacgctaa tccctaactg   3840

ctggcggaaa agatgtgaca gacgcgacgg cgacaagcaa acatgctgtg cgacgctggc   3900

gatatcaaaa ttgctgtctg ccaggtgatc gctgatgtac tgacaagcct cgcgtacccg   3960

attatccatc ggtggatgga gcgactcgtt aatcgcttcc atgcgccgca gtaacaattg   4020

ctcaagcaga tttatcgcca gcagctccga atagcgccct tccccttgcc cggcgttaat   4080

gatttgccca aacaggtcgc tgaaatgcgg ctggtgcgct tcatccgggc gaaagaaccc   4140

cgtattggca aatattgacg gccagttaag ccattcatgc cagtaggcgc gcggacgaaa   4200

gtaaacccac tggtgatacc attcgcgagc ctccggatga cgaccgtagt gatgaatctc   4260

tcctggcggg aacagcaaaa tatcacccgg tcggcaaaca aattctcgtc cctgattttt   4320

caccaccccc tgaccgcgaa tggtgagatt gagaatataa cctttcattc ccagcggtcg   4380

gtcgataaaa aaatcgagat aaccgttggc ctcaatcggc gttaaacccg ccaccagatg   4440

ggcattaaac gagtatcccg gcagcagggg atcattttgc gcttcagcca tacttttcat   4500

actcccgcca ttcagagaag aaaccaattg tccatattgc atcagacatt gccgtcactg   4560

cgtcttttac tggctcttct cgctaaccaa accggtaacc ccgcttatta aaagcattct   4620

gtaacaaagc gggaccaaag ccatgacaaa aacgcgtaac aaaagtgtct ataatcacgg   4680

cagaaaagtc cacattgatt atttgcacgg cgtcacactt tgctatgcca tagcattttt   4740

atccataaga ttagcggatc ctacctgacg ctttttatcg caactctcta ctgtttctcc   4800

atacccgttt ttttgggcta gagaattcgt c                                   4831
```

<210> SEQ ID NO 16
<211> LENGTH: 5363
<212> TYPE: DNA
<213> ORGANISM: Escherichia coli

<400> SEQUENCE: 16

```
aacgaattca agcttgatat cattcaggac gagcctcaga ctccagcgta actggactga     60

aaacaaacta aagcgccctt gtggcgcttt agttttgttc cgctcatgat aataatggtt    120

tcttagacgt caggtggcac ttttcgggga aatgtgcgcg cccgcgttcc tgctggcgct    180

gggcctgttt ctggcgctgg acttcccgct gttccgtcag cagcttttcg cccacggcct    240

tgatgatcgc ggcggccttg gcctgcatat cccgattcaa cggccccagg gcgtccagaa    300

cgggcttcag gcgctcccga aggtctcggg ccgtctcttg ggcttgatcg gccttcttgc    360

gcatctcacg cgctcctgcg gcggcctgta gggcaggctc atacccctgc cgaaccgctt    420

ttgtcagccg gtcggccacg gcttccggcg tctcaacgcg ctttgagatt cccagctttt    480
```

-continued

```
cggccaatcc ctgcggtgca taggcgcgtg gctcgaccgc ttgcgggctg atggtgacgt    540
ggcccactgg tggccgctcc agggcctcgt agaacgcctg aatgcgcgtg tgacgtgcct    600
tgctgccctc gatgccccgt tgcagcccta gatcggccac agcggccgca aacgtggtct    660
ggtcgcgggt catctgcgct ttgttgccga tgaactcctt ggccgacagc ctgccgtcct    720
gcgtcagcgg caccacgaac gcggtcatgt gcgggctggt ttcgtcacgg tggatgctgg    780
ccgtcacgat gcgatccgcc ccgtacttgt ccgccagcca cttgtgcgcc ttctcgaaga    840
acgccgcctg ctgttcttgg ctggccgact tccaccattc cgggctggcc gtcatgacgt    900
actcgaccgc caacacagcg tccttgcgcc gcttctctgg cagcaactcg cgcagtcggc    960
ccatcgcttc atcggtgctg ctggccgccc agtgctcgtt ctctggcgtc ctgctggcgt   1020
cagcgttggg cgtctcgcgc tcgcggtagg cgtgcttgag actggccgcc acgttgccca   1080
ttttcgccag cttcttgcat cgcatgatcg cgtatgccgc catgcctgcc cctccctttt   1140
ggtgtccaac cggctcgacg gggcagcgc aaggcggtgc ctccggcggg ccactcaatg    1200
cttgagtata ctcactagac tttgcttcgc aaagtcgtga ccgcctacgg cggctgcggc   1260
gccctacggg cttgctctcc gggcttcgcc ctgcgcggtc gctgcgctcc cttgccagcc   1320
cgtggatatg tggacgatgg ccgcgagcgg ccaccggctg gctcgcttcg ctcggcccgt   1380
ggacaaccct gctggacaag ctgatggaca ggctgcgcct gcccacgagc ttgaccacag   1440
ggattgccca ccggctaccc agccttcgac cacataccca ccggctccaa ctgcgcggcc   1500
tgcggccttg ccccatcaat ttttttaatt ttctctgggg aaaagcctcc ggcctgcggc   1560
ctgcgcgctt cgcttgccgg ttggacacca agtggaaggc gggtcaaggc tcgcgcagcg   1620
accgcgcagc ggcttggcct tgacgcgcct ggaacgaccc aagcctatgc gagtgggggc   1680
agtcgaaggc gaagcccgcc cgcctgcccc ccgagcctca cggcggcgag tgcgggggtt   1740
ccaagggggc agcgccacct tgggcaaggc cgaaggccgc gcagtcgatc aacaagcccc   1800
ggaggggcca ctttttgccg gagggggagc cgcgccgaag gcgtggggga accccgcagg   1860
ggtgcccttc tttgggcacc aaagaactag atatagggcg aaatgcgaaa gacttaaaaa   1920
tcaacaactt aaaaaagggg ggtacgcaac agctcattgc ggcacccccc gcaatagctc   1980
attgcgtagg ttaaagaaaa tctgtaattg actgccactt ttacgcaacg cataattgtt   2040
gtcgcgctgc cgaaaagttg cagctgattg cgcatggtgc cgcaaccgtg cggcacccta   2100
ccgcatggag ataagcatgg ccacgcagtc cagagaaatc ggcattcaag ccaagaacaa   2160
gcccggtcac tgggtgcaaa cggaacgcaa agcgcatgag gcgtgggccg ggcttattgc   2220
gaggaaaccc acggcggcaa tgctgctgca tcacctcgtg gcgcagatgg gccaccagaa   2280
cgccgtggtg gtcagccaga agacactttc caagctcatc ggacgttctt tgcggacggt   2340
ccaatacgca gtcaaggact tggtggccga gcgctggatc tccgtcgtga agctcaacgg   2400
ccccggcacc gtgtcggcct acgtggtcaa tgaccgcgtg gcgtggggcc agccccgcga   2460
ccagttgcgc ctgtcggtgt tcagtgccgc cgtggtggtt gatcacgacg accaggacga   2520
atcgctgttg ggcatggcg acctgcgccg catcccgacc ctgtatccgg gcgagcagca    2580
actaccgacc ggccccggcg aggagccgcc cagccagccc ggcattccgg gcatggaacc   2640
agacctgcca gccttgaccg aaacggagga atgggaacgg cgcgggcagc agcgcctgcc   2700
gatgcccgat gagccgtgtt ttctggacga tggcgagccg ttggagccgc cgacacgggt   2760
cacgctgccg cgccggtagt acgtaagagg ttccaacttt caccataatg aaataagatc   2820
actaccgggc gtattttttg agttatcgag attttcagga gctaaggaag ctaaaatgaa   2880
```

```
atctaacaat gcgctcatcg tcatcctcgg caccgtcacc ctggatgctg taggcatagg   2940
cttggttatg ccggtactgc cgggcctctt gcgggatatc gtccattccg acagcatcgc   3000
cagtcactat ggcgtgctgc tagcgctata tgcgttgatg caatttctat gcgcacccgt   3060
tctcggagca ctgtccgacc gctttggccg ccgcccagtc ctgctcgctt cgctacttgg   3120
agccactatc gactacgcga tcatggcgac cacacccgtc ctgtggatcc tctacgccgg   3180
acgcatcgtg gccggcatca ccggcgccac aggtgcggtt gctggcgcct atatcgccga   3240
catcaccgat ggggaagatc gggctcgcca cttcgggctc atgagcgctt gtttcggcgt   3300
gggtatggtg gcaggccccg tggccggggg actgttgggc gccatctcct tgcatgcacc   3360
attccttgcg gcggcggtgc tcaacggcct caacctacta ctgggctgct tcctaatgca   3420
ggagtcgcat aagggagagc gtcgaccgat gcccttgaga gccttcaacc cagtcagctc   3480
cttccggtgg gcgcggggca tgactatcgt cgccgcactt atgactgtct tctttatcat   3540
gcaactcgta ggacaggtgc cggcagcgct ctgggtcatt ttcggcgagg accgctttcg   3600
ctggagcgcg acgatgatcg gcctgtcgct tgcggtattc ggaatcttgc acgccctcgc   3660
tcaagccttc gtcactggtc ccgccaccaa acgtttcggc gagaagcagg ccattatcgc   3720
cggcatggcg gccgacgcgc tgggctacgt cttgctggcg ttcgcgacgc gaggctggat   3780
ggccttcccc attatgattc ttctcgcttc cggcggcatc gggatgcccg cgttgcaggc   3840
catgctgtcc aggcaggtag atgacgacca tcagggacag cttcaaggat cgctcgcggc   3900
tcttaccagc ctaacttcga tcactggacc gctgatcgtc acggcgattt atgccgcctc   3960
ggcgagcaca tggaacgggt tggcatggat tgtaggcgcc gccctatacc ttgtctgcct   4020
ccccgcgttg cgtcgcggtg catggagccg ggccacctcg acctgaatgg aagggatccc   4080
cctcaagtca aaagcctccg gtcggaggct tttgactttc tgctatggag gtcaggtatg   4140
atttttatga caacttgacg gctacatcat tcactttttc ttcacaaccg gcacggaact   4200
cgctcgggct ggccccggtg catttttttaa atacccgcga gaaatagagt tgatcgtcaa   4260
aaccaacatt gcgaccgacg gtggcgatag gcatccgggt ggtgctcaaa agcagcttcg   4320
cctggctgat acgttggtcc tcgcgccagc ttaagacgct aatccctaac tgctggcgga   4380
aaagatgtga cagacgcgac ggcgacaagc aaacatgctg tgcgacgctg gcgatatcaa   4440
aattgctgtc tgccaggtga tcgctgatgt actgacaagc ctcgcgtacc cgattatcca   4500
tcggtggatg gagcgactcg ttaatcgctt ccatgcgccg cagtaacaat tgctcaagca   4560
gatttatcgc cagcagctcc gaatagcgcc cttccccttg cccggcgtta atgatttgcc   4620
caaacaggtc gctgaaatgc ggctggtgcg cttcatccgg gcgaaagaac cccgtattgg   4680
caaatattga cggccagtta agccattcat gccagtaggc gcgcggacga aagtaaaccc   4740
actggtgata ccattcgcga gcctccggat gacgaccgta gtgatgaatc tctcctggcg   4800
ggaacagcaa aatatcaccc ggtcggcaaa caaattctcg tccctgattt ttcaccaccc   4860
cctgaccgcg aatggtgaga ttgagaatat aacctttcat tcccagcggt cggtcgataa   4920
aaaaatcgag ataaccgttg gcctcaatcg gcgttaaacc cgccaccaga tgggcattaa   4980
acgagtatcc cggcagcagg ggatcatttt gcgcttcagc catacttttc atactcccgc   5040
cattcagaga agaaaccaat tgtccatatt gcatcagaca ttgccgtcac tgcgtctttt   5100
actggctctt ctcgctaacc aaaccggtaa ccccgcttat taaaagcatt ctgtaacaaa   5160
gcgggaccaa agccatgaca aaaacgcgta acaaaagtgt ctataatcac ggcagaaaag   5220
```

```
tccacattga ttatttgcac ggcgtcacac tttgctatgc catagcattt ttatccataa   5280

gattagcgga tcctacctga cgctttttat cgcaactctc tactgtttct ccatacccgt   5340

tttttgggc tagagaattc gtc                                             5363
```

<210> SEQ ID NO 17
<211> LENGTH: 4406
<212> TYPE: DNA
<213> ORGANISM: Escherichia coli

<400> SEQUENCE: 17

```
aacgaattca agcttgatat cattcaggac gagcctcaga ctccagcgta actggactga     60

aaacaaacta aagcgccctt gtggcgcttt agttttgttc cgctcatgat aataatggtt    120

tcttagacgt caggtggcac ttttcgggga aatgtgcgcg cccgcgttcc tgctggcgct    180

gggcctgttt ctggcgctgg acttcccgct gttccgtcag cagcttttcg cccacggcct    240

tgatgatcgc ggcggccttg gcctgcatat cccgattcaa cggccccagg gcgtccagaa    300

cgggcttcag gcgctcccga aggtctcggg ccgtctcttg ggcttgatcg gccttcttgc    360

gcatctcacg cgctcctgcg gcggcctgta gggcaggctc atacccctgc cgaaccgctt    420

ttgtcagccg gtcggccacg gcttccggcg tctcaacgcg ctttgagatt cccagctttt    480

cggccaatcc ctgcggtgca taggcgcgtg gctcgaccgc ttgcgggctg atggtgacgt    540

ggcccactgg tggccgctcc agggcctcgt agaacgcctg aatgcgcgtg tgacgtgcct    600

tgctgccctc gatgccccgt tgcagcccta gatcggccac agcggccgca aacgtggtct    660

ggtcgcgggt catctgcgct ttgttgccga tgaactcctt ggccgacagc ctgccgtcct    720

gcgtcagcgg caccacgaac gcggtcatgt gcgggctggt ttcgtcacgg tggatgctgg    780

ccgtcacgat gcgatccgcc ccgtacttgt ccgccagcca cttgtgcgcc ttctcgaaga    840

acgccgcctg ctgttcttgg ctggccgact tccaccattc cgggctggcc gtcatgacgt    900

actcgaccgc caacacagcg tccttgcgcc gcttctctgg cagcaactcg cgcagtcggc    960

ccatcgcttc atcggtgctg ctggccgccc agtgctcgtt ctctggcgtc ctgctggcgt   1020

cagcgttggg cgtctcgcgc tcgcggtagg cgtgcttgag actggccgcc acgttgccca   1080

ttttcgccag cttcttgcat cgcatgatcg cgtatgccgc catgcctgcc cctccctttt   1140

ggtgtccaac cggctcgacg gggcagcgc aaggcggtgc ctccggcggg ccactcaatg   1200

cttgagtata ctcactagac tttgcttcgc aaagtcgtga ccgcctacgg cggctgcggc   1260

gccctacggg cttgctctcc gggcttcgcc ctgcgcggtc gctgcgctcc cttgccagcc   1320

cgtggatatg tggacgatgg ccgcgagcgg ccaccggctg gctcgcttcg ctcggcccgt   1380

ggacaaccct gctggacaag ctgatggaca ggctgcgcct gcccacgagc ttgaccacag   1440

ggattgccca ccggctaccc agccttcgac cacataccca ccggctccaa ctgcgcggcc   1500

tgcggccttg ccccatcaat ttttttaatt ttctctgggg aaaagcctcc ggcctgcggc   1560

ctgcgcgctt cgcttgccgg ttggacacca agtggaaggc gggtcaaggc tcgcgcagcg   1620

accgcgcagc ggcttggcct tgacgcgcct ggaacgaccc aagcctatgc gagtgggggc   1680

agtcgaaggc gaagcccgcc cgcctgcccc ccgagcctca cggcggcgag tgcgggggtt   1740

ccaagggggc agcgccacct tgggcaaggc cgaaggccgc gcagtcgatc aacaagcccc   1800

ggaggggcca ctttttgccg gagggggagc cgcgccgaag gcgtgggggga accccgcagg   1860

ggtgcccttc tttgggcacc aaagaactag atatagggcg aaatgcgaaa gacttaaaaa   1920

tcaacaactt aaaaaagggg ggtacgcaac agctcattgc ggcaccccccc gcaatagctc   1980
```

-continued

```
attgcgtagg ttaaagaaaa tctgtaattg actgccactt ttacgcaacg cataattgtt   2040
gtcgcgctgc cgaaaagttg cagctgattg cgcatggtgc cgcaaccgtg cggcacccta   2100
ccgcatggag ataagcatgg ccacgcagtc cagagaaatc ggcattcaag ccaagaacaa   2160
gcccggtcac tgggtgcaaa cggaacgcaa agcgcatgag gcgtgggccg ggcttattgc   2220
gaggaaaccc acggcggcaa tgctgctgca tcacctcgtg gcgcagatgg gccaccagaa   2280
cgccgtggtg gtcagccaga agacactttc caagctcatc ggacgttctt tgcggacggt   2340
ccaatacgca gtcaaggact tggtggccga gcgctggatc tccgtcgtga agctcaacgg   2400
ccccggcacc gtgtcggcct acgtggtcaa tgaccgcgtg gcgtggggcc agccccgcga   2460
ccagttgcgc ctgtcggtgt tcagtgccgc cgtggtggtt gatcacgacg accaggacga   2520
atcgctgttg gggcatggcg acctgcgccg catcccgacc ctgtatccgg gcgagcagca   2580
actaccgacc ggccccggcg aggagccgcc cagccagccc ggcattccgg gcatggaacc   2640
agacctgcca gccttgaccg aaacggagga atgggaacgg cgcgggcagc agcgcctgcc   2700
gatgcccgat gagccgtgtt ttctggacga tggcgagccg ttggagccgc cgacacgggt   2760
cacgctgccg cgccggtagt acgtaagagg ttccaacttt caccataatg aaataagatc   2820
actaccgggc gtattttttg agttatcgag attttcagga gctaaggaag ctaaaatggg   2880
tcaaagtagc gatgaagcca acgctcccgt tgcagggcag tttgcgcttc ccctgagtgc   2940
cacctttggc ttaggggatc gcgtacgcaa gaaatctggt gccgcttggc agggtcaagt   3000
cgtcggttgg tattgcacaa aactcactcc tgaaggctat gcggtcgagt ccgaatccca   3060
cccaggctca gtgcaaattt atcctgtggc tgcacttgaa cgtgtggcct aagaatggat   3120
ccccctcaag tcaaaagcct ccggtcggag gcttttgact ttctgctatg gaggtcaggt   3180
atgattttta tgacaacttg acggctacat cattcacttt ttcttcacaa ccggcacgga   3240
actcgctcgg gctggccccg gtgcattttt taaatacccg cgagaaatag agttgatcgt   3300
caaaaccaac attgcgaccg acggtggcga taggcatccg ggtggtgctc aaaagcagct   3360
tcgcctggct gatacgttgg tcctcgcgcc agcttaagac gctaatccct aactgctggc   3420
ggaaaagatg tgacagacgc gacggcgaca agcaaacatg ctgtgcgacg ctggcgatat   3480
caaaattgct gtctgccagg tgatcgctga tgtactgaca agcctcgcgt acccgattat   3540
ccatcggtgg atggagcgac tcgttaatcg cttccatgcg ccgcagtaac aattgctcaa   3600
gcagatttat cgccagcagc tccgaatagc gcccttcccc ttgcccggcg ttaatgattt   3660
gcccaaacag gtcgctgaaa tgcggctggt gcgcttcatc cgggcgaaag aaccccgtat   3720
tggcaaatat tgacggccag ttaagccatt catgccagta ggcgcgcgga cgaaagtaaa   3780
cccactggtg ataccattcg cgagcctccg gatgacgacc gtagtgatga atctctcctg   3840
gcgggaacag caaaatatca cccggtcggc aaacaaattc tcgtccctga tttttcacca   3900
ccccctgacc gcgaatggtg agattgagaa tataaccttt cattcccagc ggtcggtcga   3960
taaaaaaatc gagataaccg ttggcctcaa tcggcgttaa acccgccacc agatgggcat   4020
taaacgagta tcccggcagc aggggatcat tttgcgcttc agccatactt ttcatactcc   4080
cgccattcag agaagaaacc aattgtccat attgcatcag acattgccgt cactgcgtct   4140
tttactggct cttctcgcta accaaaccgg taaccccgct tattaaaagc attctgtaac   4200
aaagcgggac caaagccatg acaaaaacgc gtaacaaaag tgtctataat cacggcagaa   4260
aagtccacat tgattatttg cacggcgtca cactttgcta tgccatagca tttttatcca   4320
```

-continued taagattagc ggatcctacc tgacgctttt tatcgcaact ctctactgtt tctccatacc 4380
cgtttttttg ggctagagaa ttcgtc 4406

<210> SEQ ID NO 18
<211> LENGTH: 7044
<212> TYPE: DNA
<213> ORGANISM: Escherichia coli

<400> SEQUENCE: 18
aacgaattca agcttgatat cattcaggac gagcctcaga ctccagcgta actggactga 60
aaacaaacta aagcgccctt gtggcgcttt agttttgttc cgctcatgat aataatggtt 120
tcttagacgt caggtggcac ttttcgggga aatgtgcgcg cccgcgttcc tgctggcgct 180
gggcctgttt ctggcgctgg acttcccgct gttccgtcag cagcttttcg cccacggcct 240
tgatgatcgc ggcggccttg gcctgcatat cccgattcaa cggccccagg gcgtccagaa 300
cgggcttcag gcgctcccga aggtctcggg ccgtctcttg ggcttgatcg gccttcttgc 360
gcatctcacg cgctcctgcg gcggcctgta gggcaggctc atacccctgc cgaaccgctt 420
ttgtcagccg gtcggccacg gcttccggcg tctcaacgcg ctttgagatt cccagctttt 480
cggccaatcc ctgcggtgca taggcgcgtg gctcgaccgc ttgcgggctg atggtgacgt 540
ggcccactgg tggccgctcc agggcctcgt agaacgcctg aatgcgcgtg tgacgtgcct 600
tgctgccctc gatgccccgt tgcagcccta gatcggccac agcggccgca aacgtggtct 660
ggtcgcgggt catctgcgct ttgttgccga tgaactcctt ggccgacagc ctgccgtcct 720
gcgtcagcgg caccacgaac gcggtcatgt gcgggctggt ttcgtcacgg tggatgctgg 780
ccgtcacgat gcgatccgcc ccgtacttgt ccgccagcca cttgtgcgcc ttctcgaaga 840
acgccgcctg ctgttcttgg ctggccgact tccaccattc cgggctggcc gtcatgacgt 900
actcgaccgc caacacagcg tccttgcgcc gcttctctgg cagcaactcg cgcagtcggc 960
ccatcgcttc atcggtgctg ctggccgccc agtgctcgtt ctctggcgtc ctgctggcgt 1020
cagcgttggg cgtctcgcgc tcgcggtagg cgtgcttgag actggccgcc acgttgccca 1080
ttttcgccag cttcttgcat cgcatgatcg cgtatgccgc catgcctgcc cctccctttt 1140
ggtgtccaac cggctcgacg gggcagcgc aaggcggtgc ctccggcggg ccactcaatg 1200
cttgagtata ctcactagac tttgcttcgc aaagtcgtga ccgcctacgg cggctgcggc 1260
gccctacggg cttgctctcc gggcttcgcc ctgcgcggtc gctgcgctcc cttgccagcc 1320
cgtggatatg tggacgatgg ccgcgagcgg ccaccggctg gctcgcttcg ctcggcccgt 1380
ggacaaccct gctggacaag ctgatggaca ggctgcgcct gcccacgagc ttgaccacag 1440
ggattgccca ccggctaccc agccttcgac cacataccca ccggctccaa ctgcgcggcc 1500
tgcggccttg ccccatcaat ttttttaatt ttctctgggg aaaagcctcc ggcctgcggc 1560
ctgcgcgctt cgcttgccgg ttggacacca agtggaaggc gggtcaaggc tcgcgcagcg 1620
accgcgcagc ggcttggcct tgacgcgcct ggaacgaccc aagcctatgc gagtgggggc 1680
agtcgaaggc gaagcccgcc cgcctgcccc ccgagcctca cggcggcgag tgcgggggtt 1740
ccaagggggc agcgccacct tgggcaaggc cgaaggccgc gcagtcgatc aacaagcccc 1800
ggaggggcca ctttttgccg gagggggagc cgcgccgaag gcgtggggga accccgcagg 1860
ggtgcccttc tttgggcacc aaagaactag atatagggcg aaatgcgaaa gacttaaaaa 1920
tcaacaactt aaaaaagggg ggtacgcaac agctcattgc ggcacccccc gcaatagctc 1980
attgcgtagg ttaaagaaaa tctgtaattg actgccactt ttacgcaacg cataattgtt 2040

-continued

```
gtcgcgctgc cgaaaagttg cagctgattg cgcatggtgc cgcaaccgtg cggcacccta   2100
ccgcatggag ataagcatgg ccacgcagtc cagagaaatc ggcattcaag ccaagaacaa   2160
gcccggtcac tgggtgcaaa cggaacgcaa agcgcatgag gcgtgggccg ggcttattgc   2220
gaggaaaccc acggcggcaa tgctgctgca tcacctcgtg gcgcagatgg gccaccagaa   2280
cgccgtggtg gtcagccaga agacactttc caagctcatc ggacgttctt tgcggacggt   2340
ccaatacgca gtcaaggact tggtggccga gcgctggatc tccgtcgtga agctcaacgg   2400
ccccggcacc gtgtcggcct acgtggtcaa tgaccgcgtg gcgtggggcc agccccgcga   2460
ccagttgcgc ctgtcggtgt tcagtgccgc cgtggtggtt gatcacgacg accaggacga   2520
atcgctgttg gggcatggcg acctgcgccg catcccgacc ctgtatccgg gcgagcagca   2580
actaccgacc ggccccggcg aggagccgcc cagccagccc ggcattccgg gcatggaacc   2640
agacctgcca gccttgaccg aaacggagga atgggaacgg cgcgggcagc agcgcctgcc   2700
gatgcccgat gagccgtgtt ttctggacga tggcgagccg ttggagccgc cgacacgggt   2760
cacgctgccg cgccggtagt acgtaagagg ttccaacttt caccataatg aaataagatc   2820
actaccgggc gtatttttg agttatcgag attttcagga gctaaggaag ctaaaatgga   2880
agaacaaagc gtgaacatgg cgcgattgaa gggggaggtt ttgcccgccc tcttcgcgtc   2940
gccggcgacg attggcgagt acggggccgg catcgacggg gcggattccc tcaacgagct   3000
gtcgaatctg atggagcacg gcgcagttgc cgcgctggcc gacaaaatca gccagatcgt   3060
ggcgaagctg gccgacgcgg accccgcaa gatcgcggaa aagcctacct ggttcgagaa   3120
gatgcttggc cgtgaggttg aacgccaggt gaggtatcag gtcgcccgca agacgctcga   3180
ccagttgctg gacgaagccg agggcgtagc gcagcgcgtg cgggacacgt tgcgcgcctt   3240
ggatgacatg ctcaatacgc atgaggccga ggtagaccgg ctcagagcct acattcaagc   3300
cgggcgcgag ttcctggacg agaaccccga ggccggcgcg gccaaggccg gcgtgatcga   3360
gttcgacaag ccgcgcgaac gcttcgcgcg caagctcgcc aacctggcaa ccctcatggc   3420
gtcccatgaa atgagcgtca ctcagatgaa gctcacgcgg gcgcaggccg tggacatgct   3480
ggaccgcttc tctgaaacgg catccgtcct ggtgcccgtc tggcgtcagc acaccctcgc   3540
gctcatcacc accaagaaca tgaatccggc aatggtcgcc gaggcggcca aagctcacca   3600
ggcgctcatg cggagccttt cgcagagcct ggaaggcatc aaccaataac acggcgggag   3660
aaccctatga acgcactgaa aacgacgcac gacgccaagg cccctatcgt cgccttcgac   3720
atgaccccgg caaccctgcg cgagctgggc ttgcaggaaa gcgacgtgcc ggaagtccat   3780
gcggtcgcgc agcggatcga ggtcggcagt ccgcagaccg ttgccgagtt cggccgcgac   3840
gtggccgagc acacgtcccg ctacgccgat agcctgctgg accaggtgcg caacagcgac   3900
ctggacgaag caggcgagaa actgacccag gttgtcgcca aggcccgttc cctgaacgtc   3960
ggccctttgt ccgacaaccg ttcccgcctg cccctgattg gcccgctgat cgaccgcttc   4020
cgcgtccgtt cgacgggctt catggcgcgc ttcgacacga cccgcgagca gatcgaacac   4080
ctggtcagcg aagtgcagac cacccagcaa ggcatcgcgc agcgcaatgc ctcgctcgac   4140
gaaatgttcg cagccgtgcg cgaggaacac cgccttcttg gcgtccacat cgcggccggc   4200
aaggtccgcc ttgccgagct gcgcgagcag gccgagggtc tgcgcggcaa tgtcgggaac   4260
gacccgggcc gcgtgcagga gctggccgac ctcgatgcga tggttgccaa cctggacaag   4320
cgcatcggcg acctgatcgc cttgcaacat tcggccatgc agagcctgcc gaccatccgc   4380
```

-continued

```
atgatccagg ccaacaacca gatgctggtc gataaattcc acaccatccg cgaaatcacc   4440
gtgccggcgt ggaagcggca attcatgctg gccttgagcc tcaacgagca gaagaacgcc   4500
gtcgaactgg ccacggccat cgacgacacc accaacgacc tgatgaagcg caatgcggcc   4560
ctgctgcatc gcacgtccgt cgagacggcg aaggagaacc aacgcctggt gatcgacgtg   4620
gacacgctca agcaggttca gacgacgctc atcaagaccg tcgaggacgt tattcgcatc   4680
cagcaggaag gcgtgcagaa gcgcaaggat gccgagaagc agatcgccgc aatgcgtggc   4740
gatcttcaag ccaagctgac ccgccagccc gtgcgcgagc tggcccaaca ggagtccgta   4800
tgaatgccac aaacaccgat gttttcgccc aggtaggcgg cctcgaggcc cgaggcgcga   4860
agatgaagaa gcggggcacc cgcttcctca tcgcggcgct ggcagtcctt gccattgccg   4920
ggatcggggc agtaacggga tgggcgatca gcccgagcgc gacgcccgga agcattgacg   4980
tgccgcaggt gctggcatcg acattcagcg accaggtgcc gggcagtgag ggcggcggcc   5040
tgggtggcgg cctgcccttc acttcggccg tcggggcatt cacggacttc atggcggggc   5100
cggcaatttt taccttgggc attcttggca tagtggtcgc gggtgccgtg ctcgtgttcg   5160
ggggtgaatt ctgcgggttc gtgcgatccg tctgcatgat ggtgatagcc gtcagcatga   5220
ttttcgtgtc gtcgaacttg gtgaagggca ttctcggcgg cgatcacgac gccggccctg   5280
cggagccttc gccgcgtgcg cgattcatgg cggccgtgga ggccaaggat ttcgcgcgag   5340
tgcaagagct gatcgaggcg cgtggagcca agtcggcggc tgattatgtc cttgcgcagc   5400
tcgccgtggc cgaaggtctg gaccgcaagc ctggtgcgcg cgtcgtggtc gggaaagcgg   5460
cgggcagcat ggcaatgccg cctgcggcgc tgggttttac gccaagggga gaagcggcat   5520
acgccatcga gcggtcagcc tatggtgagc cgaggtccag cattgcgaag cagtaccagc   5580
aggaatggaa ccggaaggcg gcgacctggt gggcgatggc cggtgtggcc ggcatcatcg   5640
gcgcgatcct ggcggcggcg gcaaccggct ttgttgggct ggcagtgtcg atccgcaacc   5700
gagtgaagcg cgtgcgcgac ctgttggtga tggagccggg tgcagagcca taagggatcc   5760
ccctcaagtc aaaagcctcc ggtcggaggc ttttgacttt ctgctatgga ggtcaggtat   5820
gatttttatg acaacttgac ggctacatca ttcacttttt cttcacaacc ggcacggaac   5880
tcgctcgggc tggccccggt gcattttta aatacccgcg agaaatagag ttgatcgtca   5940
aaaccaacat tgcgaccgac ggtggcgata ggcatccggg tggtgctcaa aagcagcttc   6000
gcctggctga tacgttggtc ctcgcgccag cttaagacgc taatccctaa ctgctggcgg   6060
aaaagatgtg acagacgcga cggcgacaag caaacatgct gtgcgacgct ggcgatatca   6120
aaattgctgt ctgccaggtg atcgctgatg tactgacaag cctcgcgtac ccgattatcc   6180
atcggtggat ggagcgactc gttaatcgct tccatgcgcc gcagtaacaa ttgctcaagc   6240
agatttatcg ccagcagctc cgaatagcgc ccttcccctt gcccggcgtt aatgatttgc   6300
ccaaacaggt cgctgaaatg cggctggtgc gcttcatccg ggcgaaagaa ccccgtattg   6360
gcaaatattg acggccagtt aagccattca tgccagtagg cgcgcggacg aaagtaaacc   6420
cactggtgat accattcgcg agcctccgga tgacgaccgt agtgatgaat ctctcctggc   6480
gggaacagca aaatatcacc cggtcggcaa acaaattctc gtccctgatt tttcaccacc   6540
ccctgaccgc gaatggtgag attgagaata taacctttca ttcccagcgg tcggtcgata   6600
aaaaaatcga gataaccgtt ggcctcaatc ggcgttaaac ccgccaccag atgggcatta   6660
aacgagtatc ccggcagcag gggatcattt tgcgcttcag ccatactttt catactcccg   6720
ccattcagag aagaaaccaa ttgtccatat tgcatcagac attgccgtca ctgcgtcttt   6780
```

-continued

```
tactggctct tctcgctaac caaaccggta accccgctta ttaaaagcat tctgtaacaa   6840

agcgggacca aagccatgac aaaaacgcgt aacaaaagtg tctataatca cggcagaaaa   6900

gtccacattg attatttgca cggcgtcaca ctttgctatg ccatagcatt tttatccata   6960

agattagcgg atcctacctg acgcttttta tcgcaactct ctactgtttc tccatacccg   7020

ttttttgggg ctagagaatt cgtc                                          7044
```

<210> SEQ ID NO 19
<211> LENGTH: 3784
<212> TYPE: DNA
<213> ORGANISM: Escherichia coli

<400> SEQUENCE: 19

```
aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180

cgagcttgac cacagggatt gcccaccggc tacccagcct tcgaccacat acccaccggc    240

tccaactgcg cggcctgcgg ccttgcccca tcaatttttt taatttttctc tggggaaaag    300

cctccggcct gcggcctgcg cgcttcgctt gccggttgga caccaagtgg aaggcgggtc    360

aaggctcgcg cagcgaccgc gcagcggctt ggccttgacg cgcctggaac gacccaagcc    420

tatgcgagtg ggggcagtcg aaggcgaagc ccgcccgcct gccccccgag cctcacggcg    480

gcgagtgcgg gggttccaag gggcagcgc caccttgggc aaggccgaag gccgcgcagt    540

cgatcaacaa gccccggagg ggccactttt tgccggaggg ggagccgcgc cgaaggcgtg    600

ggggaacccc gcaggggtgc ccttctttgg gcaccaaaga actagatata gggcgaaatg    660

cgaaagactt aaaaatcaac aacttaaaaa aggggggtac gcaacagctc attgcggcac    720

cccccgcaat agctcattgc gtaggttaaa gaaaatctgt aattgactgc cacttttacg    780

caacgcataa ttgttgtcgc gctgccgaaa agttgcagct gattgcgcat ggtgccgcaa    840

ccgtgcggca ccctaccgca tggagataag catggccacg cagtccagag aaatcggcat    900

tcaagccaag aacaagcccg gtcactgggt gcaaacggaa cgcaaagcgc atgaggcgtg    960

ggccgggctt attgcgagga aacccacggc ggcaatgctg ctgcatcacc tcgtggcgca   1020

gatgggccac cagaacgccg tggtggtcag ccagaagaca ctttccaagc tcatcggacg   1080

ttctttgcgg acggtccaat acgcagtcaa ggacttggtg gccgagcgct ggatctccgt   1140

cgtgaagctc aacggccccg gcaccgtgtc ggcctacgtg gtcaatgacc gcgtggcgtg   1200

gggccagccc cgcgaccagt tgcgcctgtc ggtgttcagt gccgccgtgg tggttgatca   1260

cgacgaccag gacgaatcgc tgttggggca tggcgacctg cgccgcatcc cgaccctgta   1320

tccgggcgag cagcaactac cgaccggccc cggcgaggag ccgcccagcc agcccggcat   1380

tccgggcatg gaaccagacc tgccagcctt gaccgaaacg gaggaatggg aacggcgcgg   1440

gcagcagcgc ctgccgatgc ccgatgagcc gtgttttctg gacgatggcg agccgttgga   1500

gccgccgaca cgggtcacgc tgccgcgccg gtagtacgta agaggttcca actttcacca   1560

taatgaaata agatcactac cgggcgtatt ttttgagtta tcgagatttt caggagctaa   1620

ggaagctaaa atgagtattc aacatttccg tgtcgccctt attccctttt ttgcggcatt   1680

ttgccttcct gtttttgctc acccagaaac gctggtgaaa gtaaaagatg ctgaagatca   1740

gttgggtgca cgagtgggtt acatcgaact ggatctcaac agcggtaaga tccttgagag   1800
```

-continued

```
tttacgcccc gaagaacgtt ttccaatgat gagcactttt aaagttctgc tatgtggcgc   1860

ggtattatcc cgtattgacg ccgggcaaga gcaactcggt cgccgcatac actattctca   1920

gaatgacttg gttgagtact caccagtcac agaaaagcat ctcacggatg gcatgacagt   1980

aagagaatta tgcagtgctg ccataaccat gagtgataac actgcggcca acttacttct   2040

ggcaacgatc ggaggaccga aggagctaac cgcttttttg cacaacatgg gggatcatgt   2100

aactcgcctt gatcgttggg aaccggagct gaatgaagcc ataccaaacg acgagcgtga   2160

caccacgatg cctgtagcaa tggcaacaac gttgcgcaaa ctattaactg gcgaactact   2220

tactctagct tcccggcaac aattaataga ctggatggag gcggataaag ttgcaggatc   2280

acttctgcgc tcggccctcc cggctggctg gtttattgct gataaatctg gagccggtga   2340

gcgtgggtct cgcggtatca ttgcagcact ggggccagat ggtaagccct cccgcatcgt   2400

agttatctac acgacgggga gtcaggcaac tatggatgaa cgaaatagac agatcgctga   2460

gataggtgcc tcactgatta agcattggta atgaggatcc ccctcaagtc aaaagcctcc   2520

ggtcggaggc ttttgacttt ctgctatgga ggtcaggtat gatttttatg acaacttgac   2580

ggctacatca ttcacttttt cttcacaacc ggcacggaac tcgctcgggc tggccccggt   2640

gcattttttta aatacccgcg agaaatagag ttgatcgtca aaaccaacat tgcgaccgac   2700

ggtggcgata ggcatccggg tggtgctcaa aagcagcttc gcctggctga tacgttggtc   2760

ctcgcgccag cttaagacgc taatccctaa ctgctggcgg aaaagatgtg acagacgcga   2820

cggcgacaag caaacatgct gtgcgacgct ggcgatatca aaattgctgt ctgccaggtg   2880

atcgctgatg tactgacaag cctcgcgtac ccgattatcc atcggtggat ggagcgactc   2940

gttaatcgct tccatgcgcc gcagtaacaa ttgctcaagc agatttatcg ccagcagctc   3000

cgaatagcgc ccttcccctt gcccggcgtt aatgatttgc ccaaacaggt cgctgaaatg   3060

cggctggtgc gcttcatccg ggcgaaagaa ccccgtattg gcaaatattg acggccagtt   3120

aagccattca tgccagtagg cgcgcggacg aaagtaaacc cactggtgat accattcgcg   3180

agcctccgga tgacgaccgt agtgatgaat ctctcctggc gggaacagca aaatatcacc   3240

cggtcggcaa acaaattctc gtccctgatt tttcaccacc ccctgaccgc gaatggtgag   3300

attgagaata taacctttca ttcccagcgg tcggtcgata aaaaaatcga gataaccgtt   3360

ggcctcaatc ggcgttaaac ccgccaccag atgggcatta aacgagtatc ccggcagcag   3420

gggatcattt tgcgcttcag ccatactttt catactcccg ccattcagag aagaaaccaa   3480

ttgtccatat tgcatcagac attgccgtca ctgcgtcttt tactggctct tctcgctaac   3540

caaaccggta accccgctta ttaaaagcat tctgtaacaa agcgggacca aagccatgac   3600

aaaaacgcgt aacaaaagtg tctataatca cggcagaaaa gtccacattg attatttgca   3660

cggcgtcaca ctttgctatg ccatagcatt tttatccata agattagcgg atcctacctg   3720

acgcttttta tcgcaactct ctactgtttc tccatacccg ttttttgggg ctagagaatt   3780

cgtc                                                                 3784
```

```
<210> SEQ ID NO 20
<211> LENGTH: 3740
<212> TYPE: DNA
<213> ORGANISM: Escherichia coli

<400> SEQUENCE: 20

aacgaattca agcttgatat cattcaggac gagcctcaga ctccagcgta actggactga     60

aaacaaacta aagcgccctt gtggcgcttt agttttgttc cgcggccacc ggctggctcg    120
```

-continued

```
cttcgctcgg cccgtggaca accctgctgg acaagctgat ggacaggctg cgcctgccca    180
cgagcttgac cacagggatt gcccaccggc tacccagcct tcgaccacat acccaccggc    240
tccaactgcg cggcctgcgg ccttgcccca tcaatttttt taattttctc tggggaaaag    300
cctccggcct gcggcctgcg cgcttcgctt gccggttgga caccaagtgg aaggcgggtc    360
aaggctcgcg cagcgaccgc gcagcggctt ggccttgacg cgcctggaac gacccaagcc    420
tatgcgagtg ggggcagtcg aaggcgaagc ccgcccgcct gccccccgag cctcacggcg    480
gcgagtgcgg gggttccaag gggggcagcgc caccttgggc aaggccgaag gccgcgcagt    540
cgatcaacaa gccccggagg ggccactttt tgccggaggg ggagccgcgc cgaaggcgtg    600
ggggaacccc gcaggggtgc ccttctttgg gcaccaaaga actagatata gggcgaaatg    660
cgaaagactt aaaaatcaac aacttaaaaa agggggggtac gcaacagctc attgcggcac    720
cccccgcaat agctcattgc gtaggttaaa gaaaatctgt aattgactgc cacttttacg    780
caacgcataa ttgttgtcgc gctgccgaaa agttgcagct gattgcgcat ggtgccgcaa    840
ccgtgcggca ccctaccgca tggagataag catggccacg cagtccagag aaatcggcat    900
tcaagccaag aacaagcccg gtcactgggt gcaaacggaa cgcaaagcgc atgaggcgtg    960
ggccgggctt attgcgagga aacccacggc ggcaatgctg ctgcatcacc tcgtggcgca   1020
gatgggccac cagaacgccg tggtggtcag ccagaagaca ctttccaagc tcatcggacg   1080
ttctttgcgg acggtccaat acgcagtcaa ggacttggtg gccgagcgct ggatctccgt   1140
cgtgaagctc aacggccccg gcaccgtgtc ggcctacgtg gtcaatgacc gcgtggcgtg   1200
gggccagccc cgcgaccagt tgcgcctgtc ggtgttcagt gccgccgtgg tggttgatca   1260
cgacgaccag gacgaatcgc tgttggggca tggcgacctg cgccgcatcc cgaccctgta   1320
tccgggcgag cagcaactac cgaccggccc cggcgaggag ccgcccagcc agcccggcat   1380
tccgggcatg gaaccagacc tgccagcctt gaccgaaacg gaggaatggg aacggcgcgg   1440
gcagcagcgc ctgccgatgc ccgatgagcc gtgttttctg gacgatggcg agccgttgga   1500
gccgccgaca cgggtcacgc tgccgcgccg gtagtacgta agaggttcca actttcacca   1560
taatgaaata agatcactac cgggcgtatt ttttgagtta tcgagatttt caggagctaa   1620
ggaagctaaa atgagccata ttcaacggga aacgtcttgc tcgaggccgc gattaaattc   1680
caacatggat gctgatttat atgggtataa atgggctcgc gataatgtcg ggcaatcagg   1740
tgcgacaatc tatcgattgt atgggaagcc cgatgcgcca gagttgtttc tgaaacatgg   1800
caaaggtagc gttgccaatg atgttacaga tgagatggtc aggctaaact ggctgacgga   1860
atttatgcct cttccgacca tcaagcattt tatccgtact cctgatgatg catggttact   1920
caccactgcg atccccaggga aaacagcatt ccaggtatta gaagaatatc ctgattcagg   1980
tgaaaatatt gttgatgcgc tggcagtgtt cctgcgccgg ttgcattcga ttcctgtttg   2040
taattgtcct tttaacggcg atcgcgtatt tcgtctcgct caggcgcaat cacgaatgaa   2100
taacggtttg gttggtgcga gtgattttga tgacgagcgt aatggctggc ctgttgaaca   2160
agtctggaaa gaaatgcata agcttttgcc attctcaccg gattcagtcg tcactcatgg   2220
tgatttctca cttgataacc ttatttttga cgaggggaaa ttaataggtt gtattgatgt   2280
tggacgagtc ggaatcgcag accgatacca ggatcttgcc atcctatgga actgcctcgg   2340
tgagttttct ccttcattac agaaacggct ttttcaaaaa tatggtattg ataatcctga   2400
tatgaataaa ttgcagtttc acttgatgct cgatgagttt ttctgagggc ggatcccccct   2460
```

-continued

```
caagtcaaaa gcctccggtc ggaggctttt gactttctgc tatggaggtc aggtatgatt   2520

tttatgacaa cttgacggct acatcattca ctttttcttc acaaccggca cggaactcgc   2580

tcgggctggc cccggtgcat tttttaaata cccgcgagaa atagagttga tcgtcaaaac   2640

caacattgcg accgacggtg gcgataggca tccgggtggt gctcaaaagc agcttcgcct   2700

ggctgatacg ttggtcctcg cgccagctta agacgctaat ccctaactgc tggcggaaaa   2760

gatgtgacag acgcgacggc gacaagcaaa catgctgtgc gacgctggcg atatcaaaat   2820

tgctgtctgc caggtgatcg ctgatgtact gacaagcctc gcgtacccga ttatccatcg   2880

gtggatggag cgactcgtta atcgcttcca tgcgccgcag taacaattgc tcaagcagat   2940

ttatcgccag cagctccgaa tagcgccctt ccccttgccc ggcgttaatg atttgcccaa   3000

acaggtcgct gaaatgcggc tggtgcgctt catccgggcg aaagaacccc gtattggcaa   3060

atattgacgg ccagttaagc cattcatgcc agtaggcgcg cggacgaaag taaacccact   3120

ggtgatacca ttcgcgagcc tccggatgac gaccgtagtg atgaatctct cctggcggga   3180

acagcaaaat atcacccggt cggcaaacaa attctcgtcc ctgatttttc accacccccct  3240

gaccgcgaat ggtgagattg agaatataac ctttcattcc cagcggtcgg tcgataaaaa   3300

aatcgagata accgttggcc tcaatcggcg ttaaacccgc caccagatgg gcattaaacg   3360

agtatcccgg cagcagggga tcattttgcg cttcagccat acttttcata ctcccgccat   3420

tcagagaaga aaccaattgt ccatattgca tcagacattg ccgtcactgc gtcttttact   3480

ggctcttctc gctaaccaaa ccggtaaccc cgcttattaa aagcattctg taacaaagcg   3540

ggaccaaagc catgacaaaa acgcgtaaca aaagtgtcta taatcacggc agaaaagtcc   3600

acattgatta tttgcacggc gtcacacttt gctatgccat agcattttta tccataagat   3660

tagcggatcc tacctgacgc tttttatcgc aactctctac tgtttctcca tacccgtttt   3720

tttgggctag agaattcgtc                                                3740
```

<210> SEQ ID NO 21
<211> LENGTH: 3586
<212> TYPE: DNA
<213> ORGANISM: Escherichia coli

<400> SEQUENCE: 21

```
aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180

cgagcttgac cacagggatt gcccaccggc tacccagcct tcgaccacat acccaccggc    240

tccaactgcg cggcctgcgg ccttgcccca tcaatttttt taatttttctc tggggaaaag   300

cctccggcct gcggcctgcg cgcttcgctt gccggttgga caccaagtgg aaggcgggtc    360

aaggctcgcg cagcgaccgc gcagcggctt ggccttgacg cgcctggaac gacccaagcc    420

tatgcgagtg ggggcagtcg aaggcgaagc ccgcccgcct gccccccgag cctcacggcg    480

gcgagtgcgg gggttccaag gggcagcgc caccttgggc aaggccgaag gccgcgcagt     540

cgatcaacaa gccccggagg ggccactttt tgccggaggg ggagccgcgc cgaaggcgtg    600

ggggaacccc gcaggggtgc ccttctttgg gcaccaaaga actagatata gggcgaaatg    660

cgaaagactt aaaaatcaac aacttaaaaa aggggggtac gcaacagctc attgcggcac    720

cccccgcaat agctcattgc gtaggttaaa gaaaatctgt aattgactgc cacttttacg    780

caacgcataa ttgttgtcgc gctgccgaaa agttgcagct gattgcgcat ggtgccgcaa    840
```

-continued

```
ccgtgcggca ccctaccgca tggagataag catggccacg cagtccagag aaatcggcat    900
tcaagccaag aacaagcccg gtcactgggt gcaaacggaa cgcaaagcgc atgaggcgtg    960
ggccgggctt attgcgagga aacccacggc ggcaatgctg ctgcatcacc tcgtggcgca   1020
gatgggccac cagaacgccg tggtggtcag ccagaagaca ctttccaagc tcatcggacg   1080
ttctttgcgg acggtccaat acgcagtcaa ggacttggtg gccgagcgct ggatctccgt   1140
cgtgaagctc aacggccccg gcaccgtgtc ggcctacgtg gtcaatgacc gcgtggcgtg   1200
gggccagccc cgcgaccagt tgcgcctgtc ggtgttcagt gccgccgtgg tggttgatca   1260
cgacgaccag gacgaatcgc tgttggggca tggcgacctg cgccgcatcc cgaccctgta   1320
tccgggcgag cagcaactac cgaccggccc cggcgaggag ccgcccagcc agcccggcat   1380
tccgggcatg gaaccagacc tgccagcctt gaccgaaacg gaggaatggg aacggcgcgg   1440
gcagcagcgc ctgccgatgc ccgatgagcc gtgttttctg gacgatggcg agccgttgga   1500
gccgccgaca cgggtcacgc tgccgcgccg gtagtacgta agaggttcca actttcacca   1560
taatgaaata agatcactac cgggcgtatt ttttgagtta tcgagatttt caggagctaa   1620
ggaagctaaa atggagaaaa aaatcactgg atataccacc gttgatatat cccaatggca   1680
tcgtaaagaa cattttgagg catttcagtc agttgctcaa tgtacctata accagaccgt   1740
tcagctggat attacggcct ttttaaagac cgtaaagaaa aataagcaca agttttatcc   1800
ggcctttatt cacattcttg cccgcctgat gaatgctcat ccggaattcc gtatggcaat   1860
gaaagacggt gagctggtga tatgggatag tgttcaccct tgttacaccg ttttccatga   1920
gcaaactgaa acgttttcat cgctctggag tgaataccac gacgatttcc ggcagtttct   1980
acacatatat tcgcaagatg tggcgtgtta cggtgaaaac ctggcctatt tccctaaagg   2040
gtttattgag aatatgtttt tcgtctcagc caatccctgg gtgagtttca ccagttttga   2100
tttaaacgtg gccaatatgg acaacttctt cgcccccgtt ttcaccatgg gcaaatatta   2160
tacgcaaggc gacaaggtgc tgatgccgct ggcgattcag gttcatcatg ccgtttgtga   2220
tggcttccat gtcggcagaa tgcttaatga attacaacag tactgcgatg agtggcaggg   2280
cggggcgtaa acgcgtggat ccccctcaag tcaaaagcct ccggtcggag gcttttgact   2340
ttctgctatg gaggtcaggt atgattttta tgacaacttg acggctacat cattcacttt   2400
ttcttcacaa ccggcacgga actcgctcgg gctggccccg gtgcattttt taaatacccg   2460
cgagaaatag agttgatcgt caaaaccaac attgcgaccg acggtggcga taggcatccg   2520
ggtggtgctc aaaagcagct tcgcctggct gatacgttgg tcctcgcgcc agcttaagac   2580
gctaatccct aactgctggc ggaaaagatg tgacagacgc gacggcgaca agcaaacatg   2640
ctgtgcgacg ctggcgatat caaaattgct gtctgccagg tgatcgctga tgtactgaca   2700
agcctcgcgt acccgattat ccatcggtgg atggagcgac tcgttaatcg cttccatgcg   2760
ccgcagtaac aattgctcaa gcagatttat cgccagcagc tccgaatagc gcccttcccc   2820
ttgcccggcg ttaatgattt gcccaaacag gtcgctgaaa tgcggctggt gcgcttcatc   2880
cgggcgaaag aaccccgtat tggcaaatat tgacggccag ttaagccatt catgccagta   2940
ggcgcgcgga cgaaagtaaa cccactggtg ataccattcg cgagcctccg gatgacgacc   3000
gtagtgatga atctctcctg gcgggaacag caaaatatca cccggtcggc aaacaaattc   3060
tcgtccctga tttttcacca ccccctgacc gcgaatggtg agattgagaa tataaccttt   3120
cattcccagc ggtcggtcga taaaaaaatc gagataaccg ttggcctcaa tcggcgttaa   3180
```

-continued

```
acccgccacc agatgggcat taaacgagta tcccggcagc aggggatcat tttgcgcttc   3240

agccatactt ttcatactcc cgccattcag agaagaaacc aattgtccat attgcatcag   3300

acattgccgt cactgcgtct tttactggct cttctcgcta accaaaccgg taaccccgct   3360

tattaaaagc attctgtaac aaagcgggac caaagccatg acaaaaacgc gtaacaaaag   3420

tgtctataat cacggcagaa aagtccacat tgattatttg cacggcgtca cactttgcta   3480

tgccatagca tttttatcca taagattagc ggatcctacc tgacgctttt tatcgcaact   3540

ctctactgtt tctccatacc cgtttttttg ggctagagaa ttcgtc                  3586
```

```
<210> SEQ ID NO 22
<211> LENGTH: 4118
<212> TYPE: DNA
<213> ORGANISM: Escherichia coli

<400> SEQUENCE: 22

aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180

cgagcttgac cacagggatt gcccaccggc tacccagcct tcgaccacat acccaccggc    240

tccaactgcg cggcctgcgg ccttgcccca tcaatttttt taattttctc tggggaaaag    300

cctccggcct gcggcctgcg cgcttcgctt gccggttgga caccaagtgg aaggcgggtc    360

aaggctcgcg cagcgaccgc gcagcggctt ggccttgacg cgcctggaac gacccaagcc    420

tatgcgagtg gggcagtcg aaggcgaagc ccgcccgcct gccccccgag cctcacggcg    480

gcgagtgcgg gggttccaag gggcagcgc caccttgggc aaggccgaag gccgcgcagt    540

cgatcaacaa gccccggagg ggccactttt tgccggaggg ggagccgcgc cgaaggcgtg    600

ggggaacccc gcaggggtgc ccttctttgg gcaccaaaga actagatata gggcgaaatg    660

cgaaagactt aaaaatcaac aacttaaaaa agggggggtac gcaacagctc attgcggcac    720

cccccgcaat agctcattgc gtaggttaaa gaaaatctgt aattgactgc cacttttacg    780

caacgcataa ttgttgtcgc gctgccgaaa agttgcagct gattgcgcat ggtgccgcaa    840

ccgtgcggca ccctaccgca tggagataag catggccacg cagtccagag aaatcggcat    900

tcaagccaag aacaagcccg gtcactgggt gcaaacggaa cgcaaagcgc atgaggcgtg    960

ggccgggctt attgcgagga aacccacggc ggcaatgctg ctgcatcacc tcgtggcgca   1020

gatgggccac cagaacgccg tggtggtcag ccagaagaca ctttccaagc tcatcggacg   1080

ttctttgcgg acggtccaat acgcagtcaa ggacttggtg gccgagcgct ggatctccgt   1140

cgtgaagctc aacggccccg gcaccgtgtc ggcctacgtg gtcaatgacc gcgtggcgtg   1200

gggccagccc cgcgaccagt tgcgcctgtc ggtgttcagt gccgccgtgg tggttgatca   1260

cgacgaccag gacgaatcgc tgttggggca tggcgacctg cgccgcatcc cgaccctgta   1320

tccgggcgag cagcaactac cgaccggccc cggcgaggag ccgcccagcc agcccggcat   1380

tccgggcatg gaaccagacc tgccagcctt gaccgaaacg gaggaatggg aacggcgcgg   1440

gcagcagcgc ctgccgatgc ccgatgagcc gtgttttctg gacgatggcg agccgttgga   1500

gccgccgaca cgggtcacgc tgccgcgccg gtagtacgta agaggttcca actttcacca   1560

taatgaaata agatcactac cgggcgtatt ttttgagtta tcgagatttt caggagctaa   1620

ggaagctaaa atgaaatcta acaatgcgct catcgtcatc ctcggcaccg tcaccctgga   1680

tgctgtaggc ataggcttgg ttatgccggt actgccgggc ctcttgcggg atatcgtcca   1740
```

-continued

```
ttccgacagc atcgccagtc actatggcgt gctgctagcg ctatatgcgt tgatgcaatt   1800
tctatgcgca cccgttctcg gagcactgtc cgaccgcttt ggccgccgcc cagtcctgct   1860
cgcttcgcta cttggagcca ctatcgacta cgcgatcatg gcgaccacac ccgtcctgtg   1920
gatcctctac gccggacgca tcgtggccgg catcaccggc gccacaggtg cggttgctgg   1980
cgcctatatc gccgacatca ccgatgggga agatcgggct cgccacttcg ggctcatgag   2040
cgcttgtttc ggcgtgggta tggtggcagg ccccgtggcc gggggactgt tgggcgccat   2100
ctccttgcat gcaccattcc ttgcggcggc ggtgctcaac ggcctcaacc tactactggg   2160
ctgcttccta atgcaggagt cgcataaggg agagcgtcga ccgatgccct tgagagcctt   2220
caacccagtc agctccttcc ggtgggcgcg gggcatgact atcgtcgccg cacttatgac   2280
tgtcttcttt atcatgcaac tcgtaggaca ggtgccggca gcgctctggg tcattttcgg   2340
cgaggaccgc tttcgctgga gcgcgacgat gatcggcctg tcgcttgcgg tattcggaat   2400
cttgcacgcc ctcgctcaag ccttcgtcac tggtcccgcc accaaacgtt tcggcgagaa   2460
gcaggccatt atcgccggca tggcggccga cgcgctgggc tacgtcttgc tggcgttcgc   2520
gacgcgaggc tggatggcct tccccattat gattcttctc gcttccggcg gcatcgggat   2580
gcccgcgttg caggccatgc tgtccaggca ggtagatgac gaccatcagg gacagcttca   2640
aggatcgctc gcggctctta ccagcctaac ttcgatcact ggaccgctga tcgtcacggc   2700
gatttatgcc gcctcggcga gcacatggaa cgggttggca tggattgtag gcgccgccct   2760
ataccttgtc tgcctccccg cgttgcgtcg cggtgcatgg agccgggcca cctcgacctg   2820
aatggaaggg atcccccctca agtcaaaagc ctccggtcgg aggcttttga ctttctgcta   2880
tggaggtcag gtatgatttt tatgacaact tgacggctac atcattcact ttttcttcac   2940
aaccggcacg gaactcgctc gggctggccc cggtgcattt tttaaatacc cgcgagaaat   3000
agagttgatc gtcaaaacca acattgcgac cgacggtggc gataggcatc cgggtggtgc   3060
tcaaaagcag cttcgcctgg ctgatacgtt ggtcctcgcg ccagcttaag acgctaatcc   3120
ctaactgctg gcggaaaaga tgtgacagac gcgacggcga caagcaaaca tgctgtgcga   3180
cgctggcgat atcaaaattg ctgtctgcca ggtgatcgct gatgtactga caagcctcgc   3240
gtacccgatt atccatcggt ggatggagcg actcgttaat cgcttccatg cgccgcagta   3300
acaattgctc aagcagattt atcgccagca gctccgaata gcgcccttcc ccttgcccgg   3360
cgttaatgat ttgcccaaac aggtcgctga aatgcggctg gtgcgcttca tccgggcgaa   3420
agaaccccgt attggcaaat attgacggcc agttaagcca ttcatgccag taggcgcgcg   3480
gacgaaagta aacccactgg tgataccatt cgcgagcctc cggatgacga ccgtagtgat   3540
gaatctctcc tggcgggaac agcaaaatat cacccggtcg gcaaacaaat tctcgtccct   3600
gatttttcac cacccccctga ccgcgaatgg tgagattgag aatataacct ttcattccca   3660
gcggtcggtc gataaaaaaa tcgagataac cgttggcctc aatcggcgtt aaacccgcca   3720
ccagatgggc attaaacgag tatcccggca gcaggggatc attttgcgct tcagccatac   3780
ttttcatact cccgccattc agagaagaaa ccaattgtcc atattgcatc agacattgcc   3840
gtcactgcgt cttttactgg ctcttctcgc taaccaaacc ggtaaccccg cttattaaaa   3900
gcattctgta acaaagcggg accaaagcca tgacaaaaac gcgtaacaaa agtgtctata   3960
atcacggcag aaaagtccac attgattatt tgcacggcgt cacactttgc tatgccatag   4020
catttttatc cataagatta gcggatccta cctgacgctt tttatcgcaa ctctctactg   4080
```

tttctccata cccgtttttt tgggctagag aattcgtc 4118

<210> SEQ ID NO 23
<211> LENGTH: 3161
<212> TYPE: DNA
<213> ORGANISM: Escherichia coli

<400> SEQUENCE: 23
aacgaattca agcttgatat cattcaggac gagcctcaga ctccagcgta actggactga 60
aaacaaacta aagcgccctt gtggcgcttt agttttgttc cgcggccacc ggctggctcg 120
cttcgctcgg cccgtggaca accctgctgg acaagctgat ggacaggctg cgcctgccca 180
cgagcttgac cacagggatt gcccaccggc tacccagcct tcgaccacat acccaccggc 240
tccaactgcg cggcctgcgg ccttgcccca tcaatttttt taatttttctc tggggaaaag 300 cctccggcct gcggcctgcg cgcttcgctt gccggttgga caccaagtgg aaggcgggtc 360
aaggctcgcg cagcgaccgc gcagcggctt ggccttgacg cgcctggaac gacccaagcc 420
tatgcgagtg ggggcagtcg aaggcgaagc ccgcccgcct gccccccgag cctcacggcg 480
gcgagtgcgg gggttccaag gggcagcgc caccttgggc aaggccgaag gccgcgcagt 540
cgatcaacaa gccccggagg ggccactttt tgccggaggg ggagccgcgc cgaaggcgtg 600
ggggaacccc gcaggggtgc ccttctttgg gcaccaaaga actagatata gggcgaaatg 660
cgaaagactt aaaaatcaac aacttaaaaa aggggggtac gcaacagctc attgcggcac 720
cccccgcaat agctcattgc gtaggttaaa gaaaatctgt aattgactgc cacttttacg 780
caacgcataa ttgttgtcgc gctgccgaaa agttgcagct gattgcgcat ggtgccgcaa 840
ccgtgcggca ccctaccgca tggagataag catggccacg cagtccagag aaatcggcat 900
tcaagccaag aacaagcccg gtcactgggt gcaaacggaa cgcaaagcgc atgaggcgtg 960
ggccgggctt attgcgagga aacccacggc ggcaatgctg ctgcatcacc tcgtggcgca 1020
gatgggccac cagaacgccg tggtggtcag ccagaagaca ctttccaagc tcatcggacg 1080
ttctttgcgg acggtccaat acgcagtcaa ggacttggtg gccgagcgct ggatctccgt 1140
cgtgaagctc aacggccccg gcaccgtgtc ggcctacgtg gtcaatgacc gcgtggcgtg 1200
gggccagccc cgcgaccagt tgcgcctgtc ggtgttcagt gccgccgtgg tggttgatca 1260
cgacgaccag gacgaatcgc tgttggggca tggcgacctg cgccgcatcc cgaccctgta 1320
tccgggcgag cagcaactac cgaccggccc cggcgaggag ccgcccagcc agcccggcat 1380
tccgggcatg gaaccagacc tgccagcctt gaccgaaacg gaggaatggg aacggcgcgg 1440
gcagcagcgc ctgccgatgc ccgatgagcc gtgttttctg gacgatggcg agccgttgga 1500
gccgccgaca cgggtcacgc tgccgcgccg gtagtacgta agaggttcca actttcacca 1560
taatgaaata agatcactac cgggcgtatt ttttgagtta tcgagatttt caggagctaa 1620
ggaagctaaa atgggtcaaa gtagcgatga agccaacgct cccgttgcag ggcagtttgc 1680
gcttcccctg agtgccacct ttggcttagg ggatcgcgta cgcaagaaat ctggtgccgc 1740
ttggcagggt caagtcgtcg gttggtattg cacaaaactc actcctgaag gctatgcggt 1800
cgagtccgaa tcccacccag gctcagtgca aatttatcct gtggctgcac ttgaacgtgt 1860
ggcctaagaa tggatccccc tcaagtcaaa agcctccggt cggaggcttt tgactttctg 1920
ctatggaggt caggtatgat tttatgaca acttgacggc tacatcattc actttttctt 1980
cacaaccggc acggaactcg ctcgggctgg ccccggtgca ttttttaaat acccgcgaga 2040
aatagagttg atcgtcaaaa ccaacattgc gaccgacggt ggcgataggc atccgggtgg 2100

-continued

```
tgctcaaaag cagcttcgcc tggctgatac gttggtcctc gcgccagctt aagacgctaa   2160

tccctaactg ctggcggaaa agatgtgaca gacgcgacgg cgacaagcaa acatgctgtg   2220

cgacgctggc gatatcaaaa ttgctgtctg ccaggtgatc gctgatgtac tgacaagcct   2280

cgcgtacccg attatccatc ggtggatgga gcgactcgtt aatcgcttcc atgcgccgca   2340

gtaacaattg ctcaagcaga tttatcgcca gcagctccga atagcgccct tcccctttgcc  2400

cggcgttaat gatttgccca aacaggtcgc tgaaatgcgg ctggtgcgct tcatccgggc   2460

gaaagaaccc cgtattggca aatattgacg gccagttaag ccattcatgc cagtaggcgc   2520

gcggacgaaa gtaaacccac tggtgatacc attcgcgagc ctccggatga cgaccgtagt   2580

gatgaatctc tcctggcggg aacagcaaaa tatcacccgg tcggcaaaca aattctcgtc   2640

cctgattttt caccaccccc tgaccgcgaa tggtgagatt gagaatataa cctttcattc   2700

ccagcggtcg gtcgataaaa aaatcgagat aaccgttggc ctcaatcggc gttaaacccg   2760

ccaccagatg ggcattaaac gagtatcccg gcagcagggg atcattttgc gcttcagcca   2820

tacttttcat actcccgcca ttcagagaag aaaccaattg tccatattgc atcagacatt   2880

gccgtcactg cgtcttttac tggctcttct cgctaaccaa accggtaacc ccgcttatta   2940

aaagcattct gtaacaaagc gggaccaaag ccatgacaaa aacgcgtaac aaaagtgtct   3000

ataatcacgg cagaaaagtc cacattgatt atttgcacgg cgtcacactt tgctatgcca   3060

tagcattttt atccataaga ttagcggatc ctacctgacg ctttttatcg caactctcta   3120

ctgtttctcc atacccgttt ttttgggcta gagaattcgt c                       3161
```

<210> SEQ ID NO 24
<211> LENGTH: 5799
<212> TYPE: DNA
<213> ORGANISM: Escherichia coli

<400> SEQUENCE: 24

```
aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180

cgagcttgac cacagggatt gcccaccggc tacccagcct tcgaccacat acccaccggc    240

tccaactgcg cggcctgcgg ccttgcccca tcaatttttt taattttctc tggggaaaag    300

cctccggcct gcggcctgcg cgcttcgctt gccggttgga caccaagtgg aaggcgggtc    360

aaggctcgcg cagcgaccgc gcagcggctt ggccttgacg cgcctggaac gacccaagcc    420

tatgcgagtg ggggcagtcg aaggcgaagc ccgcccgcct gccccccgag cctcacggcg    480

gcgagtgcgg gggttccaag gggcagcgc caccttgggc aaggccgaag gccgcgcagt     540

cgatcaacaa gccccggagg ggccactttt tgccggaggg ggagccgcgc cgaaggcgtg    600

ggggaacccc gcaggggtgc ccttctttgg gcaccaaaga actagatata gggcgaaatg    660

cgaaagactt aaaaatcaac aacttaaaaa aggggggtac gcaacagctc attgcggcac    720

cccccgcaat agctcattgc gtaggttaaa gaaaatctgt aattgactgc cacttttacg    780

caacgcataa ttgttgtcgc gctgccgaaa agttgcagct gattgcgcat ggtgccgcaa    840

ccgtgcggca ccctaccgca tggagataag catggccacg cagtccagag aaatcggcat    900

tcaagccaag aacaagcccg gtcactgggt gcaaacggaa cgcaaagcgc atgaggcgtg    960

ggccgggctt attgcgagga aacccacggc ggcaatgctg ctgcatcacc tcgtggcgca   1020
```

-continued

```
gatgggccac cagaacgccg tggtggtcag ccagaagaca ctttccaagc tcatcggacg   1080

ttctttgcgg acggtccaat acgcagtcaa ggacttggtg gccgagcgct ggatctccgt   1140

cgtgaagctc aacggccccg gcaccgtgtc ggcctacgtg gtcaatgacc gcgtggcgtg   1200

gggccagccc cgcgaccagt tgcgcctgtc ggtgttcagt gccgccgtgg tggttgatca   1260

cgacgaccag gacgaatcgc tgttggggca tggcgacctg cgccgcatcc cgaccctgta   1320

tccgggcgag cagcaactac cgaccggccc cggcgaggag ccgcccagcc agcccggcat   1380

tccgggcatg gaaccagacc tgccagcctt gaccgaaacg gaggaatggg aacggcgcgg   1440

gcagcagcgc ctgccgatgc ccgatgagcc gtgttttctg gacgatggcg agccgttgga   1500

gccgccgaca cgggtcacgc tgccgcgccg gtagtacgta agaggttcca actttcacca   1560

taatgaaata agatcactac cgggcgtatt ttttgagtta tcgagatttt caggagctaa   1620

ggaagctaaa atggaagaac aaagcgtgaa catggcgcga ttgaaggggg aggttttgcc   1680

cgccctcttc gcgtcgccgg cgacgattgg cgagtacggg gccggcatcg acggggcgga   1740

ttccctcaac gagctgtcga atctgatgga gcacggcgca gttgccgcgc tggccgacaa   1800

aatcagccag atcgtggcga agctggccga cgcggacccc cgcaagatcg cggaaaagcc   1860

tacctggttc gagaagatgc ttggccgtga ggttgaacgc caggtgaggt atcaggtcgc   1920

ccgcaagacg ctcgaccagt tgctggacga agccgagggc gtagcgcagc gcgtgcggga   1980

cacgttgcgc gccttggatg acatgctcaa tacgcatgag gccgaggtag accggctcag   2040

agcctacatt caagccgggc gcgagttcct ggacgagaac cccgaggccg gcgcggccaa   2100

ggccggcgtg atcgagttcg acaagccgcg cgaacgcttc gcgcgcaagc tcgccaacct   2160

ggcaaccctc atggcgtccc atgaaatgag cgtcactcag atgaagctca cgcgggcgca   2220

ggccgtggac atgctggacc gcttctctga aacggcatcc gtcctggtgc ccgtctggcg   2280

tcagcacacc ctcgcgctca tcaccaccaa gaacatgaat ccggcaatgg tcgccgaggc   2340

ggccaaagct caccaggcgc tcatgcggag cctttcgcag agcctggaag gcatcaacca   2400

ataacacggc gggagaaccc tatgaacgca ctgaaaacga cgcacgacgc caaggcccct   2460

atcgtcgcct tcgacatgac ccccggcaacc ctgcgcgagc tgggcttgca ggaaagcgac   2520

gtgccggaag tccatgcggt cgcgcagcgg atcgaggtcg gcagtccgca gaccgttgcc   2580

gagttcggcc gcgacgtggc cgagcacacg tcccgctacg ccgatagcct gctggaccag   2640

gtgcgcaaca gcgacctgga cgaagcaggc gagaaactga cccaggttgt cgccaaggcc   2700

cgttccctga acgtcggccc tttgtccgac aaccgttccc gcctgcccct gattggcccg   2760

ctgatcgacc gcttccgcgt ccgttcgacg ggcttcatgg cgcgcttcga cacgacccgc   2820

gagcagatcg aacacctggt cagcgaagtg cagaccaccc agcaaggcat cgcgcagcgc   2880

aatgcctcgc tcgacgaaat gttcgcagcc gtgcgcgagg aacaccgcct tcttggcgtc   2940

cacatcgcgg ccggcaaggt ccgccttgcc gagctgcgcg agcaggccga gggtctgcgc   3000

ggcaatgtcg ggaacgaccc gggccgcgtg caggagctgg ccgacctcga tgcgatggtt   3060

gccaacctgg acaagcgcat cggcgacctg atcgccttgc aacattcggc catgcagagc   3120

ctgccgacca tccgcatgat ccaggccaac aaccagatgc tggtcgataa attccacacc   3180

atccgcgaaa tcaccgtgcc ggcgtggaag cggcaattca tgctggcctt gagcctcaac   3240

gagcagaaga acgccgtcga actggccacg gccatcgacg acaccaccaa cgacctgatg   3300

aagcgcaatg cggccctgct gcatcgcacg tccgtcgaga cggcgaagga gaaccaacgc   3360

ctggtgatcg acgtggacac gctcaagcag gttcagacga cgctcatcaa gaccgtcgag   3420
```

-continued

```
gacgttattc gcatccagca ggaaggcgtg cagaagcgca aggatgccga gaagcagatc   3480
gccgcaatgc gtggcgatct tcaagccaag ctgacccgcc agcccgtgcg cgagctggcc   3540
caacaggagt ccgtatgaat gccacaaaca ccgatgtttt cgcccaggta ggcggcctcg   3600
aggcccgagg cgcgaagatg aagaagcggg gcacccgctt cctcatcgcg gcgctggcag   3660
tccttgccat tgccgggatc ggggcagtaa cgggatgggc gatcagcccg agcgcgacgc   3720
ccggaagcat tgacgtgccg caggtgctgg catcgacatt cagcgaccag gtgccgggca   3780
gtgagggcgg cggcctgggt ggcggcctgc ccttcacttc ggccgtcggg gcattcacgg   3840
acttcatggc ggggccggca atttttacct tgggcattct tggcatagtg gtcgcgggtg   3900
ccgtgctcgt gttcgggggt gaattctgcg ggttcgtgcg atccgtctgc atgatggtga   3960
tagccgtcag catgattttc gtgtcgtcga acttggtgaa gggcattctc ggcggcgatc   4020
acgacgccgg ccctgcggag ccttcgccgc gtgcgcgatt catggcggcc gtggaggcca   4080
aggatttcgc gcgagtgcaa gagctgatcg aggcgcgtgg agccaagtcg gcggctgatt   4140
atgtccttgc gcagctcgcc gtggccgaag gtctggaccg caagcctggt gcgcgcgtcg   4200
tggtcgggaa agcggcgggc agcatggcaa tgccgcctgc ggcgctgggt tttacgccaa   4260
ggggagaagc ggcatacgcc atcgagcggt cagcctatgg tgagccgagg tccagcattg   4320
cgaagcagta ccagcaggaa tggaaccgga aggcggcgac ctggtgggcg atggccggtg   4380
tggccggcat catcggcgcg atcctggcgg cggcggcaac cggctttgtt gggctggcag   4440
tgtcgatccg caaccgagtg aagcgcgtgc gcgacctgtt ggtgatggag ccgggtgcag   4500
agccataagg gatcccccctc aagtcaaaag cctccggtcg gaggcttttg actttctgct   4560
atggaggtca ggtatgattt ttatgacaac ttgacggcta catcattcac tttttcttca   4620
caaccggcac ggaactcgct cgggctggcc ccggtgcatt ttttaaatac ccgcgagaaa   4680
tagagttgat cgtcaaaacc aacattgcga ccgacggtgg cgataggcat ccgggtggtg   4740
ctcaaaagca gcttcgcctg gctgatacgt tggtcctcgc gccagcttaa gacgctaatc   4800
cctaactgct ggcggaaaag atgtgacaga cgcgacggcg acaagcaaac atgctgtgcg   4860
acgctggcga tatcaaaatt gctgtctgcc aggtgatcgc tgatgtactg acaagcctcg   4920
cgtacccgat tatccatcgg tggatggagc gactcgttaa tcgcttccat gcgccgcagt   4980
aacaattgct caagcagatt tatcgccagc agctccgaat agcgcccttc cccttgcccg   5040
gcgttaatga tttgcccaaa caggtcgctg aaatgcggct ggtgcgcttc atccgggcga   5100
aagaaccccg tattggcaaa tattgacggc cagttaagcc attcatgcca gtaggcgcgc   5160
ggacgaaagt aaacccactg gtgataccat tcgcgagcct ccggatgacg accgtagtga   5220
tgaatctctc ctggcgggaa cagcaaaata tcacccggtc ggcaaacaaa ttctcgtccc   5280
tgatttttca ccaccccctg accgcgaatg gtgagattga gaatataacc tttcattccc   5340
agcggtcggt cgataaaaaa atcgagataa ccgttggcct caatcggcgt taaacccgcc   5400
accagatggg cattaaacga gtatcccggc agcaggggat cattttgcgc ttcagccata   5460
cttttcatac tcccgccatt cagagaagaa accaattgtc catattgcat cagacattgc   5520
cgtcactgcg tcttttactg gctcttctcg ctaaccaaac cggtaacccc gcttattaaa   5580
agcattctgt aacaaagcgg gaccaaagcc atgacaaaaa cgcgtaacaa aagtgtctat   5640
aatcacggca gaaaagtcca cattgattat ttgcacggcg tcacactttg ctatgccata   5700
gcatttttat ccataagatt agcggatcct acctgacgct ttttatcgca actctctact   5760
```

-continued gtttctccat acccgttttt ttgggctaga gaattcgtc 5799

<210> SEQ ID NO 25
<211> LENGTH: 3907
<212> TYPE: DNA
<213> ORGANISM: Escherichia coli

<400> SEQUENCE: 25
aacgaattca agcttgatat cattcaggac gagcctcaga ctccagcgta actggactga 60
aaacaaacta aagcgccctt gtggcgcttt agttttgttc cgctcatgat aataatggtt 120
tcttagacgt caggtggcac ttttcgggga aatgtgcgcg cccgcgttcc tgctggcgct 180
gggcctgttt ctggcgctgg acttcccgct gttccgtcag cagcttttcg cccacggcct 240
tgatgatcgc ggcggccttg gcctgcatat cccgattcaa cggccccagg gcgtccagaa 300
cgggcttcag gcgctcccga aggtctcggg ccgtctcttg ggcttgatcg gccttcttgc 360
gcatctcacg cgctcctgcg gcggcctgta gggcaggctc atacccctgc cgaaccgctt 420
ttgtcagccg gtcggccacg gcttccggcg tctcaacgcg ctttgagatt cccagctttt 480
cggccaatcc ctgcggtgca taggcgcgtg gctcgaccgc ttgcgggctg atggtgacgt 540
ggcccactgg tggccgctcc agggcctcgt agaacgcctg aatgcgcgtg tgacgtgcct 600
tgctgccctc gatgccccgt tgcagcccta gatcggccac agcggccgca aacgtggtct 660
ggtcgcgggt catctgcgct ttgttgccga tgaactcctt ggccgacagc ctgccgtcct 720
gcgtcagcgg caccacgaac gcggtcatgt gcgggctggt ttcgtcacgg tggatgctgg 780
ccgtcacgat gcgatccgcc ccgtacttgt ccgccagcca cttgtgcgcc ttctcgaaga 840
acgccgcctg ctgttcttgg ctggccgact tccaccattc cgggctggcc gtcatgacgt 900
actcgaccgc caacacagcg tccttgcgcc gcttctctgg cagcaactcg cgcagtcggc 960
ccatcgcttc atcggtgctg ctggccgccc agtgctcgtt ctctggcgtc ctgctggcgt 1020
cagcgttggg cgtctcgcgc tcgcggtagg cgtgcttgag actggccgcc acgttgccca 1080
ttttcgccag cttcttgcat cgcatgatcg cgtatgccgc catgcctgcc cctccctttt 1140
ggtgtccaac cggctcgacg gggcagcgc aaggcggtgc ctccggcggg ccactcaatg 1200
cttgagtata ctcactagac tttgcttcgc aaagtcgtga ccgcctacgg cggctgcggc 1260
gccctacggg cttgctctcc gggcttcgcc ctgcgcggtc gctgcgctcc cttgccagcc 1320
cgtggatatg tggacgatgg ccgcgagcgg ccaccggctg gctcgcttcg ctcggcccgt 1380
ggacaaccct gctggacaag ctgatggaca ggctgcgcct gcccacgagc ttgaccacag 1440
ggattgccca ccggctaccc agccttcgac cacataccca ccggctccaa ctgcgcggcc 1500
tgcggccttg ccccatcaat ttttttaatt ttctctgggg aaaagcctcc ggcctgcggc 1560
ctgcgcgctt cgcttgccgg ttggacacca agtggaaggc gggtcaaggc tcgcgcagcg 1620
accgcgcagc ggcttggcct tgacgcgcct ggaacgaccc aagcctatgc gagtgggggc 1680
agtcgaaggc gaagcccgcc cgcctgcccc ccgagcctca cggcggcgag tgcgggggtt 1740
ccaagggggc agcgccacct tgggcaaggc cgaaggccgc gcagtcgatc aacaagcccc 1800
ggaggggcca ctttttgccg gagggggagc cgcgccgaag gcgtggggga accccgcagg 1860
ggtgcccttc tttgggcacc aaagaactag atatagggcg aaatgcgaaa gacttaaaaa 1920
tcaacaactt aaaaaagggg ggtacgcaac agctcattgc ggcacccccc gcaatagctc 1980
attgcgtagg ttaaagaaaa tctgtaattg actgccactt ttacgcaacg cataattgtt 2040
gtcgcgctgc cgaaaagttg cagctgattg cgcatggtgc cgcaaccgtg cggcacccta 2100

-continued ccgcatggag ataagcatgg ccacgcagtc cagagaaatc ggcattcaag ccaagaacaa 2160
gcccggtcac tgggtgcaaa cggaacgcaa agcgcatgag gcgtgggccg ggcttattgc 2220
gaggaaaccc acggcggcaa tgctgctgca tcacctcgtg gcgcagatgg gccaccagaa 2280
cgccgtggtg gtcagccaga agacactttc caagctcatc ggacgttctt tgcggacggt 2340
ccaatacgca gtcaaggact tggtggccga gcgctggatc tccgtcgtga agctcaacgg 2400
ccccggcacc gtgtcggcct acgtggtcaa tgaccgcgtg gcgtggggcc agccccgcga 2460
ccagttgcgc ctgtcggtgt tcagtgccgc cgtggtggtt gatcacgacg accaggacga 2520
atcgctgttg gggcatggcg acctgcgccg catcccgacc ctgtatccgg gcgagcagca 2580
actaccgacc ggccccggcg aggagccgcc cagccagccc ggcattccgg gcatggaacc 2640
agacctgcca gccttgaccg aaacggagga atgggaacgg cgcgggcagc agcgcctgcc 2700
gatgcccgat gagccgtgtt ttctggacga tggcgagccg ttggagccgc cgacacgggt 2760
cacgctgccg cgccggtagt acgtaagagg ttccaacttt caccataatg aaataagatc 2820
actaccgggc gtattttttg agttatcgag attttcagga gctaaggaag ctaaaatgag 2880
tattcaacat ttccgtgtcg cccttattcc cttttttgcg gcattttgcc ttcctgtttt 2940
tgctcaccca gaaacgctgg tgaaagtaaa agatgctgaa gatcagttgg gtgcacgagt 3000
gggttacatc gaactggatc tcaacagcgg taagatcctt gagagtttac gccccgaaga 3060
acgttttcca atgatgagca cttttaaagt tctgctatgt ggcgcggtat tatcccgtat 3120
tgacgccggg caagagcaac tcggtcgccg catacactat tctcagaatg acttggttga 3180
gtactcacca gtcacagaaa agcatctcac ggatggcatg acagtaagag aattatgcag 3240
tgctgccata accatgagtg ataacactgc ggccaactta cttctggcaa cgatcggagg 3300
accgaaggag ctaaccgctt ttttgcacaa catgggggat catgtaactc gccttgatcg 3360
ttgggaaccg gagctgaatg aagccatacc aaacgacgag cgtgacacca cgatgcctgt 3420
agcaatggca acaacgttgc gcaaactatt aactggcgaa ctacttactc tagcttcccg 3480
gcaacaatta atagactgga tggaggcgga taaagttgca ggatcacttc tgcgctcggc 3540
cctcccggct ggctggttta ttgctgataa atctggagcc ggtgagcgtg ggtctcgcgg 3600
tatcattgca gcactggggc cagatggtaa gccctcccgc atcgtagtta tctacacgac 3660
ggggagtcag gcaactatgg atgaacgaaa tagacagatc gctgagatag gtgcctcact 3720
gattaagcat tggtaatgag gatcccccctc aagtcaaaag cctccggtcg gaggcttttg 3780
actttctgct atggaggtca ggtatgattt tgcattaggc accccaggct ttacacttta 3840
tgcttccggc tcgtatgttg tgtggaattg tgagcggata acaatttcac actctagaga 3900
attcgtc 3907

<210> SEQ ID NO 26
<211> LENGTH: 3863
<212> TYPE: DNA
<213> ORGANISM: Escherichia coli

<400> SEQUENCE: 26
aacgaattca agcttgatat cattcaggac gagcctcaga ctccagcgta actggactga 60
aaacaaacta aagcgccctt gtggcgcttt agttttgttc cgctcatgat aataatggtt 120
tcttagacgt caggtggcac ttttcgggga aatgtgcgcg cccgcgttcc tgctggcgct 180
gggcctgttt ctggcgctgg acttcccgct gttccgtcag cagcttttcg cccacggcct 240

-continued

```
tgatgatcgc ggcggccttg gcctgcatat cccgattcaa cggccccagg gcgtccagaa    300
cgggcttcag gcgctcccga aggtctcggg ccgtctcttg ggcttgatcg gccttcttgc    360
gcatctcacg cgctcctgcg gcggcctgta gggcaggctc atacccctgc cgaaccgctt    420
ttgtcagccg gtcggccacg gcttccggcg tctcaacgcg ctttgagatt cccagctttt    480
cggccaatcc ctgcggtgca taggcgcgtg gctcgaccgc ttgcgggctg atggtgacgt    540
ggcccactgg tggccgctcc agggcctcgt agaacgcctg aatgcgcgtg tgacgtgcct    600
tgctgccctc gatgccccgt tgcagcccta gatcggccac agcggccgca aacgtggtct    660
ggtcgcgggt catctgcgct ttgttgccga tgaactcctt ggccgacagc ctgccgtcct    720
gcgtcagcgg caccacgaac gcggtcatgt gcgggctggt ttcgtcacgg tggatgctgg    780
ccgtcacgat gcgatccgcc ccgtacttgt ccgccagcca cttgtgcgcc ttctcgaaga    840
acgccgcctg ctgttcttgg ctggccgact tccaccattc cgggctggcc gtcatgacgt    900
actcgaccgc caacacagcg tccttgcgcc gcttctctgg cagcaactcg cgcagtcggc    960
ccatcgcttc atcggtgctg ctggccgccc agtgctcgtt ctctggcgtc ctgctggcgt   1020
cagcgttggg cgtctcgcgc tcgcggtagg cgtgcttgag actggccgcc acgttgccca   1080
ttttcgccag cttcttgcat cgcatgatcg cgtatgccgc catgcctgcc cctccctttt   1140
ggtgtccaac cggctcgacg ggggcagcgc aaggcggtgc ctccggcggg ccactcaatg   1200
cttgagtata ctcactagac tttgcttcgc aaagtcgtga ccgcctacgg cggctgcggc   1260
gccctacggg cttgctctcc gggcttcgcc ctgcgcggtc gctgcgctcc cttgccagcc   1320
cgtggatatg tggacgatgg ccgcgagcgg ccaccggctg gctcgcttcg ctcggcccgt   1380
ggacaaccct gctggacaag ctgatggaca ggctgcgcct gcccacgagc ttgaccacag   1440
ggattgccca ccggctaccc agccttcgac cacataccca ccggctccaa ctgcgcggcc   1500
tgcggccttg ccccatcaat ttttttaatt ttctctgggg aaaagcctcc ggcctgcggc   1560
ctgcgcgctt cgcttgccgg ttggacacca agtggaaggc gggtcaaggc tcgcgcagcg   1620
accgcgcagc ggcttggcct tgacgcgcct ggaacgaccc aagcctatgc gagtgggggc   1680
agtcgaaggc gaagcccgcc cgcctgcccc ccgagcctca cggcggcgag tgcgggggtt   1740
ccaaggggggc agcgccacct tgggcaaggc cgaaggccgc gcagtcgatc aacaagcccc   1800
ggaggggcca ctttttgccg gagggggagc cgcgccgaag gcgtggggga accccgcagg   1860
ggtgcccttc tttgggcacc aaagaactag atatagggcg aaatgcgaaa gacttaaaaa   1920
tcaacaactt aaaaaagggg ggtacgcaac agctcattgc ggcaccccc gcaatagctc   1980
attgcgtagg ttaaagaaaa tctgtaattg actgccactt ttacgcaacg cataattgtt   2040
gtcgcgctgc cgaaaagttg cagctgattg cgcatggtgc cgcaaccgtg cggcacccta   2100
ccgcatggag ataagcatgg ccacgcagtc cagagaaatc ggcattcaag ccaagaacaa   2160
gcccggtcac tgggtgcaaa cggaacgcaa agcgcatgag gcgtgggccg ggcttattgc   2220
gaggaaaccc acggcggcaa tgctgctgca tcacctcgtg gcgcagatgg gccaccagaa   2280
cgccgtggtg gtcagccaga agacactttc caagctcatc ggacgttctt tgcggacggt   2340
ccaatacgca gtcaaggact tggtggccga gcgctggatc tccgtcgtga agctcaacgg   2400
ccccggcacc gtgtcggcct acgtggtcaa tgaccgcgtg gcgtggggcc agccccgcga   2460
ccagttgcgc ctgtcggtgt tcagtgccgc cgtggtggtt gatcacgacg accaggacga   2520
atcgctgttg gggcatggcg acctgcgccg catcccgacc ctgtatccgg gcgagcagca   2580
actaccgacc ggccccggcg aggagccgcc cagccagccc ggcattccgg gcatggaacc   2640
```

```
agacctgcca gccttgaccg aaacggagga atgggaacgg cgcgggcagc agcgcctgcc   2700

gatgcccgat gagccgtgtt ttctggacga tggcgagccg ttggagccgc cgacacgggt   2760

cacgctgccg cgccggtagt acgtaagagg ttccaacttt caccataatg aaataagatc   2820

actaccgggc gtattttttg agttatcgag attttcagga gctaaggaag ctaaaatgag   2880

ccatattcaa cgggaaacgt cttgctcgag gccgcgatta aattccaaca tggatgctga   2940

tttatatggg tataaatggg ctcgcgataa tgtcgggcaa tcaggtgcga caatctatcg   3000

attgtatggg aagcccgatg cgccagagtt gtttctgaaa catggcaaag gtagcgttgc   3060

caatgatgtt acagatgaga tggtcaggct aaactggctg acggaattta tgcctcttcc   3120

gaccatcaag cattttatcc gtactcctga tgatgcatgg ttactcacca ctgcgatccc   3180

agggaaaaca gcattccagg tattagaaga atatcctgat tcaggtgaaa atattgttga   3240

tgcgctggca gtgttcctgc gccggttgca ttcgattcct gtttgtaatt gtccttttaa   3300

cggcgatcgc gtatttcgtc tcgctcaggc gcaatcacga atgaataacg gtttggttgg   3360

tgcgagtgat tttgatgacg agcgtaatgg ctggcctgtt gaacaagtct ggaaagaaat   3420

gcataagctt ttgccattct caccggattc agtcgtcact catggtgatt tctcacttga   3480

taaccttatt tttgacgagg ggaaattaat aggttgtatt gatgttggac gagtcggaat   3540

cgcagaccga taccaggatc ttgccatcct atggaactgc ctcggtgagt tttctccttc   3600

attacagaaa cggctttttc aaaaatatgg tattgataat cctgatatga ataaattgca   3660

gtttcacttg atgctcgatg agtttttctg agggcggatc cccctcaagt caaaagcctc   3720

cggtcggagg cttttgactt tctgctatgg aggtcaggta tgattttgca ttaggcaccc   3780

caggctttac actttatgct tccggctcgt atgttgtgtg gaattgtgag cggataacaa   3840

tttcacactc tagagaattc gtc                                           3863
```

<210> SEQ ID NO 27
<211> LENGTH: 3709
<212> TYPE: DNA
<213> ORGANISM: Escherichia coli

<400> SEQUENCE: 27

```
aacgaattca agcttgatat cattcaggac gagcctcaga ctccagcgta actggactga     60

aaacaaacta aagcgccctt gtggcgcttt agttttgttc cgctcatgat aataatggtt    120

tcttagacgt caggtggcac ttttcgggga aatgtgcgcg cccgcgttcc tgctggcgct    180

gggcctgttt ctggcgctgg acttcccgct gttccgtcag cagcttttcg cccacggcct    240

tgatgatcgc ggcggccttg gcctgcatat cccgattcaa cggccccagg gcgtccagaa    300

cgggcttcag gcgctcccga aggtctcggg ccgtctcttg ggcttgatcg gccttcttgc    360

gcatctcacg cgctcctgcg gcggcctgta gggcaggctc ataccccctgc cgaaccgctt    420

ttgtcagccg gtcggccacg gcttccggcg tctcaacgcg ctttgagatt cccagctttt    480

cggccaatcc ctgcggtgca taggcgcgtg gctcgaccgc ttgcgggctg atggtgacgt    540

ggcccactgg tggccgctcc agggcctcgt agaacgcctg aatgcgcgtg tgacgtgcct    600

tgctgccctc gatgccccgt tgcagcccta gatcggccac agcggccgca aacgtggtct    660

ggtcgcgggt catctgcgct ttgttgccga tgaactcctt ggccgacagc ctgccgtcct    720

gcgtcagcgg caccacgaac gcggtcatgt gcgggctggt ttcgtcacgg tggatgctgg    780

ccgtcacgat gcgatccgcc ccgtacttgt ccgccagcca cttgtgcgcc ttctcgaaga    840
```

-continued

```
acgccgcctg ctgttcttgg ctggccgact tccaccattc cgggctggcc gtcatgacgt    900
actcgaccgc caacacagcg tccttgcgcc gcttctctgg cagcaactcg cgcagtcggc    960
ccatcgcttc atcggtgctg ctggccgccc agtgctcgtt ctctggcgtc ctgctggcgt   1020
cagcgttggg cgtctcgcgc tcgcggtagg cgtgcttgag actggccgcc acgttgccca   1080
ttttcgccag cttcttgcat cgcatgatcg cgtatgccgc catgcctgcc cctccctttt   1140
ggtgtccaac cggctcgacg ggggcagcgc aaggcggtgc ctccggcggg ccactcaatg   1200
cttgagtata ctcactagac tttgcttcgc aaagtcgtga ccgcctacgg cggctgcggc   1260
gccctacggg cttgctctcc gggcttcgcc ctgcgcggtc gctgcgctcc cttgccagcc   1320
cgtggatatg tggacgatgg ccgcgagcgg ccaccggctg gctcgcttcg ctcggcccgt   1380
ggacaaccct gctggacaag ctgatggaca ggctgcgcct gcccacgagc ttgaccacag   1440
ggattgccca ccggctaccc agccttcgac cacataccca ccggctccaa ctgcgcggcc   1500
tgcggccttg ccccatcaat ttttttaatt ttctctgggg aaaagcctcc ggcctgcggc   1560
ctgcgcgctt cgcttgccgg ttggacacca agtggaaggc gggtcaaggc tcgcgcagcg   1620
accgcgcagc ggcttggcct tgacgcgcct ggaacgaccc aagcctatgc gagtgggggc   1680
agtcgaaggc gaagcccgcc cgcctgcccc ccgagcctca cggcggcgag tgcgggggtt   1740
ccaagggggc agcgccacct tgggcaaggc cgaaggccgc gcagtcgatc aacaagcccc   1800
ggaggggcca ctttttgccg gagggggagc cgcgccgaag gcgtggggga accccgcagg   1860
ggtgcccttc tttgggcacc aaagaactag atatagggcg aaatgcgaaa gacttaaaaa   1920
tcaacaactt aaaaaagggg ggtacgcaac agctcattgc ggcacccccc gcaatagctc   1980
attgcgtagg ttaaagaaaa tctgtaattg actgccactt ttacgcaacg cataattgtt   2040
gtcgcgctgc cgaaaagttg cagctgattg cgcatggtgc cgcaaccgtg cggcacccta   2100
ccgcatggag ataagcatgg ccacgcagtc cagagaaatc ggcattcaag ccaagaacaa   2160
gcccggtcac tgggtgcaaa cggaacgcaa agcgcatgag gcgtgggccg ggcttattgc   2220
gaggaaaccc acggcggcaa tgctgctgca tcacctcgtg gcgcagatgg gccaccagaa   2280
cgccgtggtg gtcagccaga agacactttc caagctcatc ggacgttctt tgcggacggt   2340
ccaatacgca gtcaaggact tggtggccga gcgctggatc tccgtcgtga agctcaacgg   2400
ccccggcacc gtgtcggcct acgtggtcaa tgaccgcgtg gcgtggggcc agccccgcga   2460
ccagttgcgc ctgtcggtgt tcagtgccgc cgtggtggtt gatcacgacg accaggacga   2520
atcgctgttg gggcatggcg acctgcgccg catcccgacc ctgtatccgg gcgagcagca   2580
actaccgacc ggcccgggcg aggagccgcc cagccagccc ggcattccgg gcatggaacc   2640
agacctgcca gccttgaccg aaacggagga atgggaacgg cgcgggcagc agcgcctgcc   2700
gatgcccgat gagccgtgtt ttctggacga tggcgagccg ttggagccgc cgacacgggt   2760
cacgctgccg cgccggtagt acgtaagagg ttccaacttt caccataatg aaataagatc   2820
actaccgggc gtattttttg agttatcgag attttcagga gctaaggaag ctaaaatgga   2880
gaaaaaaatc actggatata ccaccgttga tatatcccaa tggcatcgta aagaacattt   2940
tgaggcattt cagtcagttg ctcaatgtac ctataaccag accgttcagc tggatattac   3000
ggccttttta aagaccgtaa agaaaaataa gcacaagttt tatccggcct ttattcacat   3060
tcttgcccgc ctgatgaatg ctcatccgga attccgtatg gcaatgaaag acggtgagct   3120
ggtgatatgg gatagtgttc acccttgtta caccgttttc catgagcaaa ctgaaacgtt   3180
ttcatcgctc tggagtgaat accacgacga tttccggcag tttctacaca tatattcgca   3240
```

```
agatgtggcg tgttacggtg aaaacctggc ctatttccct aaagggttta ttgagaatat   3300

gtttttcgtc tcagccaatc cctgggtgag tttcaccagt tttgatttaa acgtggccaa   3360

tatggacaac ttcttcgccc ccgttttcac catgggcaaa tattatacgc aaggcgacaa   3420

ggtgctgatg ccgctggcga ttcaggttca tcatgccgtt tgtgatggct tccatgtcgg   3480

cagaatgctt aatgaattac aacagtactg cgatgagtgg cagggcgggg cgtaaacgcg   3540

tggatccccc tcaagtcaaa agcctccggt cggaggcttt tgactttctg ctatggaggt   3600

caggtatgat tttgcattag gcaccccagg ctttacactt tatgcttccg gctcgtatgt   3660

tgtgtggaat tgtgagcgga taacaatttc acactctaga gaattcgtc               3709
```

<210> SEQ ID NO 28
<211> LENGTH: 4241
<212> TYPE: DNA
<213> ORGANISM: Escherichia coli

<400> SEQUENCE: 28

```
aacgaattca agcttgatat cattcaggac gagcctcaga ctccagcgta actggactga     60

aaacaaacta aagcgccctt gtggcgcttt agttttgttc cgctcatgat aataatggtt    120

tcttagacgt caggtggcac ttttcgggga aatgtgcgcg cccgcgttcc tgctggcgct    180

gggcctgttt ctggcgctgg acttcccgct gttccgtcag cagcttttcg cccacggcct    240

tgatgatcgc ggcggccttg gcctgcatat cccgattcaa cggccccagg gcgtccagaa    300

cgggcttcag gcgctcccga aggtctcggg ccgtctcttg ggcttgatcg gccttcttgc    360

gcatctcacg cgctcctgcg gcggcctgta gggcaggctc atacccctgc cgaaccgctt    420

ttgtcagccg gtcggccacg gcttccggcg tctcaacgcg ctttgagatt cccagctttt    480

cggccaatcc ctgcggtgca taggcgcgtg gctcgaccgc ttgcgggctg atggtgacgt    540

ggcccactgg tggccgctcc agggcctcgt agaacgcctg aatgcgcgtg tgacgtgcct    600

tgctgccctc gatgccccgt tgcagcccta gatcggccac agcggccgca aacgtggtct    660

ggtcgcgggt catctgcgct ttgttgccga tgaactcctt ggccgacagc ctgccgtcct    720

gcgtcagcgg caccacgaac gcggtcatgt gcgggctggt ttcgtcacgg tggatgctgg    780

ccgtcacgat gcgatccgcc ccgtacttgt ccgccagcca cttgtgcgcc ttctcgaaga    840

acgccgcctg ctgttcttgg ctggccgact tccaccattc cgggctggcc gtcatgacgt    900

actcgaccgc caacacagcg tccttgcgcc gcttctctgg cagcaactcg cgcagtcggc    960

ccatcgcttc atcggtgctg ctggccgccc agtgctcgtt ctctggcgtc ctgctggcgt   1020

cagcgttggg cgtctcgcgc tcgcggtagg cgtgcttgag actggccgcc acgttgccca   1080

ttttcgccag cttcttgcat cgcatgatcg cgtatgccgc catgcctgcc cctccctttt   1140

ggtgtccaac cggctcgacg ggggcagcgc aaggcggtgc ctccggcggg ccactcaatg   1200

cttgagtata ctcactagac tttgcttcgc aaagtcgtga ccgcctacgg cggctgcggc   1260

gccctacggg cttgctctcc gggcttcgcc ctgcgcggtc gctgcgctcc cttgccagcc   1320

cgtggatatg tggacgatgg ccgcgagcgg ccaccggctg gctcgcttcg ctcggcccgt   1380

ggacaaccct gctggacaag ctgatggaca ggctgcgcct gcccacgagc ttgaccacag   1440

ggattgccca ccggctaccc agccttcgac cacataccca ccggctccaa ctgcgcggcc   1500

tgcggccttg ccccatcaat ttttttaatt ttctctgggg aaaagcctcc ggcctgcggc   1560

ctgcgcgctt cgcttgccgg ttggacacca agtggaaggc gggtcaaggc tcgcgcagcg   1620
```

-continued

```
accgcgcagc ggcttggcct tgacgcgcct ggaacgaccc aagcctatgc gagtgggggc   1680
agtcgaaggc gaagcccgcc cgcctgcccc ccgagcctca cggcggcgag tgcgggggtt   1740
ccaaggggc  agcgccacct tgggcaaggc cgaaggccgc gcagtcgatc aacaagcccc   1800
ggaggggcca ctttttgccg gagggggagc cgcgccgaag gcgtggggga accccgcagg   1860
ggtgcccttc tttgggcacc aaagaactag atatagggcg aaatgcgaaa gacttaaaaa   1920
tcaacaactt aaaaaagggg ggtacgcaac agctcattgc ggcaccccc  gcaatagctc   1980
attgcgtagg ttaaagaaaa tctgtaattg actgccactt ttacgcaacg cataattgtt   2040
gtcgcgctgc cgaaaagttg cagctgattg cgcatggtgc cgcaaccgtg cggcacccta   2100
ccgcatggag ataagcatgg ccacgcagtc cagagaaatc ggcattcaag ccaagaacaa   2160
gcccggtcac tgggtgcaaa cggaacgcaa agcgcatgag gcgtgggccg ggcttattgc   2220
gaggaaaccc acggcggcaa tgctgctgca tcacctcgtg gcgcagatgg gccaccagaa   2280
cgccgtggtg gtcagccaga agacactttc caagctcatc ggacgttctt tgcggacggt   2340
ccaatacgca gtcaaggact tggtggccga gcgctggatc tccgtcgtga agctcaacgg   2400
ccccggcacc gtgtcggcct acgtggtcaa tgaccgcgtg gcgtggggcc agccccgcga   2460
ccagttgcgc ctgtcggtgt tcagtgccgc cgtggtggtt gatcacgacg accaggacga   2520
atcgctgttg gggcatggcg acctgcgccg catcccgacc ctgtatccgg gcgagcagca   2580
actaccgacc ggccccggcg aggagccgcc cagccagccc ggcattccgg gcatggaacc   2640
agacctgcca gccttgaccg aaacggagga atgggaacgg cgcgggcagc agcgcctgcc   2700
gatgcccgat gagccgtgtt ttctggacga tggcgagccg ttggagccgc cgacacgggt   2760
cacgctgccg cgccggtagt acgtaagagg ttccaacttt caccataatg aaataagatc   2820
actaccgggc gtattttttg agttatcgag attttcagga gctaaggaag ctaaaatgaa   2880
atctaacaat gcgctcatcg tcatcctcgg caccgtcacc ctggatgctg taggcatagg   2940
cttggttatg ccggtactgc cgggcctctt gcgggatatc gtccattccg acagcatcgc   3000
cagtcactat ggcgtgctgc tagcgctata tgcgttgatg caatttctat gcgcacccgt   3060
tctcggagca ctgtccgacc gctttggccg ccgcccagtc ctgctcgctt cgctacttgg   3120
agccactatc gactacgcga tcatggcgac cacacccgtc ctgtggatcc tctacgccgg   3180
acgcatcgtg gccggcatca ccggcgccac aggtgcggtt gctggcgcct atatcgccga   3240
catcaccgat ggggaagatc gggctcgcca cttcgggctc atgagcgctt gtttcggcgt   3300
gggtatggtg gcaggccccg tggccggggg actgttgggc gccatctcct tgcatgcacc   3360
attccttgcg gcggcggtgc tcaacggcct caacctacta ctgggctgct tcctaatgca   3420
ggagtcgcat aagggagagc gtcgaccgat gcccttgaga gccttcaacc cagtcagctc   3480
cttccggtgg gcgcggggca tgactatcgt cgccgcactt atgactgtct tctttatcat   3540
gcaactcgta ggacaggtgc cggcagcgct ctgggtcatt ttcggcgagg accgctttcg   3600
ctggagcgcg acgatgatcg gcctgtcgct tgcggtattc ggaatcttgc acgccctcgc   3660
tcaagccttc gtcactggtc ccgccaccaa acgtttcggc gagaagcagg ccattatcgc   3720
cggcatggcg gccgacgcgc tgggctacgt cttgctggcg ttcgcgacgc gaggctggat   3780
ggccttcccc attatgattc ttctcgcttc cggcggcatc gggatgcccg cgttgcaggc   3840
catgctgtcc aggcaggtag atgacgacca tcagggacag cttcaaggat cgctcgcggc   3900
tcttaccagc ctaacttcga tcactggacc gctgatcgtc acggcgattt atgccgcctc   3960
ggcgagcaca tggaacgggt tggcatggat tgtaggcgcc gccctatacc ttgtctgcct   4020
```

ccccgcgttg cgtcgcggtg catggagccg ggccacctcg acctgaatgg aagggatccc 4080
cctcaagtca aaagcctccg gtcggaggct tttgactttc tgctatggag gtcaggtatg 4140
attttgcatt aggcacccca ggctttacac tttatgcttc cggctcgtat gttgtgtgga 4200
attgtgagcg gataacaatt tcacactcta gagaattcgt c 4241

<210> SEQ ID NO 29
<211> LENGTH: 3284
<212> TYPE: DNA
<213> ORGANISM: Escherichia coli

<400> SEQUENCE: 29
aacgaattca agcttgatat cattcaggac gagcctcaga ctccagcgta actggactga 60
aaacaaacta aagcgccctt gtggcgcttt agttttgttc cgctcatgat aataatggtt 120
tcttagacgt caggtggcac ttttcgggga aatgtgcgcg cccgcgttcc tgctggcgct 180
gggcctgttt ctggcgctgg acttcccgct gttccgtcag cagcttttcg cccacggcct 240
tgatgatcgc ggcggccttg gcctgcatat cccgattcaa cggccccagg gcgtccagaa 300
cgggcttcag gcgctcccga aggtctcggg ccgtctcttg ggcttgatcg gccttcttgc 360
gcatctcacg cgctcctgcg gcggcctgta gggcaggctc ataccccctgc cgaaccgctt 420 ttgtcagccg gtcggccacg gcttccggcg tctcaacgcg ctttgagatt cccagctttt 480
cggccaatcc ctgcggtgca taggcgcgtg gctcgaccgc ttgcgggctg atggtgacgt 540
ggcccactgg tggccgctcc agggcctcgt agaacgcctg aatgcgcgtg tgacgtgcct 600
tgctgccctc gatgccccgt tgcagcccta gatcggccac agcggccgca aacgtggtct 660
ggtcgcgggt catctgcgct ttgttgccga tgaactcctt ggccgacagc ctgccgtcct 720
gcgtcagcgg caccacgaac gcggtcatgt gcgggctggt ttcgtcacgg tggatgctgg 780
ccgtcacgat gcgatccgcc ccgtacttgt ccgccagcca cttgtgcgcc ttctcgaaga 840
acgccgcctg ctgttcttgg ctggccgact tccaccattc cgggctggcc gtcatgacgt 900
actcgaccgc caacacagcg tccttgcgcc gcttctctgg cagcaactcg cgcagtcggc 960
ccatcgcttc atcggtgctg ctggccgccc agtgctcgtt ctctggcgtc ctgctggcgt 1020
cagcgttggg cgtctcgcgc tcgcggtagg cgtgcttgag actggccgcc acgttgccca 1080
ttttcgccag cttcttgcat cgcatgatcg cgtatgccgc catgcctgcc cctccctttt 1140
ggtgtccaac cggctcgacg gggcagcgc aaggcggtgc ctccggcggg ccactcaatg 1200
cttgagtata ctcactagac tttgcttcgc aaagtcgtga ccgcctacgg cggctgcggc 1260
gccctacggg cttgctctcc gggcttcgcc ctgcgcggtc gctgcgctcc cttgccagcc 1320
cgtggatatg tggacgatgg ccgcgagcgg ccaccggctg gctcgcttcg ctcggcccgt 1380
ggacaaccct gctggacaag ctgatggaca ggctgcgcct gcccacgagc ttgaccacag 1440
ggattgccca ccggctaccc agccttcgac cacataccca ccggctccaa ctgcgcggcc 1500
tgcggccttg ccccatcaat ttttttaatt ttctctgggg aaaagcctcc ggcctgcggc 1560
ctgcgcgctt cgcttgccgg ttggacacca agtggaaggc gggtcaaggc tcgcgcagcg 1620
accgcgcagc ggcttggcct tgacgcgcct ggaacgaccc aagcctatgc gagtgggggc 1680
agtcgaaggc gaagcccgcc cgcctgcccc ccgagcctca cggcggcgag tgcgggggtt 1740 ccaaggggc agcgccacct tgggcaaggc cgaaggccgc gcagtcgatc aacaagcccc 1800
ggaggggcca ctttttgccg gagggggagc cgcgccgaag gcgtggggga accccgcagg 1860
ggtgcccttc tttgggcacc aaagaactag atatagggcg aaatgcgaaa gacttaaaaa 1920
tcaacaactt aaaaaagggg ggtacgcaac agctcattgc ggcacccccc gcaatagctc 1980
attgcgtagg ttaaagaaaa tctgtaattg actgccactt ttacgcaacg cataattgtt 2040
gtcgcgctgc cgaaaagttg cagctgattg cgcatggtgc cgcaaccgtg cggcacccta 2100
ccgcatggag ataagcatgg ccacgcagtc cagagaaatc ggcattcaag ccaagaacaa 2160
gcccggtcac tgggtgcaaa cggaacgcaa agcgcatgag gcgtgggccg ggcttattgc 2220
gaggaaaccc acggcggcaa tgctgctgca tcacctcgtg gcgcagatgg gccaccagaa 2280
cgccgtggtg gtcagccaga agacactttc caagctcatc ggacgttctt tgcggacggt 2340
ccaatacgca gtcaaggact tggtggccga gcgctggatc tccgtcgtga agctcaacgg 2400
ccccggcacc gtgtcggcct acgtggtcaa tgaccgcgtg gcgtggggcc agccccgcga 2460
ccagttgcgc ctgtcggtgt tcagtgccgc cgtggtggtt gatcacgacg accaggacga 2520
atcgctgttg gggcatggcg acctgcgccg catcccgacc ctgtatccgg gcgagcagca 2580
actaccgacc ggccccggcg aggagccgcc cagccagccc ggcattccgg gcatggaacc 2640
agacctgcca gccttgaccg aaacggagga atgggaacgg cgcgggcagc agcgcctgcc 2700
gatgcccgat gagccgtgtt ttctggacga tggcgagccg ttggagccgc cgacacgggt 2760
cacgctgccg cgccggtagt acgtaagagg ttccaacttt caccataatg aaataagatc 2820
actaccgggc gtattttttg agttatcgag attttcagga gctaaggaag ctaaaatggg 2880
tcaaagtagc gatgaagcca acgctcccgt tgcagggcag tttgcgcttc ccctgagtgc 2940
cacctttggc ttaggggatc gcgtacgcaa gaaatctggt gccgcttggc agggtcaagt 3000
cgtcggttgg tattgcacaa aactcactcc tgaaggctat gcggtcgagt ccgaatccca 3060
cccaggctca gtgcaaattt atcctgtggc tgcacttgaa cgtgtggcct aagaatggat 3120
ccccctcaag tcaaaagcct ccggtcggag gcttttgact ttctgctatg gaggtcaggt 3180
atgattttgc attaggcacc ccaggcttta cactttatgc ttccggctcg tatgttgtgt 3240
ggaattgtga gcggataaca atttcacact ctagagaatt cgtc 3284

<210> SEQ ID NO 30
<211> LENGTH: 5922
<212> TYPE: DNA
<213> ORGANISM: Escherichia coli

<400> SEQUENCE: 30
aacgaattca agcttgatat cattcaggac gagcctcaga ctccagcgta actggactga 60
aaacaaacta aagcgccctt gtggcgcttt agttttgttc cgctcatgat aataatggtt 120
tcttagacgt caggtggcac ttttcgggga aatgtgcgcg cccgcgttcc tgctggcgct 180
gggcctgttt ctggcgctgg acttcccgct gttccgtcag cagcttttcg cccacggcct 240
tgatgatcgc ggcggccttg gcctgcatat cccgattcaa cggccccagg gcgtccagaa 300
cgggcttcag gcgctcccga aggtctcggg ccgtctcttg ggcttgatcg gccttcttgc 360
gcatctcacg cgctcctgcg gcggcctgta gggcaggctc atacccctgc cgaaccgctt 420
ttgtcagccg gtcggccacg gcttccggcg tctcaacgcg ctttgagatt cccagctttt 480
cggccaatcc ctgcggtgca taggcgcgtg gctcgaccgc ttgcgggctg atggtgacgt 540
ggcccactgg tggccgctcc agggcctcgt agaacgcctg aatgcgcgtg tgacgtgcct 600
tgctgccctc gatgccccgt tgcagcccta gatcggccac agcggccgca aacgtggtct 660
ggtcgcgggt catctgcgct ttgttgccga tgaactcctt ggccgacagc ctgccgtcct 720

-continued

```
gcgtcagcgg caccacgaac gcggtcatgt gcgggctggt ttcgtcacgg tggatgctgg    780
ccgtcacgat gcgatccgcc ccgtacttgt ccgccagcca cttgtgcgcc ttctcgaaga    840
acgccgcctg ctgttcttgg ctggccgact tccaccattc cgggctggcc gtcatgacgt    900
actcgaccgc caacacagcg tccttgcgcc gcttctctgg cagcaactcg cgcagtcggc    960
ccatcgcttc atcggtgctg ctggccgccc agtgctcgtt ctctggcgtc ctgctggcgt   1020
cagcgttggg cgtctcgcgc tcgcggtagg cgtgcttgag actggccgcc acgttgccca   1080
ttttcgccag cttcttgcat cgcatgatcg cgtatgccgc catgcctgcc cctccctttt   1140
ggtgtccaac cggctcgacg gggcagcgc aaggcggtgc ctccggcggg ccactcaatg    1200
cttgagtata ctcactagac tttgcttcgc aaagtcgtga ccgcctacgg cggctgcggc   1260
gccctacggg cttgctctcc gggcttcgcc ctgcgcggtc gctgcgctcc cttgccagcc   1320
cgtggatatg tggacgatgg ccgcgagcgg ccaccggctg gctcgcttcg ctcggcccgt   1380
ggacaaccct gctggacaag ctgatggaca ggctgcgcct gcccacgagc ttgaccacag   1440
ggattgccca ccggctaccc agccttcgac cacataccca ccggctccaa ctgcgcggcc   1500
tgcggccttg ccccatcaat ttttttaatt ttctctgggg aaaagcctcc ggcctgcggc   1560
ctgcgcgctt cgcttgccgg ttggacacca agtggaaggc gggtcaaggc tcgcgcagcg   1620
accgcgcagc ggcttggcct tgacgcgcct ggaacgaccc aagcctatgc gagtgggggc   1680
agtcgaaggc gaagcccgcc cgcctgcccc ccgagcctca cggcggcgag tgcgggggtt   1740
ccaagggggc agcgccacct tgggcaaggc cgaaggccgc gcagtcgatc aacaagcccc   1800
ggaggggcca ctttttgccg gagggggagc cgcgccgaag gcgtggggga accccgcagg   1860
ggtgcccttc tttgggcacc aaagaactag atatagggcg aaatgcgaaa gacttaaaaa   1920
tcaacaactt aaaaaagggg ggtacgcaac agctcattgc ggcacccccc gcaatagctc   1980
attgcgtagg ttaaagaaaa tctgtaattg actgccactt ttacgcaacg cataattgtt   2040
gtcgcgctgc cgaaaagttg cagctgattg cgcatggtgc cgcaaccgtg cggcacccta   2100
ccgcatggag ataagcatgg ccacgcagtc cagagaaatc ggcattcaag ccaagaacaa   2160
gcccggtcac tgggtgcaaa cggaacgcaa agcgcatgag gcgtgggccg ggcttattgc   2220
gaggaaaccc acggcggcaa tgctgctgca tcacctcgtg gcgcagatgg gccaccagaa   2280
cgccgtggtg gtcagccaga agacactttc caagctcatc ggacgttctt tgcggacggt   2340
ccaatacgca gtcaaggact tggtggccga gcgctggatc tccgtcgtga agctcaacgg   2400
ccccggcacc gtgtcggcct acgtggtcaa tgaccgcgtg gcgtggggcc agccccgcga   2460
ccagttgcgc ctgtcggtgt tcagtgccgc cgtggtggtt gatcacgacg accaggacga   2520
atcgctgttg ggcatggcg acctgcgccg catcccgacc ctgtatccgg gcgagcagca    2580
actaccgacc ggccccggcg aggagccgcc cagccagccc ggcattccgg gcatggaacc   2640
agacctgcca gccttgaccg aaacggagga atgggaacgg cgcgggcagc agcgcctgcc   2700
gatgcccgat gagccgtgtt ttctggacga tggcgagccg ttggagccgc cgacacgggt   2760
cacgctgccg cgccggtagt acgtaagagg ttccaacttt caccataatg aaataagatc   2820
actaccgggc gtattttttg agttatcgag attttcagga gctaaggaag ctaaaatgga   2880
agaacaaagc gtgaacatgg cgcgattgaa gggggaggtt ttgcccgccc tcttcgcgtc   2940
gccggcgacg attggcgagt acggggccgg catcgacggg gcggattccc tcaacgagct   3000
gtcgaatctg atggagcacg gcgcagttgc cgcgctggcc gacaaaatca gccagatcgt   3060
```

-continued

```
ggcgaagctg gccgacgcgg acccccgcaa gatcgcggaa aagcctacct ggttcgagaa   3120
gatgcttggc cgtgaggttg aacgccaggt gaggtatcag gtcgcccgca agacgctcga   3180
ccagttgctg gacgaagccg agggcgtagc gcagcgcgtg cgggacacgt tgcgcgcctt   3240
ggatgacatg ctcaatacgc atgaggccga ggtagaccgg ctcagagcct acattcaagc   3300
cgggcgcgag ttcctggacg agaaccccga ggccggcgcg gccaaggccg gcgtgatcga   3360
gttcgacaag ccgcgcgaac gcttcgcgcg caagctcgcc aacctggcaa ccctcatggc   3420
gtcccatgaa atgagcgtca ctcagatgaa gctcacgcgg gcgcaggccg tggacatgct   3480
ggaccgcttc tctgaaacgg catccgtcct ggtgcccgtc tggcgtcagc acaccctcgc   3540
gctcatcacc accaagaaca tgaatccggc aatggtcgcc gaggcggcca aagctcacca   3600
ggcgctcatg cggagccttt cgcagagcct ggaaggcatc aaccaataac acggcgggag   3660
aaccctatga acgcactgaa aacgacgcac gacgccaagg cccctatcgt cgccttcgac   3720
atgaccccgg caaccctgcg cgagctgggc ttgcaggaaa gcgacgtgcc ggaagtccat   3780
gcggtcgcgc agcggatcga ggtcggcagt ccgcagaccg ttgccgagtt cggccgcgac   3840
gtggccgagc acacgtcccg ctacgccgat agcctgctgg accaggtgcg caacagcgac   3900
ctggacgaag caggcgagaa actgacccag gttgtcgcca aggcccgttc cctgaacgtc   3960
ggccctttgt ccgacaaccg ttcccgcctg cccctgattg gcccgctgat cgaccgcttc   4020
cgcgtccgtt cgacgggctt catggcgcgc ttcgacacga cccgcgagca gatcgaacac   4080
ctggtcagcg aagtgcagac cacccagcaa ggcatcgcgc agcgcaatgc ctcgctcgac   4140
gaaatgttcg cagccgtgcg cgaggaacac cgccttcttg gcgtccacat cgcggccggc   4200
aaggtccgcc ttgccgagct gcgcgagcag gccgagggtc tgcgcggcaa tgtcgggaac   4260
gacccgggcc gcgtgcagga gctggccgac ctcgatgcga tggttgccaa cctggacaag   4320
cgcatcggcg acctgatcgc cttgcaacat tcggccatgc agagcctgcc gaccatccgc   4380
atgatccagg ccaacaacca gatgctggtc gataaattcc acaccatccg cgaaatcacc   4440
gtgccggcgt ggaagcggca attcatgctg gccttgagcc tcaacgagca gaagaacgcc   4500
gtcgaactgg ccacggccat cgacgacacc accaacgacc tgatgaagcg caatgcggcc   4560
ctgctgcatc gcacgtccgt cgagacggcg aaggagaacc aacgcctggt gatcgacgtg   4620
gacacgctca agcaggttca gacgacgctc atcaagaccg tcgaggacgt tattcgcatc   4680
cagcaggaag gcgtgcagaa gcgcaaggat gccgagaagc agatcgccgc aatgcgtggc   4740
gatcttcaag ccaagctgac ccgccagccc gtgcgcgagc tggcccaaca ggagtccgta   4800
tgaatgccac aaacaccgat gttttcgccc aggtaggcgg cctcgaggcc cgaggcgcga   4860
agatgaagaa gcggggcacc cgcttcctca tcgcggcgct ggcagtcctt gccattgccg   4920
ggatcggggc agtaacggga tgggcgatca gcccgagcgc gacgcccgga agcattgacg   4980
tgccgcaggt gctggcatcg acattcagcg accaggtgcc gggcagtgag ggcggcggcc   5040
tgggtggcgg cctgcccttc acttcggccg tcggggcatt cacggacttc atggcggggc   5100
cggcaatttt taccttgggc attcttggca tagtggtcgc gggtgccgtg ctcgtgttcg   5160
ggggtgaatt ctgcgggttc gtgcgatccg tctgcatgat ggtgatagcc gtcagcatga   5220
ttttcgtgtc gtcgaacttg gtgaagggca ttctcggcgg cgatcacgac gccggccctg   5280
cggagccttc gccgcgtgcg cgattcatgg cggccgtgga ggccaaggat ttcgcgcgag   5340
tgcaagagct gatcgaggcg cgtggagcca agtcggcggc tgattatgtc cttgcgcagc   5400
tcgccgtggc cgaaggtctg gaccgcaagc ctggtgcgcg cgtcgtggtc gggaaagcgg   5460
```

cgggcagcat ggcaatgccg cctgcggcgc tgggttttac gccaagggga gaagcggcat 5520
acgccatcga gcggtcagcc tatggtgagc cgaggtccag cattgcgaag cagtaccagc 5580
aggaatggaa ccggaaggcg gcgacctggt gggcgatggc cggtgtggcc ggcatcatcg 5640
gcgcgatcct ggcggcggcg gcaaccggct ttgttgggct ggcagtgtcg atccgcaacc 5700
gagtgaagcg cgtgcgcgac ctgttggtga tggagccggg tgcagagcca taagggatcc 5760
ccctcaagtc aaaagcctcc ggtcggaggc ttttgacttt ctgctatgga ggtcaggtat 5820
gattttgcat taggcacccc aggctttaca ctttatgctt ccggctcgta tgttgtgtgg 5880
aattgtgagc ggataacaat ttcacactct agagaattcg tc 5922

<210> SEQ ID NO 31
<211> LENGTH: 2662
<212> TYPE: DNA
<213> ORGANISM: Escherichia coli

<400> SEQUENCE: 31
aacgaattca agcttgatat cattcaggac gagcctcaga ctccagcgta actggactga 60
aaacaaacta aagcgccctt gtggcgcttt agttttgttc cgcggccacc ggctggctcg 120
cttcgctcgg cccgtggaca accctgctgg acaagctgat ggacaggctg cgcctgccca 180
cgagcttgac cacagggatt gcccaccggc tacccagcct tcgaccacat acccaccggc 240
tccaactgcg cggcctgcgg ccttgcccca tcaatttttt taattttctc tggggaaaag 300
cctccggcct gcggcctgcg cgcttcgctt gccggttgga caccaagtgg aaggcgggtc 360
aaggctcgcg cagcgaccgc gcagcggctt ggccttgacg cgcctggaac gacccaagcc 420
tatgcgagtg gggcagtcg aaggcgaagc ccgcccgcct gccccccgag cctcacggcg 480
gcgagtgcgg gggttccaag gggcagcgc caccttgggc aaggccgaag gccgcgcagt 540
cgatcaacaa gccccggagg ggccactttt tgccggaggg ggagccgcgc cgaaggcgtg 600
ggggaacccc gcaggggtgc ccttctttgg gcaccaaaga actagatata gggcgaaatg 660
cgaaagactt aaaaatcaac aacttaaaaa aggggggtac gcaacagctc attgcggcac 720
cccccgcaat agctcattgc gtaggttaaa gaaaatctgt aattgactgc cacttttacg 780
caacgcataa ttgttgtcgc gctgccgaaa agttgcagct gattgcgcat ggtgccgcaa 840
ccgtgcggca ccctaccgca tggagataag catggccacg cagtccagag aaatcggcat 900
tcaagccaag aacaagcccg gtcactgggt gcaaacggaa cgcaaagcgc atgaggcgtg 960
ggccgggctt attgcgagga aacccacggc ggcaatgctg ctgcatcacc tcgtggcgca 1020
gatgggccac cagaacgccg tggtggtcag ccagaagaca ctttccaagc tcatcggacg 1080
ttctttgcgg acggtccaat acgcagtcaa ggacttggtg gccgagcgct ggatctccgt 1140
cgtgaagctc aacggccccg gcaccgtgtc ggcctacgtg gtcaatgacc gcgtggcgtg 1200 ggccagccc cgcgaccagt tgcgcctgtc ggtgttcagt gccgccgtgg tggttgatca 1260
cgacgaccag gacgaatcgc tgttggggca tggcgacctg cgccgcatcc cgaccctgta 1320
tccgggcgag cagcaactac cgaccggccc cggcgaggag ccgcccagcc agcccggcat 1380
tccgggcatg gaaccagacc tgccagcctt gaccgaaacg gaggaatggg aacggcgcgg 1440
gcagcagcgc ctgccgatgc ccgatgagcc gtgttttctg gacgatggcg agccgttgga 1500
gccgccgaca cgggtcacgc tgccgcgccg gtagtacgta agaggttcca actttcacca 1560
taatgaaata agatcactac cgggcgtatt ttttgagtta tcgagatttt caggagctaa 1620

-continued

```
ggaagctaaa atgagtattc aacatttccg tgtcgccctt attccctttt ttgcggcatt   1680

ttgccttcct gtttttgctc acccagaaac gctggtgaaa gtaaaagatg ctgaagatca   1740

gttgggtgca cgagtgggtt acatcgaact ggatctcaac agcggtaaga tccttgagag   1800

ttttcgcccc gaagaacgtt ttccaatgat gagcactttt aaagttctgc tatgtggcgc   1860

ggtattatcc cgtattgacg ccgggcaaga gcaactcggt cgccgcatac actattctca   1920

gaatgacttg gttgagtact caccagtcac agaaaagcat ctcacggatg gcatgacagt   1980

aagagaatta tgcagtgctg ccataaccat gagtgataac actgcggcca acttacttct   2040

ggcaacgatc ggaggaccga aggagctaac cgcttttttg cacaacatgg gggatcatgt   2100

aactcgcctt gatcgttggg aaccggagct gaatgaagcc ataccaaacg acgagcgtga   2160

caccacgatg cctgtagcaa tggcaacaac gttgcgcaaa ctattaactg gcgaactact   2220

tactctagct tcccggcaac aattaataga ctggatggag gcggataaag ttgcaggatc   2280

acttctgcgc tcggcccttcc cggctggctg gtttattgct gataaatctg gagccggtga   2340

gcgtgggtct cgcggtatca ttgcagcact ggggccagat ggtaagccct cccgcatcgt   2400

agttatctac acgacgggga gtcaggcaac tatggatgaa cgaaatagac agatcgctga   2460

gataggtgcc tcactgatta agcattggta atgaggatcc ccctcaagtc aaaagcctcc   2520

ggtcggaggc ttttgacttt ctgctatgga ggtcaggtat gattttgcat taggcacccc   2580

aggctttaca ctttatgctt ccggctcgta tgttgtgtgg aattgtgagc ggataacaat   2640

ttcacactct agagaattcg tc                                            2662
```

<210> SEQ ID NO 32
<211> LENGTH: 2618
<212> TYPE: DNA
<213> ORGANISM: Escherichia coli

<400> SEQUENCE: 32

```
aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180

cgagcttgac cacagggatt gcccaccggc tacccagcct tcgaccacat acccaccggc    240

tccaactgcg cggcctgcgg ccttgcccca tcaatttttt taattttctc tggggaaaag    300

cctccggcct gcggcctgcg cgcttcgctt gccggttgga caccaagtgg aaggcgggtc    360

aaggctcgcg cagcgaccgc gcagcggctt ggccttgacg cgcctggaac gacccaagcc    420

tatgcgagtg ggggcagtcg aaggcgaagc ccgcccgcct gcccccccgag cctcacggcg    480

gcgagtgcgg gggttccaag gggggcagcgc caccttgggc aaggccgaag gccgcgcagt    540

cgatcaacaa gccccggagg ggccactttt tgccggaggg ggagccgcgc cgaaggcgtg    600

ggggaacccc gcaggggtgc ccttctttgg gcaccaaaga actagatata gggcgaaatg    660

cgaaagactt aaaaatcaac aacttaaaaa aggggggtac gcaacagctc attgcggcac    720

cccccgcaat agctcattgc gtaggttaaa gaaaatctgt aattgactgc cacttttacg    780

caacgcataa ttgttgtcgc gctgccgaaa agttgcagct gattgcgcat ggtgccgcaa    840

ccgtgcggca ccctaccgca tggagataag catggccacg cagtccagag aaatcggcat    900

tcaagccaag aacaagcccg gtcactgggt gcaaacggaa cgcaaagcgc atgaggcgtg    960

ggccgggctt attgcgagga aacccacggc ggcaatgctg ctgcatcacc tcgtggcgca   1020

gatgggccac cagaacgccg tggtggtcag ccagaagaca ctttccaagc tcatcggacg   1080
```

-continued

```
ttctttgcgg acggtccaat acgcagtcaa ggacttggtg gccgagcgct ggatctccgt   1140
cgtgaagctc aacggccccg gcaccgtgtc ggcctacgtg gtcaatgacc gcgtggcgtg   1200
gggccagccc cgcgaccagt tgcgcctgtc ggtgttcagt gccgccgtgg tggttgatca   1260
cgacgaccag gacgaatcgc tgttggggca tggcgacctg cgccgcatcc cgaccctgta   1320
tccgggcgag cagcaactac cgaccggccc cggcgaggag ccgcccagcc agcccggcat   1380
tccgggcatg gaaccagacc tgccagcctt gaccgaaacg gaggaatggg aacggcgcgg   1440
gcagcagcgc ctgccgatgc ccgatgagcc gtgttttctg gacgatggcg agccgttgga   1500
gccgccgaca cgggtcacgc tgccgcgccg gtagtacgta agaggttcca actttcacca   1560
taatgaaata agatcactac cgggcgtatt ttttgagtta tcgagatttt caggagctaa   1620
ggaagctaaa atgagccata ttcaacggga aacgtcttgc tcgaggccgc gattaaattc   1680
caacatggat gctgatttat atgggtataa atgggctcgc gataatgtcg ggcaatcagg   1740
tgcgacaatc tatcgattgt atgggaagcc cgatgcgcca gagttgtttc tgaaacatgg   1800
caaaggtagc gttgccaatg atgttacaga tgagatggtc aggctaaact ggctgacgga   1860
atttatgcct cttccgacca tcaagcattt tatccgtact cctgatgatg catggttact   1920
caccactgcg atccccggga aaacagcatt ccaggtatta gaagaatatc ctgattcagg   1980
tgaaaatatt gttgatgcgc tggcagtgtt cctgcgccgg ttgcattcga ttcctgtttg   2040
taattgtcct tttaacggcg atcgcgtatt tcgtctcgct caggcgcaat cacgaatgaa   2100
taacggtttg gttggtgcga gtgattttga tgacgagcgt aatggctggc ctgttgaaca   2160
agtctggaaa gaaatgcata agcttttgcc attctcaccg gattcagtcg tcactcatgg   2220
tgatttctca cttgataacc ttatttttga cgaggggaaa ttaataggtt gtattgatgt   2280
tggacgagtc ggaatcgcag accgatacca ggatcttgcc atcctatgga actgcctcgg   2340
tgagttttct ccttcattac agaaacggct ttttcaaaaa tatggtattg ataatcctga   2400
tatgaataaa ttgcagtttc acttgatgct cgatgagttt ttctgagggc ggatcccccct   2460
caagtcaaaa gcctccggtc ggaggctttt gactttctgc tatggaggtc aggtatgatt   2520
ttgcattagg caccccaggc tttacacttt atgcttccgg ctcgtatgtt gtgtggaatt   2580
gtgagcggat aacaatttca cactctagag aattcgtc                           2618
```

```
<210> SEQ ID NO 33
<211> LENGTH: 2464
<212> TYPE: DNA
<213> ORGANISM: Escherichia coli

<400> SEQUENCE: 33

aacgaattca agcttgatat cattcaggac gagcctcaga ctccagcgta actggactga     60
aaacaaacta aagcgccctt gtggcgcttt agttttgttc cgcggccacc ggctggctcg    120
cttcgctcgg cccgtggaca accctgctgg acaagctgat ggacaggctg cgcctgccca    180
cgagcttgac cacagggatt gcccaccggc tacccagcct tcgaccacat acccaccggc    240
tccaactgcg cggcctgcgg ccttgcccca tcaatttttt taatttctc tggggaaaag    300
cctccggcct gcggcctgcg cgcttcgctt gccggttgga caccaagtgg aaggcgggtc    360
aaggctcgcg cagcgaccgc gcagcggctt ggccttgacg cgcctggaac gacccaagcc    420
tatgcgagtg ggggcagtcg aaggcgaagc ccgcccgcct gccccccgag cctcacggcg    480
gcgagtgcgg gggttccaag gggcagcgc caccttgggc aaggccgaag gccgcgcagt    540
```

-continued

```
cgatcaacaa gccccggagg ggccactttt tgccggaggg ggagccgcgc cgaaggcgtg    600

ggggaacccc gcaggggtgc ccttctttgg gcaccaaaga actagatata gggcgaaatg    660

cgaaagactt aaaaatcaac aacttaaaaa aggggggtac gcaacagctc attgcggcac    720

cccccgcaat agctcattgc gtaggttaaa gaaaatctgt aattgactgc cacttttacg    780

caacgcataa ttgttgtcgc gctgccgaaa agttgcagct gattgcgcat ggtgccgcaa    840

ccgtgcggca ccctaccgca tggagataag catggccacg cagtccagag aaatcggcat    900

tcaagccaag aacaagcccg gtcactgggt gcaaacggaa cgcaaagcgc atgaggcgtg    960

ggccgggctt attgcgagga aacccacggc ggcaatgctg ctgcatcacc tcgtggcgca   1020

gatgggccac cagaacgccg tggtggtcag ccagaagaca ctttccaagc tcatcggacg   1080

ttctttgcgg acggtccaat acgcagtcaa ggacttggtg gccgagcgct ggatctccgt   1140

cgtgaagctc aacggccccg gcaccgtgtc ggcctacgtg gtcaatgacc gcgtggcgtg   1200

gggccagccc cgcgaccagt tgcgcctgtc ggtgttcagt gccgccgtgg tggttgatca   1260

cgacgaccag gacgaatcgc tgttggggca tggcgacctg cgccgcatcc cgaccctgta   1320

tccgggcgag cagcaactac cgaccggccc cggcgaggag ccgcccagcc agcccggcat   1380

tccgggcatg gaaccagacc tgccagcctt gaccgaaacg gaggaatggg aacggcgcgg   1440

gcagcagcgc ctgccgatgc ccgatgagcc gtgttttctg gacgatggcg agccgttgga   1500

gccgccgaca cgggtcacgc tgccgcgccg gtagtacgta agaggttcca actttcacca   1560

taatgaaata agatcactac cgggcgtatt ttttgagtta tcgagatttt caggagctaa   1620

ggaagctaaa atggagaaaa aaatcactgg atataccacc gttgatatat cccaatggca   1680

tcgtaaagaa cattttgagg catttcagtc agttgctcaa tgtacctata accagaccgt   1740

tcagctggat attacggcct ttttaaagac cgtaaagaaa aataagcaca agttttatcc   1800

ggcctttatt cacattcttg cccgcctgat gaatgctcat ccggaattcc gtatggcaat   1860

gaaagacggt gagctggtga tatgggatag tgttcaccct tgttacaccg ttttccatga   1920

gcaaactgaa acgttttcat cgctctggag tgaataccac gacgatttcc ggcagtttct   1980

acacatatat tcgcaagatg tggcgtgtta cggtgaaaac ctggcctatt tccctaaagg   2040

gtttattgag aatatgtttt tcgtctcagc caatccctgg gtgagtttca ccagttttga   2100

tttaaacgtg gccaatatgg acaacttctt cgcccccgtt ttcaccatgg gcaaatatta   2160

tacgcaaggc gacaaggtgc tgatgccgct ggcgattcag gttcatcatg ccgtttgtga   2220

tggcttccat gtcggcagaa tgcttaatga attacaacag tactgcgatg agtggcaggg   2280

cggggcgtaa acgcgtggat ccccctcaag tcaaaagcct ccggtcggag gcttttgact   2340

ttctgctatg gaggtcaggt atgattttgc attaggcacc ccaggcttta cactttatgc   2400

ttccggctcg tatgttgtgt ggaattgtga gcggataaca atttcacact ctagagaatt   2460

cgtc                                                                2464
```

<210> SEQ ID NO 34
<211> LENGTH: 2996
<212> TYPE: DNA
<213> ORGANISM: Escherichia coli

<400> SEQUENCE: 34

```
aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180
```

-continued

```
cgagcttgac cacagggatt gcccaccggc tacccagcct tcgaccacat acccaccggc    240
tccaactgcg cggcctgcgg ccttgcccca tcaatttttt taattttctc tggggaaaag    300
cctccggcct gcggcctgcg cgcttcgctt gccggttgga caccaagtgg aaggcgggtc    360
aaggctcgcg cagcgaccgc gcagcggctt ggccttgacg cgcctggaac gacccaagcc    420
tatgcgagtg gggcagtcg aaggcgaagc ccgcccgcct gccccccgag cctcacggcg    480
gcgagtgcgg gggttccaag ggggcagcgc caccttgggc aaggccgaag gccgcgcagt    540
cgatcaacaa gccccggagg ggccactttt tgccggaggg ggagccgcgc cgaaggcgtg    600
ggggaacccc gcaggggtgc ccttctttgg gcaccaaaga actagatata gggcgaaatg    660
cgaaagactt aaaaatcaac aacttaaaaa aggggggtac gcaacagctc attgcggcac    720
cccccgcaat agctcattgc gtaggttaaa gaaaatctgt aattgactgc cacttttacg    780
caacgcataa ttgttgtcgc gctgccgaaa agttgcagct gattgcgcat ggtgccgcaa    840
ccgtgcggca ccctaccgca tggagataag catggccacg cagtccagag aaatcggcat    900
tcaagccaag aacaagcccg gtcactgggt gcaaacggaa cgcaaagcgc atgaggcgtg    960
ggccgggctt attgcgagga aacccacggc ggcaatgctg ctgcatcacc tcgtggcgca   1020
gatgggccac cagaacgccg tggtggtcag ccagaagaca ctttccaagc tcatcggacg   1080
ttctttgcgg acggtccaat acgcagtcaa ggacttggtg gccgagcgct ggatctccgt   1140
cgtgaagctc aacggccccg gcaccgtgtc ggcctacgtg gtcaatgacc gcgtggcgtg   1200
gggccagccc cgcgaccagt tgcgcctgtc ggtgttcagt gccgccgtgg tggttgatca   1260
cgacgaccag gacgaatcgc tgttggggca tggcgacctg cgccgcatcc cgaccctgta   1320
tccgggcgag cagcaactac cgaccggccc cggcgaggag ccgcccagcc agcccggcat   1380
tccgggcatg gaaccagacc tgccagcctt gaccgaaacg gaggaatggg aacggcgcgg   1440
gcagcagcgc ctgccgatgc ccgatgagcc gtgttttctg gacgatggcg agccgttgga   1500
gccgccgaca cgggtcacgc tgccgcgccg gtagtacgta agaggttcca actttcacca   1560
taatgaaata agatcactac cgggcgtatt ttttgagtta tcgagatttt caggagctaa   1620
ggaagctaaa atgaaatcta acaatgcgct catcgtcatc ctcggcaccg tcaccctgga   1680
tgctgtaggc ataggcttgg ttatgccggt actgccgggc ctcttgcggg atatcgtcca   1740
ttccgacagc atcgccagtc actatggcgt gctgctagcg ctatatgcgt tgatgcaatt   1800
tctatgcgca cccgttctcg gagcactgtc cgaccgcttt ggccgccgcc cagtcctgct   1860
cgcttcgcta cttggagcca ctatcgacta cgcgatcatg gcgaccacac ccgtcctgtg   1920
gatcctctac gccggacgca tcgtggccgg catcaccggc gccacaggtg cggttgctgg   1980
cgcctatatc gccgacatca ccgatgggga agatcgggct cgccacttcg ggctcatgag   2040
cgcttgtttc ggcgtgggta tggtggcagg ccccgtggcc gggggactgt tgggcgccat   2100
ctccttgcat gcaccattcc ttgcggcggc ggtgctcaac ggcctcaacc tactactggg   2160
ctgcttccta atgcaggagt cgcataaggg agagcgtcga ccgatgccct tgagagcctt   2220
caacccagtc agctccttcc ggtgggcgcg gggcatgact atcgtcgccg cacttatgac   2280
tgtcttcttt atcatgcaac tcgtaggaca ggtgccggca gcgctctggg tcattttcgg   2340
cgaggaccgc tttcgctgga gcgcgacgat gatcggcctg tcgcttgcgg tattcggaat   2400
cttgcacgcc ctcgctcaag ccttcgtcac tggtcccgcc accaaacgtt tcggcgagaa   2460
gcaggccatt atcgccggca tggcggccga cgcgctgggc tacgtcttgc tggcgttcgc   2520
```

-continued gacgcgaggc tggatggcct tccccattat gattcttctc gcttccggcg gcatcgggat 2580
gcccgcgttg caggccatgc tgtccaggca ggtagatgac gaccatcagg gacagcttca 2640
aggatcgctc gcggctctta ccagcctaac ttcgatcact ggaccgctga tcgtcacggc 2700
gatttatgcc gcctcggcga gcacatggaa cgggttggca tggattgtag gcgccgccct 2760
ataccttgtc tgcctccccg cgttgcgtcg cggtgcatgg agccgggcca cctcgacctg 2820
aatggaaggg atcccccctca agtcaaaagc ctccggtcgg aggcttttga ctttctgcta 2880
tggaggtcag gtatgatttt gcattaggca ccccaggctt tacactttat gcttccggct 2940
cgtatgttgt gtggaattgt gagcggataa caatttcaca ctctagagaa ttcgtc 2996

<210> SEQ ID NO 35
<211> LENGTH: 2039
<212> TYPE: DNA
<213> ORGANISM: Escherichia coli

<400> SEQUENCE: 35
aacgaattca agcttgatat cattcaggac gagcctcaga ctccagcgta actggactga 60
aaacaaacta aagcgccctt gtggcgcttt agttttgttc cgcggccacc ggctggctcg 120
cttcgctcgg cccgtggaca accctgctgg acaagctgat ggacaggctg cgcctgccca 180
cgagcttgac cacagggatt gcccaccggc tacccagcct tcgaccacat acccaccggc 240
tccaactgcg cggcctgcgg ccttgcccca tcaatttttt taatttttctc tggggaaaag 300 cctccggcct gcggcctgcg cgcttcgctt gccggttgga caccaagtgg aaggcgggtc 360
aaggctcgcg cagcgaccgc gcagcggctt ggccttgacg cgcctggaac gacccaagcc 420
tatgcgagtg ggggcagtcg aaggcgaagc ccgcccgcct gcccccccgag cctcacggcg 480 gcgagtgcgg gggttccaag ggggcagcgc caccttgggc aaggccgaag gccgcgcagt 540
cgatcaacaa gccccggagg ggccactttt tgccggaggg ggagccgcgc cgaaggcgtg 600
ggggaacccc gcaggggtgc ccttctttgg gcaccaaaga actagatata gggcgaaatg 660
cgaaagactt aaaaatcaac aacttaaaaa aggggggtac gcaacagctc attgcggcac 720
cccccgcaat agctcattgc gtaggttaaa gaaaatctgt aattgactgc cacttttacg 780
caacgcataa ttgttgtcgc gctgccgaaa agttgcagct gattgcgcat ggtgccgcaa 840
ccgtgcggca ccctaccgca tggagataag catggccacg cagtccagag aaatcggcat 900
tcaagccaag aacaagcccg gtcactgggt gcaaacggaa cgcaaagcgc atgaggcgtg 960
ggccgggctt attgcgagga aacccacggc ggcaatgctg ctgcatcacc tcgtggcgca 1020
gatgggccac cagaacgccg tggtggtcag ccagaagaca ctttccaagc tcatcggacg 1080
ttctttgcgg acggtccaat acgcagtcaa ggacttggtg gccgagcgct ggatctccgt 1140
cgtgaagctc aacggccccg gcaccgtgtc ggcctacgtg gtcaatgacc gcgtggcgtg 1200 ggccagccc cgcgaccagt tgcgcctgtc ggtgttcagt gccgccgtgg tggttgatca 1260
cgacgaccag gacgaatcgc tgttggggca tggcgacctg cgccgcatcc cgaccctgta 1320
tccgggcgag cagcaactac cgaccggccc cggcgaggag ccgcccagcc agcccggcat 1380
tccgggcatg gaaccagacc tgccagcctt gaccgaaacg gaggaatggg aacggcgcgg 1440
gcagcagcgc ctgccgatgc ccgatgagcc gtgttttctg gacgatggcg agccgttgga 1500
gccgccgaca cgggtcacgc tgccgcgccg gtagtacgta agaggttcca actttcacca 1560
taatgaaata agatcactac cgggcgtatt ttttgagtta tcgagatttt caggagctaa 1620
ggaagctaaa atgggtcaaa gtagcgatga agccaacgct cccgttgcag ggcagtttgc 1680

```
gcttcccctg agtgccacct ttggcttagg ggatcgcgta cgcaagaaat ctggtgccgc   1740

ttggcagggt caagtcgtcg gttggtattg cacaaaactc actcctgaag gctatgcggt   1800

cgagtccgaa tcccacccag gctcagtgca aatttatcct gtggctgcac ttgaacgtgt   1860

ggcctaagaa tggatccccc tcaagtcaaa agcctccggt cggaggcttt tgactttctg   1920

ctatggaggt caggtatgat ttgcattag gcaccccagg ctttacactt tatgcttccg   1980

gctcgtatgt tgtgtggaat tgtgagcgga taacaatttc acactctaga gaattcgtc    2039
```

<210> SEQ ID NO 36
<211> LENGTH: 4677
<212> TYPE: DNA
<213> ORGANISM: Escherichia coli

<400> SEQUENCE: 36

```
aacgaattca agcttgatat cattcaggac gagcctcaga ctccagcgta actggactga     60

aaacaaacta aagcgccctt gtggcgcttt agttttgttc cgcggccacc ggctggctcg    120

cttcgctcgg cccgtggaca accctgctgg acaagctgat ggacaggctg cgcctgccca    180

cgagcttgac cacagggatt gcccaccggc tacccagcct tcgaccacat acccaccggc    240

tccaactgcg cggcctgcgg ccttgcccca tcaatttttt taattttctc tggggaaaag    300

cctccggcct gcggcctgcg cgcttcgctt gccggttgga caccaagtgg aaggcgggtc    360

aaggctcgcg cagcgaccgc gcagcggctt ggccttgacg cgcctggaac gacccaagcc    420

tatgcgagtg gggcagtcg aaggcgaagc ccgcccgcct gccccccgag cctcacggcg    480

gcgagtgcgg gggttccaag gggcagcgc caccttgggc aaggccgaag gccgcgcagt    540

cgatcaacaa gccccggagg ggccactttt tgccggaggg ggagccgcgc cgaaggcgtg    600

ggggaacccc gcaggggtgc ccttctttgg gcaccaaaga actagatata gggcgaaatg    660

cgaaagactt aaaaatcaac aacttaaaaa agggggtac gcaacagctc attgcggcac    720

cccccgcaat agctcattgc gtaggttaaa gaaaatctgt aattgactgc cacttttacg    780

caacgcataa ttgttgtcgc gctgccgaaa agttgcagct gattgcgcat ggtgccgcaa    840

ccgtgcggca ccctaccgca tggagataag catggccacg cagtccagag aaatcggcat    900

tcaagccaag aacaagcccg gtcactgggt gcaaacggaa cgcaaagcgc atgaggcgtg    960

ggccgggctt attgcgagga aacccacggc ggcaatgctg ctgcatcacc tcgtggcgca   1020

gatgggccac cagaacgccg tggtggtcag ccagaagaca ctttccaagc tcatcggacg   1080

ttctttgcgg acggtccaat acgcagtcaa ggacttggtg gccgagcgct ggatctccgt   1140

cgtgaagctc aacggccccg gcaccgtgtc ggcctacgtg gtcaatgacc gcgtggcgtg   1200

gggccagccc cgcgaccagt tgcgcctgtc ggtgttcagt gccgccgtgg tggttgatca   1260

cgacgaccag gacgaatcgc tgttggggca tggcgacctg cgccgcatcc cgaccctgta   1320

tccgggcgag cagcaactac cgaccggccc cggcgaggag ccgcccagcc agcccggcat   1380

tccgggcatg gaaccagacc tgccagcctt gaccgaaacg gaggaatggg aacggcgcgg   1440

gcagcagcgc ctgccgatgc ccgatgagcc gtgttttctg gacgatggcg agccgttgga   1500

gccgccgaca cgggtcacgc tgccgcgccg gtagtacgta agaggttcca actttcacca   1560

taatgaaata agatcactac cgggcgtatt ttttgagtta tcgagatttt caggagctaa   1620

ggaagctaaa atggaagaac aaagcgtgaa catggcgcga ttgaaggggg aggttttgcc   1680

cgccctcttc gcgtcgccgg cgacgattgg cgagtacggg gccggcatcg acggggcgga   1740
```

-continued

```
ttccctcaac gagctgtcga atctgatgga gcacggcgca gttgccgcgc tggccgacaa   1800
aatcagccag atcgtggcga agctggccga cgcggacccc cgcaagatcg cggaaaagcc   1860
tacctggttc gagaagatgc ttggccgtga ggttgaacgc caggtgaggt atcaggtcgc   1920
ccgcaagacg ctcgaccagt tgctggacga agccgagggc gtagcgcagc gcgtgcggga   1980
cacgttgcgc gccttggatg acatgctcaa tacgcatgag gccgaggtag accggctcag   2040
agcctacatt caagccgggc gcgagttcct ggacgagaac cccgaggccg gcgcggccaa   2100
ggccggcgtg atcgagttcg acaagccgcg cgaacgcttc gcgcgcaagc tcgccaacct   2160
ggcaaccctc atggcgtccc atgaaatgag cgtcactcag atgaagctca cgcgggcgca   2220
ggccgtggac atgctggacc gcttctctga aacggcatcc gtcctggtgc ccgtctggcg   2280
tcagcacacc ctcgcgctca tcaccaccaa gaacatgaat ccggcaatgg tcgccgaggc   2340
ggccaaagct caccaggcgc tcatgcggag cctttcgcag agcctggaag gcatcaacca   2400
ataacacggc gggagaaccc tatgaacgca ctgaaaacga cgcacgacgc caaggcccct   2460
atcgtcgcct tcgacatgac ccccggcaacc ctgcgcgagc tgggcttgca ggaaagcgac   2520
gtgccggaag tccatgcggt cgcgcagcgg atcgaggtcg gcagtccgca gaccgttgcc   2580
gagttcggcc gcgacgtggc cgagcacacg tcccgctacg ccgatagcct gctggaccag   2640
gtgcgcaaca gcgacctgga cgaagcaggc gagaaactga cccaggttgt cgccaaggcc   2700
cgttccctga acgtcggccc tttgtccgac aaccgttccc gcctgcccct gattggcccg   2760
ctgatcgacc gcttccgcgt ccgttcgacg ggcttcatgg cgcgcttcga cacgacccgc   2820
gagcagatcg aacacctggt cagcgaagtg cagaccaccc agcaaggcat cgcgcagcgc   2880
aatgcctcgc tcgacgaaat gttcgcagcc gtgcgcgagg aacaccgcct tcttggcgtc   2940
cacatcgcgg ccggcaaggt ccgccttgcc gagctgcgcg agcaggccga gggtctgcgc   3000
ggcaatgtcg ggaacgaccc gggccgcgtg caggagctgg ccgacctcga tgcgatggtt   3060
gccaacctgg acaagcgcat cggcgacctg atcgccttgc aacattcggc catgcagagc   3120
ctgccgacca tccgcatgat ccaggccaac aaccagatgc tggtcgataa attccacacc   3180
atccgcgaaa tcaccgtgcc ggcgtggaag cggcaattca tgctggcctt gagcctcaac   3240
gagcagaaga acgccgtcga actggccacg gccatcgacg acaccaccaa cgacctgatg   3300
aagcgcaatg cggccctgct gcatcgcacg tccgtcgaga cggcgaagga gaaccaacgc   3360
ctggtgatcg acgtggacac gctcaagcag gttcagacga cgctcatcaa gaccgtcgag   3420
gacgttattc gcatccagca ggaaggcgtg cagaagcgca aggatgccga gaagcagatc   3480
gccgcaatgc gtggcgatct tcaagccaag ctgacccgcc agcccgtgcg cgagctggcc   3540
caacaggagt ccgtatgaat gccacaaaca ccgatgtttt cgcccaggta ggcggcctcg   3600
aggcccgagg cgcgaagatg aagaagcggg gcacccgctt cctcatcgcg gcgctggcag   3660
tccttgccat tgccgggatc ggggcagtaa cgggatgggc gatcagcccg agcgcgacgc   3720
ccggaagcat tgacgtgccg caggtgctgg catcgacatt cagcgaccag gtgccgggca   3780
gtgagggcgg cggcctgggt ggcggcctgc ccttcacttc ggccgtcggg gcattcacgg   3840
acttcatggc ggggccggca atttttacct tgggcattct tggcatagtg gtcgcgggtg   3900
ccgtgctcgt gttcgggggt gaattctgcg ggttcgtgcg atccgtctgc atgatggtga   3960
tagccgtcag catgattttc gtgtcgtcga acttggtgaa gggcattctc ggcggcgatc   4020
acgacgccgg ccctgcggag ccttcgccgc gtgcgcgatt catggcggcc gtggaggcca   4080
aggatttcgc gcgagtgcaa gagctgatcg aggcgcgtgg agccaagtcg gcggctgatt   4140
```

atgtccttgc gcagctcgcc gtggccgaag gtctggaccg caagcctggt gcgcgcgtcg 4200
tggtcgggaa agcggcgggc agcatggcaa tgccgcctgc ggcgctgggt tttacgccaa 4260
ggggagaagc ggcatacgcc atcgagcggt cagcctatgg tgagccgagg tccagcattg 4320
cgaagcagta ccagcaggaa tggaaccgga aggcggcgac ctggtgggcg atggccggtg 4380
tggccggcat catcggcgcg atcctggcgg cggcggcaac cggctttgtt gggctggcag 4440
tgtcgatccg caaccgagtg aagcgcgtgc gcgacctgtt ggtgatggag ccgggtgcag 4500
agccataagg gatccccctc aagtcaaaag cctccggtcg gaggcttttg actttctgct 4560
atggaggtca ggtatgattt tgcattaggc accccaggct ttacacttta tgcttccggc 4620
tcgtatgttg tgtggaattg tgagcggata acaatttcac actctagaga attcgtc 4677

<210> SEQ ID NO 37
<211> LENGTH: 31
<212> TYPE: DNA
<213> ORGANISM: Artificial
<220> FEATURE:
<223> OTHER INFORMATION: primer Mob_R

<400> SEQUENCE: 37
cgctcatgat aataatggtt tcttagacgt c 31

<210> SEQ ID NO 38
<211> LENGTH: 23
<212> TYPE: DNA
<213> ORGANISM: Artificial
<220> FEATURE:
<223> OTHER INFORMATION: primer Rep_R

<400> SEQUENCE: 38
ctaccggcgc ggcagcgtga ccc 23

<210> SEQ ID NO 39
<211> LENGTH: 38
<212> TYPE: DNA
<213> ORGANISM: Artificial
<220> FEATURE:
<223> OTHER INFORMATION: primer Amp_F

<400> SEQUENCE: 39
tacgtaagag gttccaactt tcaccataat gaaataag 38

<210> SEQ ID NO 40
<211> LENGTH: 61
<212> TYPE: DNA
<213> ORGANISM: Artificial
<220> FEATURE:
<223> OTHER INFORMATION: primer SoxRT_SL1

<400> SEQUENCE: 40
aacaaaacta aagcgccaca agggcgcttt agtttgtttt cagtccagtt acgctggagt 60
c 61

<210> SEQ ID NO 41
<211> LENGTH: 19
<212> TYPE: DNA
<213> ORGANISM: Artificial
<220> FEATURE:
<223> OTHER INFORMATION: primer Lac_F

<400> SEQUENCE: 41
tgcattaggc accccaggc 19

<210> SEQ ID NO 42
<211> LENGTH: 22
<212> TYPE: DNA
<213> ORGANISM: Artificial
<220> FEATURE:
<223> OTHER INFORMATION: primer Lac_R

<400> SEQUENCE: 42
aaatttatta gcgccattcg cc 22

<210> SEQ ID NO 43
<211> LENGTH: 19
<212> TYPE: DNA
<213> ORGANISM: Artificial
<220> FEATURE:
<223> OTHER INFORMATION: primer LacReplace1

<400> SEQUENCE: 43
cggataacaa tttcacact 19

<210> SEQ ID NO 44
<211> LENGTH: 23
<212> TYPE: DNA
<213> ORGANISM: Artificial
<220> FEATURE:
<223> OTHER INFORMATION: primer LacReplace 2

<400> SEQUENCE: 44
ctagagtgtg aaattgttat ccg 23

<210> SEQ ID NO 45
<211> LENGTH: 28
<212> TYPE: DNA
<213> ORGANISM: Artificial
<220> FEATURE:
<223> OTHER INFORMATION: primer pBAD_F

<400> SEQUENCE: 45
ttatgacaac ttgacggcta catcattc 28

<210> SEQ ID NO 46
<211> LENGTH: 26
<212> TYPE: DNA
<213> ORGANISM: Artificial
<220> FEATURE:
<223> OTHER INFORMATION: primer PBAD_R

<400> SEQUENCE: 46
gtaccatggt gaattcctcc tgctag 26

<210> SEQ ID NO 47
<211> LENGTH: 28
<212> TYPE: DNA
<213> ORGANISM: Artificial
<220> FEATURE:
<223> OTHER INFORMATION: primer Kan_F

<400> SEQUENCE: 47
ggaagctaaa atgagccata ttcaacgg 28

<210> SEQ ID NO 48
<211> LENGTH: 21
<212> TYPE: DNA
<213> ORGANISM: Artificial

<220> FEATURE:
<223> OTHER INFORMATION: primer Kan_R

<400> SEQUENCE: 48
gccctcagaa aaactcatcg a 21

<210> SEQ ID NO 49
<211> LENGTH: 28
<212> TYPE: DNA
<213> ORGANISM: Artificial
<220> FEATURE:
<223> OTHER INFORMATION: primer Tet_F

<400> SEQUENCE: 49
ggaagctaaa atgaaatcta acaatgcg 28

<210> SEQ ID NO 50
<211> LENGTH: 18
<212> TYPE: DNA
<213> ORGANISM: Artificial
<220> FEATURE:
<223> OTHER INFORMATION: primer Tet_R

<400> SEQUENCE: 50
cttccattca ggtcgagg 18

<210> SEQ ID NO 51
<211> LENGTH: 28
<212> TYPE: DNA
<213> ORGANISM: Artificial
<220> FEATURE:
<223> OTHER INFORMATION: primer Tmp_F

<400> SEQUENCE: 51
ggaagctaaa atgggtcaaa gtagcgat 28

<210> SEQ ID NO 52
<211> LENGTH: 22
<212> TYPE: DNA
<213> ORGANISM: Artificial
<220> FEATURE:
<223> OTHER INFORMATION: primer Tmp_R

<400> SEQUENCE: 52
attcttaggc cacacgttca ag 22

<210> SEQ ID NO 53
<211> LENGTH: 22
<212> TYPE: DNA
<213> ORGANISM: Artificial
<220> FEATURE:
<223> OTHER INFORMATION: primer Tell_F

<400> SEQUENCE: 53
ggaagctaaa atggaagaac aa 22

<210> SEQ ID NO 54
<211> LENGTH: 22
<212> TYPE: DNA
<213> ORGANISM: Artificial
<220> FEATURE:
<223> OTHER INFORMATION: primer Tell_R

<400> SEQUENCE: 54
cttatggctc tgcacccggc tc 22

```
<210> SEQ ID NO 55
<211> LENGTH: 22
<212> TYPE: DNA
<213> ORGANISM: Artificial
<220> FEATURE:
<223> OTHER INFORMATION: primer RC_1

<400> SEQUENCE: 55

ggatcccccct caagtcaaaa gc                                          22


<210> SEQ ID NO 56
<211> LENGTH: 28
<212> TYPE: DNA
<213> ORGANISM: Artificial
<220> FEATURE:
<223> OTHER INFORMATION: primer RC_2

<400> SEQUENCE: 56

ttagctcctg aaaatctcga taactcaa                                     28


<210> SEQ ID NO 57
<211> LENGTH: 30
<212> TYPE: DNA
<213> ORGANISM: Artificial
<220> FEATURE:
<223> OTHER INFORMATION: primer pBT_Lib1

<400> SEQUENCE: 57

gatatcattc aggacgagcc tcagactcca                                   30


<210> SEQ ID NO 58
<211> LENGTH: 42
<212> TYPE: DNA
<213> ORGANISM: Artificial
<220> FEATURE:
<223> OTHER INFORMATION: primer pBT_Lib2

<400> SEQUENCE: 58

gatatcgctc aatactgacc atttaaatca tacctgacct cc                     42


<210> SEQ ID NO 59
<211> LENGTH: 40
<212> TYPE: DNA
<213> ORGANISM: Artificial
<220> FEATURE:
<223> OTHER INFORMATION: primer pBTB_Lib2

<400> SEQUENCE: 59

ctctagccca aaaaaacggg tatggagaaa cagtagagag                        40
```